United States Patent
Verkade et al.

(10) Patent No.: US 11,951,175 B2
(45) Date of Patent: *Apr. 9, 2024

(54) BIOCONJUGATES CONTAINING SULFAMIDE LINKERS FOR USE IN TREATMENT

(71) Applicant: Synaffix B.V., Oss (NL)

(72) Inventors: Jorge Merijn Mathieu Verkade, Eindhoven (NL); Maria Antonia Wijdeven, Wijchen (NL); Petrus Josephus Jacobus Maria Van De Sande, Eindhoven (NL); Remon Van Geel, Lithoijen (NL); Floris Louis Van Delft, Nijmegen (NL); Sander Sebastiaan Van Berkel, Wijchen (NL)

(73) Assignee: Synaffix B.V., Oss (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/076,279

(22) PCT Filed: Feb. 8, 2017

(86) PCT No.: PCT/EP2017/052788
§ 371 (c)(1),
(2) Date: Aug. 7, 2018

(87) PCT Pub. No.: WO2017/137456
PCT Pub. Date: Aug. 17, 2017

(65) Prior Publication Data
US 2019/0262467 A1   Aug. 29, 2019

(30) Foreign Application Priority Data

Feb. 8, 2016  (EP) .................................. 16154712
Feb. 8, 2016  (EP) .................................. 16154739

(Continued)

(51) Int. Cl.
*A61K 47/68* (2017.01)
*A61K 47/54* (2017.01)
(Continued)

(52) U.S. Cl.
CPC ........ *A61K 47/6889* (2017.08); *A61K 47/549* (2017.08); *A61K 47/66* (2017.08);
(Continued)

(58) Field of Classification Search
None
See application file for complete search history.

(56) References Cited

U.S. PATENT DOCUMENTS 5,602,119 A   2/1997  Vazquez et al.
8,207,303 B2  6/2012  Cardarelli et al.
(Continued)

FOREIGN PATENT DOCUMENTS

CN    104623687 A   5/2015
EP    2 481 725 A1   8/2012
(Continued)

OTHER PUBLICATIONS

Lu et al. ("Lu", J. Am. Chem. Soc., 2010, 132, 1747-1749). (Year: 2010).*

(Continued)

*Primary Examiner* — Karl J Puttlitz
(74) *Attorney, Agent, or Firm* — Foley & Lardner LLP

(57) ABSTRACT

The present invention is based on the surprising finding that the linker employed in a bioconjugate, such as an anti-body-drug conjugate, is not therapeutically inert but has an effect on the therapeutic index of the bioconjugate. The present invention thus concerns a method for increasing the therapeutic index of a bioconjugate and the bioconjugates for use in treatment, in particular cancer. The bioconjugates accord- (Continued)

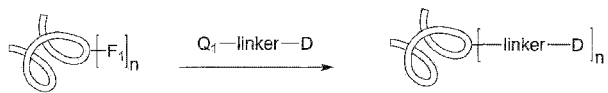

BOI = biomolecule of interest
D = MOI = molecule of interest (or target molecule)
$F_1$ = native or engineered functional group
$Q_1$ = reactive group specific for $F_1$
n = 1,2,3...

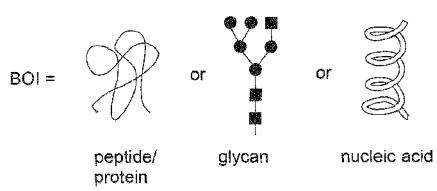

BOI =      peptide/protein     or     glycan     or     nucleic acid ing to the invention have a sulfamide linker comprising a group according to formula (1).

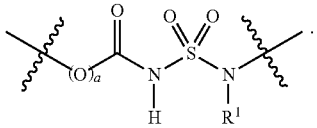

21 Claims, 23 Drawing Sheets

Specification includes a Sequence Listing.

(30) Foreign Application Priority Data

Jun. 8, 2016 (EP) .................................... 16173595
Jun. 8, 2016 (EP) .................................... 16173599

(51) Int. Cl.
  *A61K 47/66* (2017.01)
  *A61P 35/00* (2006.01)
  *C07K 14/435* (2006.01)

(52) U.S. Cl.
  CPC ...... *A61K 47/6803* (2017.08); *A61K 47/6817* (2017.08); *A61K 47/6849* (2017.08); *A61K 47/6851* (2017.08); *A61P 35/00* (2018.01); *C07K 14/435* (2013.01)

(56) References Cited

U.S. PATENT DOCUMENTS

| | | |
|---|---|---|
| 2005/0256030 A1 | 11/2005 | Feng |
| 2005/0276812 A1 | 12/2005 | Ebens et al. |
| 2007/0190597 A1 | 8/2007 | Agnew et al. |
| 2009/0047248 A1 | 2/2009 | Sun et al. |
| 2010/0260709 A1 | 10/2010 | Brandl et al. |
| 2017/0029490 A1* | 2/2017 | Winters ................... C07K 5/06 |

FOREIGN PATENT DOCUMENTS

| | | | |
|---|---|---|---|
| WO | WO-01/88535 A1 | 11/2001 | |
| WO | WO-03/082842 A1 | 10/2003 | |
| WO | WO-2006/000085 A1 | 1/2006 | |
| WO | WO-2008/060927 A2 | 5/2008 | |
| WO | WO-2008/070291 A2 | 6/2008 | |
| WO | WO-2009/067108 A1 | 5/2009 | |
| WO | WO-2011/136645 A1 | 11/2011 | |
| WO | WO-2014/065661 A1 | 5/2014 | |
| WO | WO-2014/100762 A1 | 6/2014 | |
| WO | WO-2014/177771 A1 | 11/2014 | |
| WO | WO-2015/057063 A1 | 4/2015 | |
| WO | WO-2015/057064 A1 | 4/2015 | |
| WO | WO-2015/057065 A1 | 4/2015 | |
| WO | WO-2015/057066 A1 | 4/2015 | |
| WO | WO-2015/095952 A1 | 7/2015 | |
| WO | WO-2015095953 A1 * | 7/2015 | .............. A61P 35/02 |
| WO | 2016053107 * | 4/2016 | |
| WO | WO-2016/022027 A1 | 4/2016 | |
| WO | WO-2016/053107 A1 | 4/2016 | |
| WO | WO-2016/170186 A1 | 10/2016 | |

OTHER PUBLICATIONS

U.S. Appl. No. 16/076,281, filed Aug. 7, 2018.
U.S. Appl. No. 16/076,293, filed Aug. 7, 2018.
U.S. Appl. No. 16/076,310, filed Aug. 7, 2018.
Babic, et al., "Synthesis of 1-C-linked diphosphate analogues of UDP-N-Ac-glucosamine and UDP-N-Ac-muramic acid", Tetrahedron 64(38): 9093-9100 (2008).
Beeril, et al, "Sortase Enzyme-Mediated Generation of Site-Specifically Conjugated Antibody Drug Conjugates with High In Vitro and In Vivo Potency", Public Library of Science 10(7): e013117-1 (2015).
Erickson, et al., "The Effect of Different Linkers on Target Cell Catabolismand Pharmacokinetics/Pharmacodynamics of Trastuzumab Maytansinoid Conjugages", Molecular Cancer Therapeutics 11(5): 1133-1142 (2012).
International Search Report and Written Opinion, dated May 29, 2017, issued in International Application No. PCT/EP2017/052791.
International Search Report and Written Opinion, dated Jun. 27, 2017, issued in corresponding International Application No. PCT/EP2017/052790.
International Search Report and Written Opinion, dated May 12, 2017, issued in International Application No. PCT/EP2017/052788.
International Search Report and Written Opinion, dated Jun. 7, 2017, issued in International Application No. PCT/EP2017/052719.
Krueger, et al., "Inhibitors of HCV NS5B polymerase: Synthesis and structure-activity relationships of N-alkyl-4-hydroxyquinolon-3-yl-benzothiadi azine sulfamides", Bioorganic & Medicinal Chemistry Letters 16(13): 3367-3370 (2006).
Lhospice, et al., "Site-Specific Conjugation of Monmethyl Auristatin E to Anti-CD30 Antibodies Improves Their Pharmacokinetics and Therapeutic Index in Roden Models", Molecular Pharmaceutics 12(6): 1863-1871 (2015).
Li, et al., "An Anti-HER2 Antibody Conjugated with Monomethyl Auristatin E is Highly Effective in HER2-Positive Human Gastric Cancer", Cancer Biology & Therapy 17(4): 346-354 (2016).
Melagraki, et al., "Identification of a series of novel derivatives as potent HCV inhibitors by a ligand-based virtual screening optimized procedure", Bioorganic & Medicinal Chemistry 15(23): 7237-7247 (2007).
Murphy-Benenato, et al., "Discovery of Efficacious Pseudomonas aeruginosa-Targeted Siderophore-Conjugated Monocarbams by Application of a Semi-Mechanistic Pharmacokinetic/Pharmacodynamic Model", Journal of Medicinal Chemistry 58(5): 2195-2205 (2015).
Phillips, et al., "Targeting HER2-Positive Breast Cancer with Trastuzumab-DM1, an Antibody-Cytotoxic Drug Conjugate", Cancer Research 68(22): 9280-9290 (2008).
Pillow, et al., "Site-Specific Trastuzumab Maytansinoid Antibody—Drug Conjugates with Improved Therapeutic Activity through Linker and Antibody Engineering", Journal of Medicinal Chemistry 57(19): 7890-7899 (2014).
Scott, et al., "Development and Properties of ß-Glucuronide Linkers for Monoclonal Antibody—Drug Conjugates", Bioconjugate Chemistry 17(3): 831-840 (2006).
Senter, et al., "Self-Hydrolyzing Maleimides Improve the Stability and Pharmacological Properties of Antibody-Drug Conjugates", Nature Biotechnology 32(10): 1059-1062 (2014).
Somu, et al., "Antitubercular Nucleosides that Inhibit Siderophore Biosynthesis: SAR of the Glycosyl Domain", Journal of Medicinal Chemistry 49(26): 7623-7635 (2006).
Van Geel, et al., "Chemoenzymatic Conjugation of Toxic Payloads to the Globally Conserved N-Glycan of Native mAbs Provides Homogeneous and Highly Efficacious Antibody—Drug Conjugates", Bioconjugate Chemistry 26(11): 2233-2242 (2015).
Yao, et al., "A Novel Humanized Anti-HER2 Antibody Conjugated with MMAE Exerts Potent Anti-Tumor Activity", Breast Cancer Research and Treatment 153(1): 123-133 (2015).
"Seattle Genetics' Antibody-Drug Conjugate Receives FDA Okay to Treat Lymphomas", Genetic Engineering & Biotechnology News, downloaded from https://www.genengnews.com/topics/drug-discovery/ seattle-genetics-antibody-drug-conjugate-receives-fda-okay-to-treat-lymphomas/ on Nov. 18, 2021 (Year: 2011), (3 pages).
"MDX-060 Monoclonal Antibody in Treating Patients With Refractory or Relapsed Lymphoma", US National Library of Medicine, downloaded from https://clinicaltrials.gov/ct2/show/NCT00059995?term=iratumumab&draw=2&rank=1 on Nov. 18, 2021 (Year: 2003), (9 pages).

* cited by examiner

Fig. 1
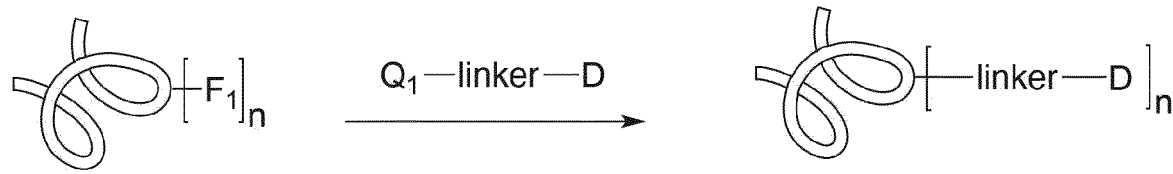
BOI
BOI = biomolecule of interest
D = MOI = molecule of interest (or target molecule)
$F_1$ = native or engineered functional group
$Q_1$ = reactive group specific for $F_1$
n = 1,2,3...
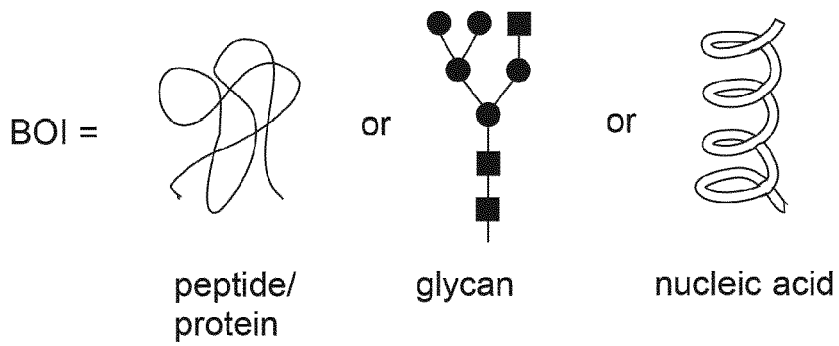
BOI =  peptide/protein  or  glycan  or  nucleic acid
Fig. 2
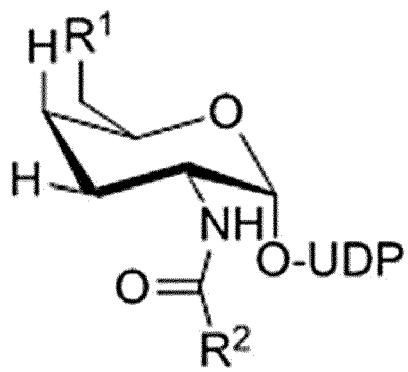
11a $R^1$ = OH; $R^2$ = $(CH_2)_2SH$
11b $R^1$ = OH; $R^2$ = $CH_2N_3$
11c $R^1$ = OH; $R^2$ = $CF_2N_3$
11d $R^1$ = $N_3$; $R^2$ = $CH_3$

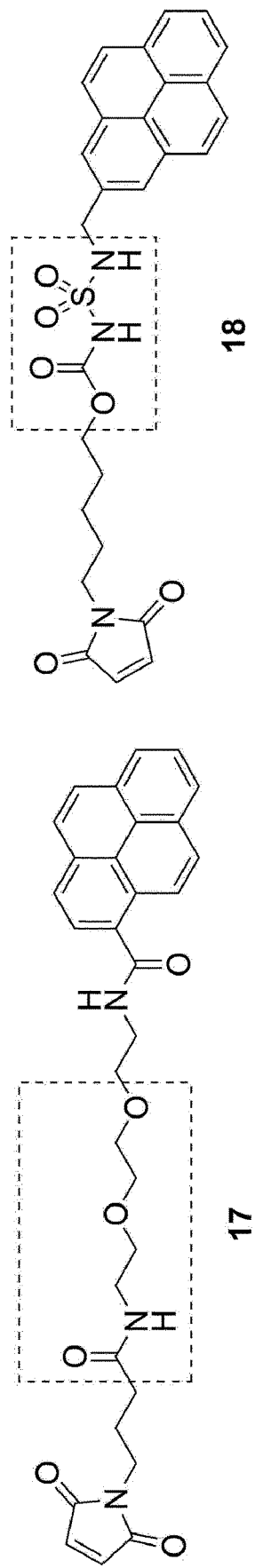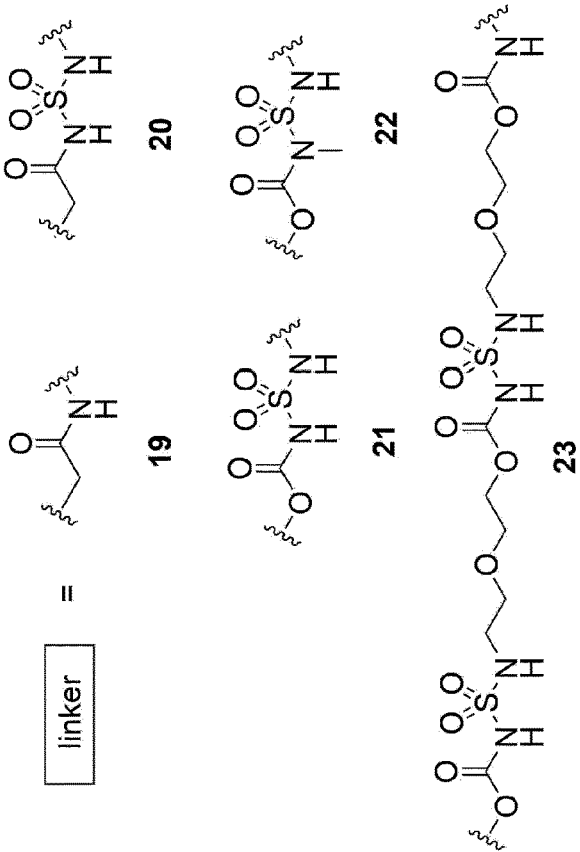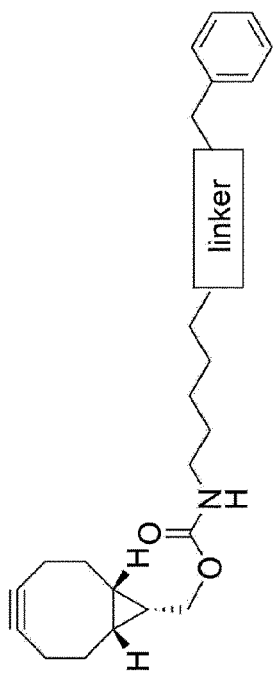
Fig. 5
Fig. 6

Fig. 8
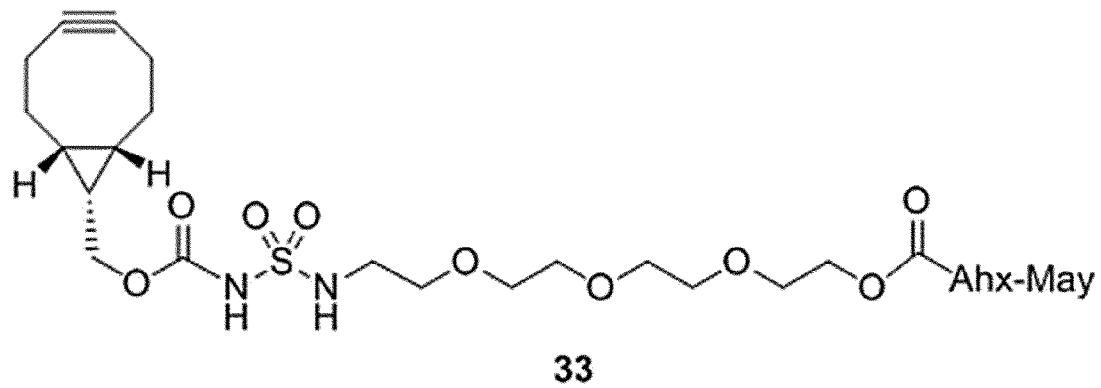
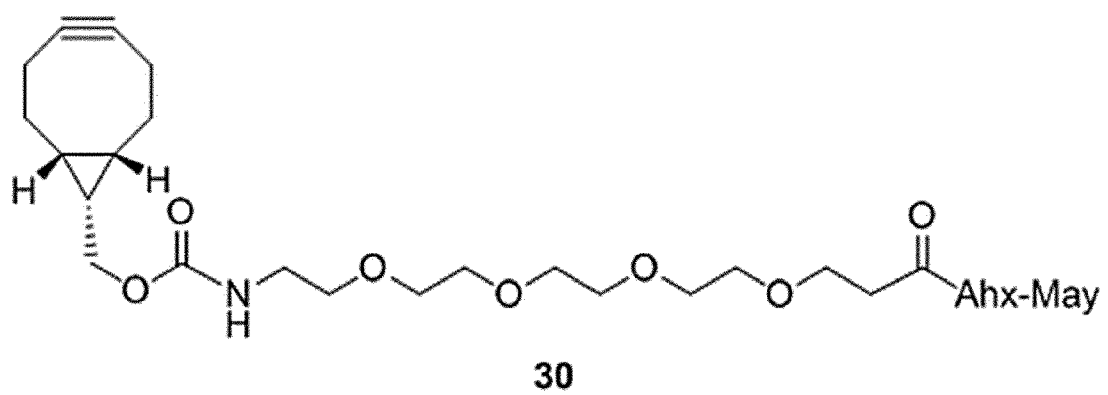
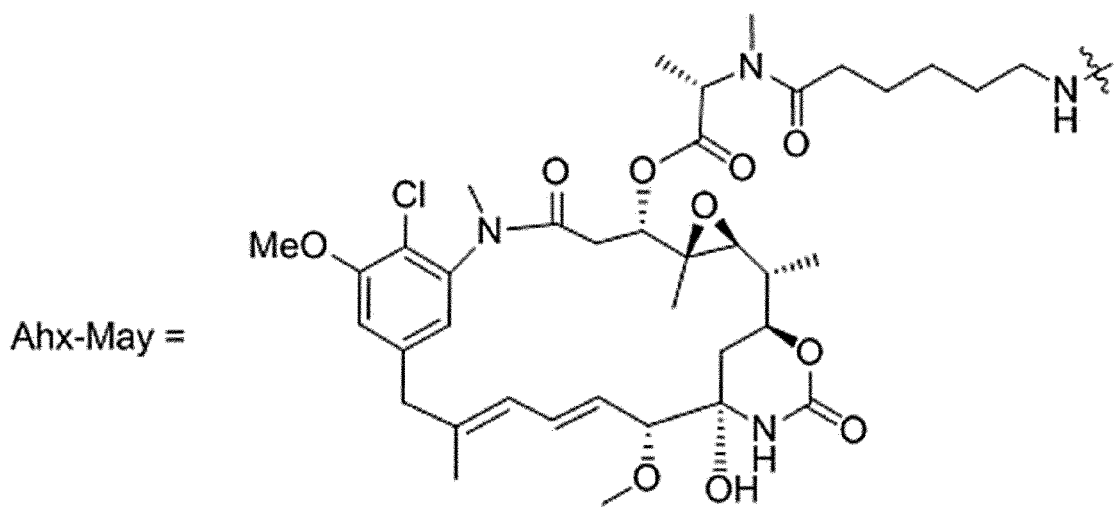

*Fig. 11*

| | F¹ | Q¹ | Z³ | |
|---|---|---|---|---|
| natural | -SH | maleimide (N-substituted) | succinimide-S- | 10a |
| | | allyl (CH₂=CH-CH₂-) | -S-CH₂CH₂- | 10b |
| | -NH₂ | X-C(O)- ; X = leaving group | -NH-C(O)- | 10c |
| engineered | -SH | maleimide (N-substituted) | succinimide-S- | 10a |
| | -C(O)CH₃ (ketone) | H₂N-Y- ; Y = O or NH | C=N-Y- | 10d |
| | -C≡CH (alkyne) | N₃- | 1,4-triazole | 10e |
| | -N₃ | -C≡CH | 1,4-triazole (regioisomer) | 10f |
| | | cyclooctyne | fused triazole-cyclooctane | 10g |
| | cyclopropene/strained alkene | tetrazine (Z-substituted); Z = H, Me, pyridyl | bicyclic pyrazoline adduct | 10h* |

*will eliminate N₂

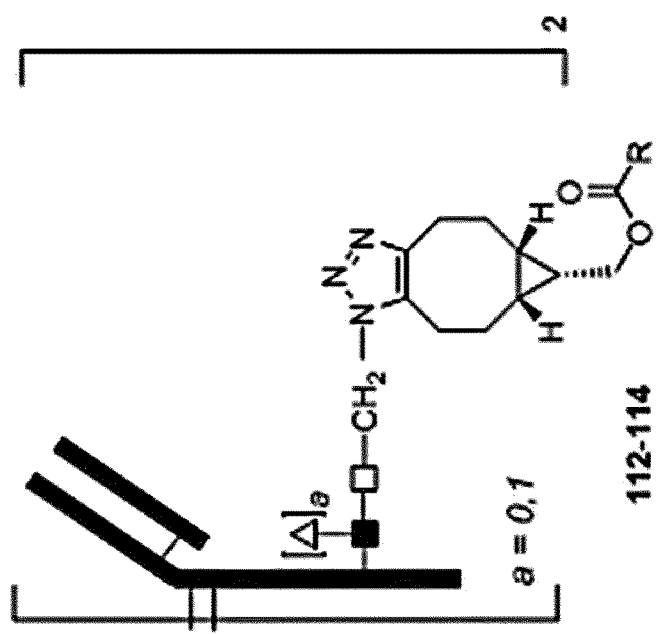
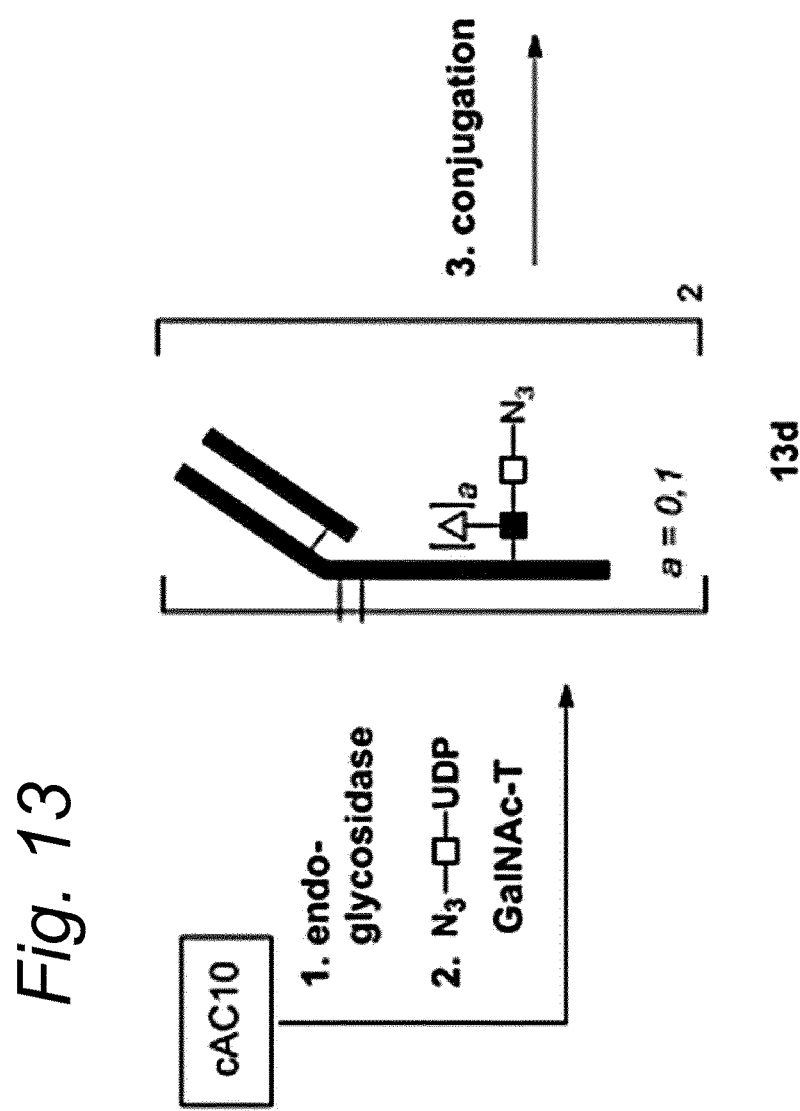
Fig. 13

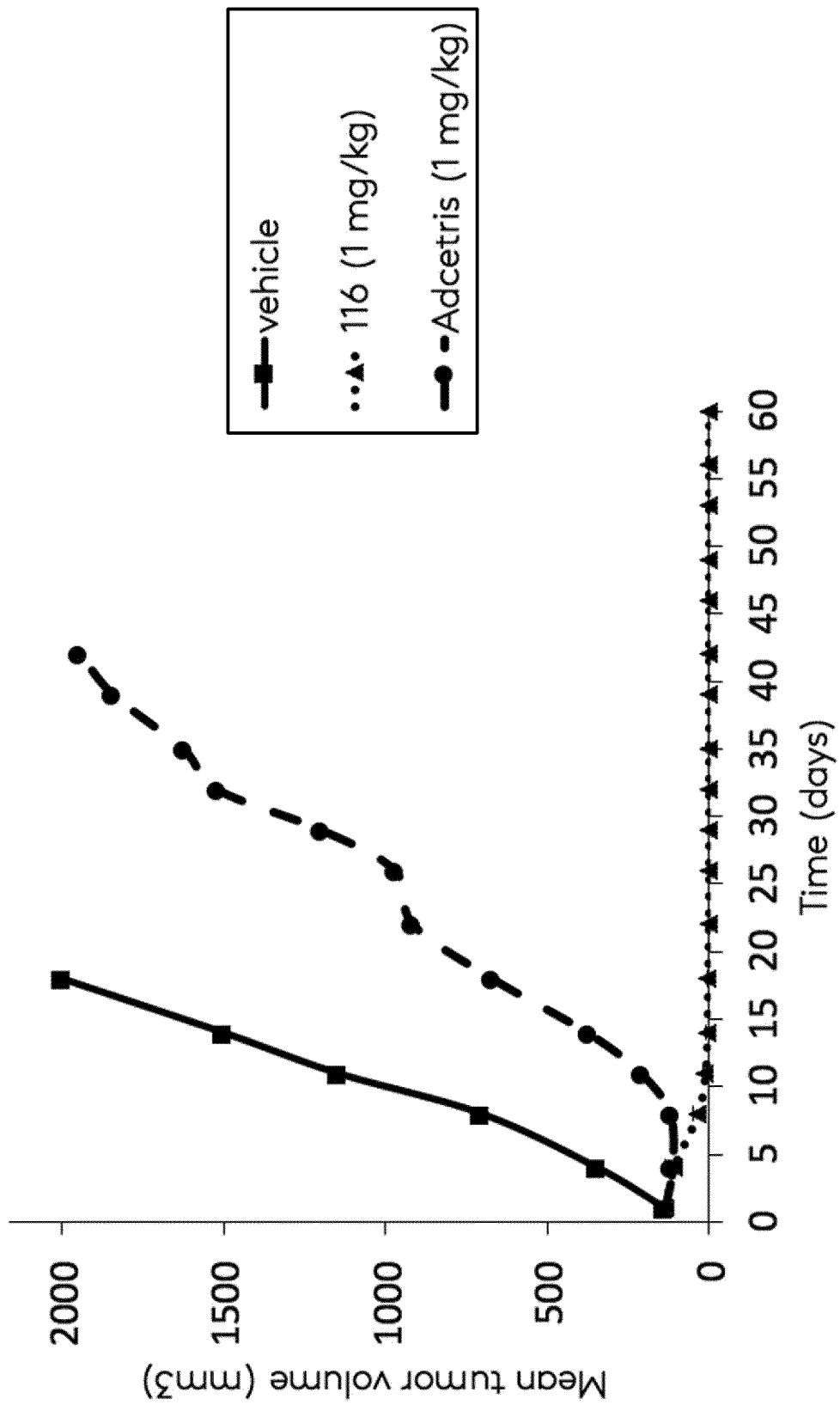

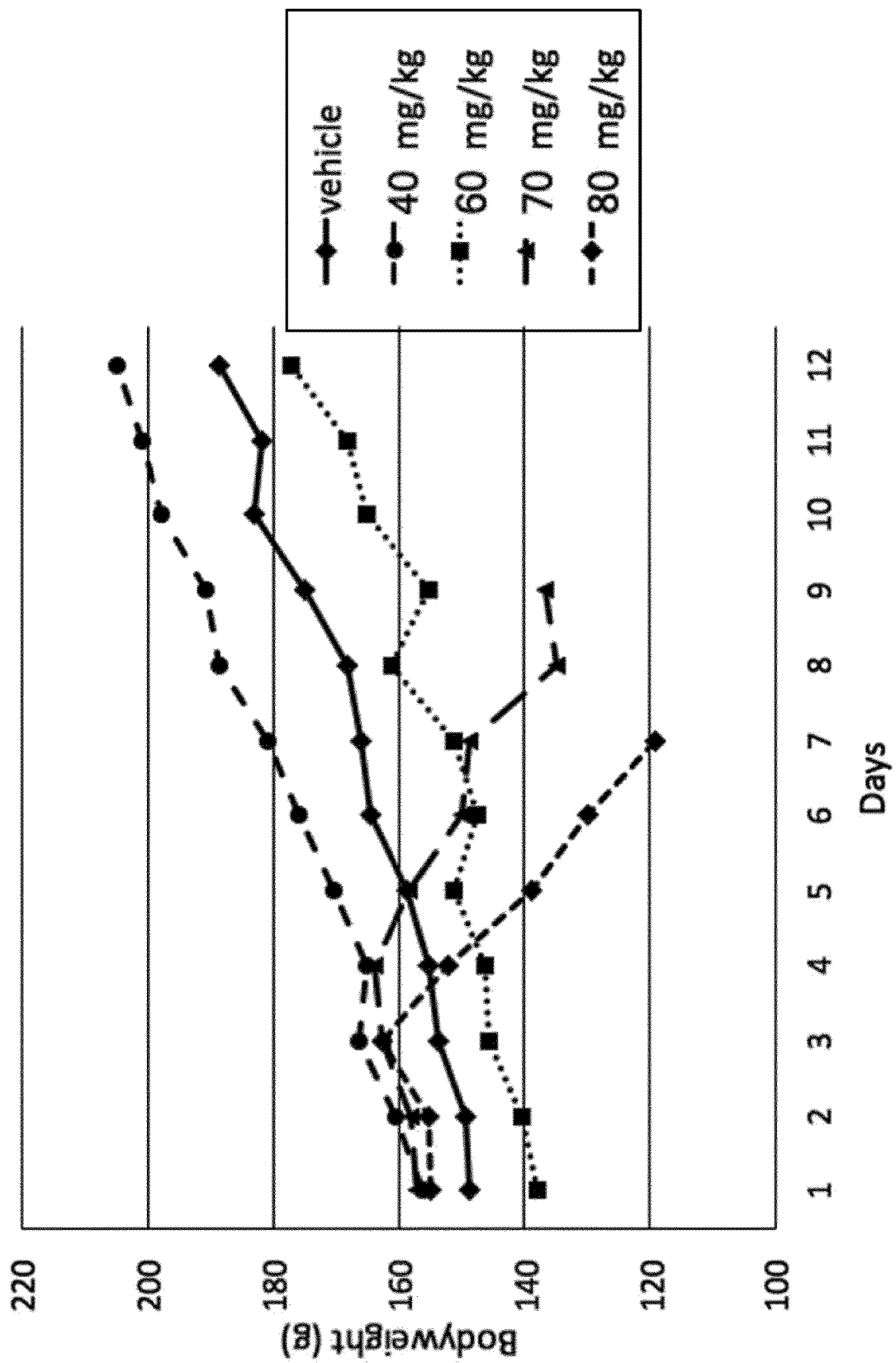

SEQUENCE LISTING

<160> NUMBER OF SEQ ID NOS: 2

<210> SEQ ID NO 1
<211> LENGTH: 1258
<212> TYPE: PRT
<213> ORGANISM: Artificial sequence
<220> FEATURE:
<223> OTHER INFORMATION: fusion protein EndoSH

<400> SEQUENCE: 1

```
Met Pro Ser Ile Asp Ser Leu His Tyr Leu Ser Glu Asn Ser Lys Lys
1               5                   10                  15

Glu Phe Lys Glu Glu Leu Ser Lys Ala Gly Gln Glu Ser Gln Lys Val
            20                  25                  30

Lys Glu Ile Leu Ala Lys Ala Gln Gln Ala Asp Lys Gln Ala Gln Glu
        35                  40                  45

Leu Ala Lys Met Lys Ile Pro Glu Lys Ile Pro Met Lys Pro Leu His
    50                  55                  60

Gly Pro Leu Tyr Gly Gly Tyr Phe Arg Thr Trp His Asp Lys Thr Ser
65                  70                  75                  80

Asp Pro Thr Glu Lys Asp Lys Val Asn Ser Met Gly Glu Leu Pro Lys
                85                  90                  95

Glu Val Asp Leu Ala Phe Ile Phe His Asp Trp Thr Lys Asp Tyr Ser
            100                 105                 110

Leu Phe Trp Lys Glu Leu Ala Thr Lys His Val Pro Lys Leu Asn Lys
        115                 120                 125

Gln Gly Thr Arg Val Ile Arg Thr Ile Pro Trp Arg Phe Leu Ala Gly
    130                 135                 140

Gly Asp Asn Ser Gly Ile Ala Glu Asp Thr Ser Lys Tyr Pro Asn Thr
145                 150                 155                 160

Pro Glu Gly Asn Lys Ala Leu Ala Lys Ala Ile Val Asp Glu Tyr Val
                165                 170                 175

Tyr Lys Tyr Asn Leu Asp Gly Leu Asp Val Asp Val Glu His Asp Ser
            180                 185                 190

Ile Pro Lys Val Asp Lys Lys Glu Asp Thr Ala Gly Val Glu Arg Ser
        195                 200                 205
```

-continued

```
Ile Gln Val Phe Glu Glu Ile Gly Lys Leu Ile Gly Pro Lys Gly Val
210                 215                 220

Asp Lys Ser Arg Leu Phe Ile Met Asp Ser Thr Tyr Met Ala Asp Lys
225                 230                 235                 240

Asn Pro Leu Ile Glu Arg Gly Ala Pro Tyr Ile Asn Leu Leu Leu Val
            245                 250                 255

Gln Val Tyr Gly Ser Gln Gly Glu Lys Gly Gly Trp Glu Pro Val Ser
            260                 265                 270

Asn Arg Pro Glu Lys Thr Met Glu Glu Arg Trp Gln Gly Tyr Ser Lys
        275                 280                 285

Tyr Ile Arg Pro Glu Gln Tyr Met Ile Gly Phe Ser Phe Tyr Glu Glu
    290                 295                 300

Asn Ala Gln Glu Gly Asn Leu Trp Tyr Asp Ile Asn Ser Arg Lys Asp
305                 310                 315                 320

Glu Asp Lys Ala Asn Gly Ile Asn Thr Asp Ile Thr Gly Thr Arg Ala
                325                 330                 335

Glu Arg Tyr Ala Arg Trp Gln Pro Lys Thr Gly Gly Val Lys Gly Gly
            340                 345                 350

Ile Phe Ser Tyr Ala Ile Asp Arg Asp Gly Val Ala His Gln Pro Lys
        355                 360                 365

Lys Tyr Ala Lys Gln Lys Glu Phe Lys Asp Ala Thr Asp Asn Ile Phe
    370                 375                 380

His Ser Asp Tyr Ser Val Ser Lys Ala Leu Lys Thr Val Met Leu Lys
385                 390                 395                 400

Asp Lys Ser Tyr Asp Leu Ile Asp Glu Lys Asp Phe Pro Asp Lys Ala
                405                 410                 415

Leu Arg Glu Ala Val Met Ala Gln Val Gly Thr Arg Lys Gly Asp Leu
            420                 425                 430

Glu Arg Phe Asn Gly Thr Leu Arg Leu Asp Asn Pro Ala Ile Gln Ser
        435                 440                 445

Leu Glu Gly Leu Asn Lys Phe Lys Lys Leu Ala Gln Leu Asp Leu Ile
    450                 455                 460

Gly Leu Ser Arg Ile Thr Lys Leu Asp Arg Ser Val Leu Pro Ala Asn
465                 470                 475                 480

Met Lys Pro Gly Lys Asp Thr Leu Glu Thr Val Leu Glu Thr Tyr Lys
                485                 490                 495

Lys Asp Asn Lys Glu Glu Pro Ala Thr Ile Pro Pro Val Ser Leu Lys
            500                 505                 510

Val Ser Gly Leu Thr Gly Leu Lys Glu Leu Asp Leu Ser Gly Phe Asp
        515                 520                 525

Arg Glu Thr Leu Ala Gly Leu Asp Ala Ala Thr Leu Thr Ser Leu Glu
    530                 535                 540

Lys Val Asp Ile Ser Gly Asn Lys Leu Asp Leu Ala Pro Gly Thr Glu
545                 550                 555                 560

Asn Arg Gln Ile Phe Asp Thr Met Leu Ser Thr Ile Ser Asn His Val
                565                 570                 575

Gly Ser Asn Glu Gln Thr Val Lys Phe Asp Lys Gln Pro Thr Gly
            580                 585                 590

His Tyr Pro Asp Thr Tyr Gly Lys Thr Ser Leu Arg Leu Pro Val Ala
        595                 600                 605

Asn Glu Lys Val Asp Leu Gln Ser Gln Leu Leu Phe Gly Thr Val Thr
    610                 615                 620
```

-continued

```
Asn Gln Gly Thr Leu Ile Asn Ser Glu Ala Asp Tyr Lys Ala Tyr Gln
625                 630                 635                 640

Asn His Lys Ile Ala Gly Arg Ser Phe Val Asp Ser Asn Tyr His Tyr
            645                 650                 655

Asn Asn Phe Lys Val Ser Tyr Glu Asn Tyr Thr Val Lys Val Thr Asp
                660                 665                 670

Ser Thr Leu Gly Thr Thr Thr Asp Lys Thr Leu Ala Thr Asp Lys Glu
            675                 680                 685

Glu Thr Tyr Lys Val Asp Phe Phe Ser Pro Ala Asp Lys Thr Lys Ala
            690                 695                 700

Val His Thr Ala Lys Val Ile Val Gly Asp Glu Lys Thr Met Met Val
705                 710                 715                 720

Asn Leu Ala Glu Gly Ala Thr Val Ile Gly Gly Ser Ala Asp Pro Val
                725                 730                 735

Asn Ala Arg Lys Val Phe Asp Gly Gln Leu Gly Ser Glu Thr Asp Asn
                740                 745                 750

Ile Ser Leu Gly Trp Asp Ser Lys Gln Ser Ile Ile Phe Lys Leu Lys
            755                 760                 765

Glu Asp Gly Leu Ile Lys His Trp Arg Phe Phe Asn Asp Ser Ala Arg
770                 775                 780

Asn Pro Glu Thr Thr Asn Lys Pro Ile Gln Glu Ala Ser Leu Gln Ile
785                 790                 795                 800

Phe Asn Ile Lys Asp Tyr Asn Leu Asp Asn Leu Leu Glu Asn Pro Asn
                805                 810                 815

Lys Phe Asp Asp Glu Lys Tyr Trp Ile Thr Val Asp Thr Tyr Ser Ala
            820                 825                 830

Gln Gly Glu Arg Ala Thr Ala Phe Ser Asn Thr Leu Asn Asn Ile Thr
            835                 840                 845

Ser Lys Tyr Trp Arg Val Val Phe Asp Thr Lys Gly Asp Arg Tyr Ser
850                 855                 860

Ser Pro Val Val Pro Glu Leu Gln Ile Leu Gly Tyr Pro Leu Pro Asn
865                 870                 875                 880

Ala Asp Thr Ile Met Lys Thr Val Thr Thr Ala Lys Glu Leu Ser Gln
            885                 890                 895

Gln Lys Asp Lys Phe Ser Gln Lys Met Leu Asp Glu Leu Lys Ile Lys
            900                 905                 910

Glu Met Ala Leu Glu Thr Ser Leu Asn Ser Lys Ile Phe Asp Val Thr
            915                 920                 925

Ala Ile Asn Ala Asn Ala Gly Val Leu Lys Asp Cys Ile Glu Lys Arg
930                 935                 940

Gln Leu Leu Lys Lys Gly Gly Gly Ser Gly Gly Gly Gly Ser Gly
945                 950                 955                 960

Gly Gly Ser His His His His His Glu Phe Gly Gly Gly
            965                 970                 975

Ser Gly Gly Gly Gly Ser Gly Gly Gly Ser Ala Pro Ala Pro Val
            980                 985                 990

Lys Gln Gly Pro Thr Ser Val Ala Tyr Val Glu Val Asn Asn Asn Ser
            995                 1000                1005

Met Leu Asn Val Gly Lys Tyr Thr Leu Ala Asp Gly Gly Gly Asn
    1010                1015                1020

Ala Phe Asp Val Ala Val Ile Phe Ala Ala Asn Ile Asn Tyr Asp
    1025                1030                1035
```

-continued

```
Thr Gly Thr Lys Thr Ala Tyr Leu His Phe Asn Glu Asn Val Gln
    1040                1045                1050

Arg Val Leu Asp Asn Ala Val Thr Gln Ile Arg Pro Leu Gln Gln
    1055                1060                1065

Gln Gly Ile Lys Val Leu Leu Ser Val Leu Gly Asn His Gln Gly
    1070                1075                1080

Ala Gly Phe Ala Asn Phe Pro Ser Gln Gln Ala Ala Ser Ala Phe
    1085                1090                1095

Ala Lys Gln Leu Ser Asp Ala Val Ala Lys Tyr Gly Leu Asp Gly
    1100                1105                1110

Val Asp Phe Asp Asp Glu Tyr Ala Glu Tyr Gly Asn Asn Gly Thr
    1115                1120                1125

Ala Gln Pro Asn Asp Ser Ser Phe Val His Leu Val Thr Ala Leu
    1130                1135                1140

Arg Ala Asn Met Pro Asp Lys Ile Ile Ser Leu Tyr Asn Ile Gly
    1145                1150                1155

Pro Ala Ala Ser Arg Leu Ser Tyr Gly Gly Val Asp Val Ser Asp
    1160                1165                1170

Lys Phe Asp Tyr Ala Trp Asn Pro Tyr Tyr Gly Thr Trp Gln Val
    1175                1180                1185

Pro Gly Ile Ala Leu Pro Lys Ala Gln Leu Ser Pro Ala Ala Val
    1190                1195                1200

Glu Ile Gly Arg Thr Ser Arg Ser Thr Val Ala Asp Leu Ala Arg
    1205                1210                1215

Arg Thr Val Asp Glu Gly Tyr Gly Val Tyr Leu Thr Tyr Asn Leu
    1220                1225                1230

Asp Gly Gly Asp Arg Thr Ala Asp Val Ser Ala Phe Thr Arg Glu
    1235                1240                1245

Leu Tyr Gly Ser Glu Ala Val Arg Thr Pro
    1250                1255

<210> SEQ ID NO 2
<211> LENGTH: 410
<212> TYPE: PRT
<213> ORGANISM: Artificial sequence
<220> FEATURE:
<223> OTHER INFORMATION: His-TnGalNAcT(33-421)

<400> SEQUENCE: 2

Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
        35                  40                  45

Asn Trp Pro Lys Lys Ile Pro Ser Asn Tyr Ile Glu Asp Ser Glu Glu
    50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
        115                 120                 125
```

```
Thr Glu Asp Gly Val Lys Lys Ala Glu Ala Val Val Thr Leu Pro Leu
130                 135                 140
Cys Asp Ser Met Pro Pro Asp Leu Gly Pro Ile Thr Leu Asn Lys Thr
145                 150                 155                 160
Glu Leu Glu Leu Glu Trp Val Glu Lys Lys Phe Pro Glu Val Glu Trp
                165                 170                 175
Gly Gly Arg Tyr Ser Pro Pro Asn Cys Thr Ala Arg His Arg Val Ala
                180                 185                 190
Ile Ile Val Pro Tyr Arg Asp Arg Gln Gln His Leu Ala Ile Phe Leu
                195                 200                 205
Asn His Met His Pro Phe Leu Met Lys Gln Gln Ile Glu Tyr Gly Ile
210                 215                 220
Phe Ile Val Glu Gln Glu Gly Asn Lys Asp Phe Asn Arg Ala Lys Leu
225                 230                 235                 240
Met Asn Val Gly Phe Val Glu Ser Gln Lys Leu Val Ala Glu Gly Trp
                245                 250                 255
Gln Cys Phe Val Phe His Asp Ile Asp Leu Leu Pro Leu Asp Thr Arg
                260                 265                 270
Asn Leu Tyr Ser Cys Pro Arg Gln Pro Arg His Met Ser Ala Ser Ile
                275                 280                 285
Asp Lys Leu His Phe Lys Leu Pro Tyr Glu Asp Ile Phe Gly Gly Val
290                 295                 300
Ser Ala Met Thr Leu Glu Gln Phe Thr Arg Val Asn Gly Phe Ser Asn
305                 310                 315                 320
Lys Tyr Trp Gly Trp Gly Gly Glu Asp Asp Asp Met Ser Tyr Arg Leu
                325                 330                 335
Lys Lys Ile Asn Tyr His Ile Ala Arg Tyr Lys Met Ser Ile Ala Arg
                340                 345                 350
Tyr Ala Met Leu Asp His Lys Lys Ser Thr Pro Asn Pro Lys Arg Tyr
                355                 360                 365
Gln Leu Leu Ser Gln Thr Ser Lys Thr Phe Gln Lys Asp Gly Leu Ser
    370                 375                 380
Thr Leu Glu Tyr Glu Leu Val Gln Val Val Gln Tyr His Leu Tyr Thr
385                 390                 395                 400
His Ile Leu Val Asn Ile Asp Glu Arg Ser
                405                 410
```

BIOCONJUGATES CONTAINING SULFAMIDE LINKERS FOR USE IN TREATMENT

CROSS-REFERENCE TO RELATED APPLICATIONS

This present application is a 371 U.S. National Application of International Application No. PCT/EP2017/052788, entitled "BIOCONJUGATES CONTAINING SULFAMIDE LINKERS FOR USE IN TREATMENT," filed Feb. 8, 2017; which claims the benefit of and priority to European Application No. 16154712.0, filed Feb. 8, 2016, European Application No. 16154739.3, filed Feb. 8, 2016, European Application No. 16173595.6, filed Jun. 8, 2016, and European Application No. 16173599.8, filed Jun. 8, 2016, all of which are incorporated herein by reference in their entireties.

SEQUENCE LISTING

The instant application contains a Sequence Listing which has been submitted in ASCII format via EFS-WEB and is hereby incorporated by reference in its entirety. Said ASCII copy, created on Aug. 7, 2018, is named 069818_3930_Sequence_listing.txt and is 15 KB.

TECHNICAL FIELD OF THE INVENTION

The present invention is in the field of bioconjugation. The invention relates to sulfamide linkers and conjugates thereof, and to methods for the preparation thereof. More particularly, the invention relates to linkers comprising an acylsulfamide group and/or a carbamoyl sulfamide group and to conjugates comprising said linkers. The invention further relates to a process for the preparation of bioconjugates comprising a linker, the linker comprising an acylsulfamide group and/or a carbamoyl sulfamide group.

BACKGROUND OF THE INVENTION

Bioconjugation is the process of linking two or more molecules, of which at least one is a biomolecule. The biomolecule(s) may also be referred to as "biomolecule(s) of interest", the other molecule(s) may also be referred to as "target molecule" or "molecule of interest". Typically the biomolecule of interest (BOI) will consist of a protein (or peptide), a glycan, a nucleic acid (or oligonucleotide), a lipid, a hormone or a natural drug (or fragments or combinations thereof). The other molecule of interest (MOI) may also be a biomolecule, hence leading to the formation of homo- or heterodimers (or higher oligomers), or the other molecule may possess specific features that are imparted onto the biomolecule of interest by the conjugation process. For example, the modulation of protein structure and function by covalent modification with a chemical probe for detection and/or isolation has evolved as a powerful tool in proteome-based research and biomedical applications. Fluorescent or affinity tagging of proteins is key to studying the trafficking of proteins in their native habitat. Vaccines based on protein-carbohydrate conjugates have gained prominence in the fight against HIV, cancer, malaria and pathogenic bacteria, whereas carbohydrates immobilized on microarrays are instrumental in elucidation of the glycome. Synthetic DNA and RNA oligonucleotides (ONs) require the introduction of a suitable functionality for diagnostic and therapeutic applications, such as microarray technology, antisense and gene-silencing therapies, nanotechnology and various materials sciences applications. For example, attachment of a cell-penetrating ligand is the most commonly applied strategy to tackle the low internalization rate of ONs encountered during oligonucleotide-based therapeutics (antisense, siRNA). Similarly, the preparation of oligonucleotide-based microarrays requires the selective immobilization of ONs on a suitable solid surface, e.g. glass.

There are numerous examples of chemical reactions suitable to covalently link two (or more) molecular structures. However, labelling of biomolecules poses high restrictions on the reaction conditions that can be applied (solvent, concentration, temperature), while the desire of chemoselective labelling limits the choice of reactive groups. For obvious reasons, biological systems generally flourish best in an aqueous environment meaning that reagents for bioconjugation should be suitable for application in aqueous systems. In general, two strategic concepts can be recognized in the field of bioconjugation technology: (a) conjugation based on a functional group already present in the biomolecule of interest, such as for example a thiol, an amine, an alcohol or a hydroxyphenol unit or (b) a two-stage process involving engineering of one (or more) unique reactive groups into a BOI prior to the actual conjugation process.

The first approach typically involves a reactive amino acid side-chain in a protein (e.g. cysteine, lysine, serine and tyrosine), or a functional group in a glycan (e.g. amine, aldehyde) or nucleic acid (e.g. purine or pyrimidine functionality or alcohol). As summarized inter alia in G. T. Hermanson, "*Bioconjugate Techniques*", Elsevier, $3^{rd}$ Ed. 2013, incorporated by reference, a large number of reactive functional groups have become available over the years for chemoselective targeting of one of these functional groups, such as maleimide, haloacetamide, activated ester, activated carbonate, sulfonyl halide, activated thiol derivative, alkene, alkyne, allenamide and more, each of which requiring its own specific conditions for conjugation (pH, concentration, stoichiometry, light, etc.). Most prominently, cysteine-maleimide conjugation stands out for protein conjugation by virtue of its high reaction rate and chemoselectivity. However, when no cysteine is available for conjugation, as in many proteins and certainly in other biomolecules, other methods are often required, each suffering from its own shortcomings.

An elegant and broadly applicable solution for bioconjugation involves the two-stage approach. Although more laborious, two-stage conjugation via engineered functionality typically leads to higher selectivity (site-specificity) than conjugation on a natural functionality. Besides that, full stability can be achieved by proper choice of construct, which can be an important shortcoming of one stage conjugation on native functionality, in particular for cysteine-maleimide conjugation. Typical examples of a functional group that may be imparted onto the BOI include (strained) alkyne, (strained) alkene, norbornene, tetrazine, azide, phosphine, nitrile oxide, nitrone, nitrile imine, diazo compound, carbonyl compound, (O-alkyl)hydroxylamine and hydrazine, which may be achieved by either chemical or molecular biology approach. Each of the above functional groups is known to have at least one reaction partner, in many cases involving complete mutual reactivity. For example, cyclooctynes react selectively and exclusively with 1,3-dipoles, strained alkenes with tetrazines and phosphines with azides, leading to fully stable covalent bonds. However, some of the above functional groups have the disadvantage of being highly lipophilic, which may compromise conjugation efficiency, in particular in combination with a lipophilic molecule of interest (see below). The final linking unit between the biomolecule and the other molecule of interest should preferentially also be fully compatible with an aqueous environment in terms of solubility, stability and biocompatibility. For example, a highly lipophilic linker may lead to aggregation (during and/or after conjugation), which may significantly increase reaction times and/or reduce conjugation yields, in particular when the MOI is also of hydrophobic nature. Similarly, highly lipophilic linker-MOI combination may lead to unspecific binding to surfaces or specific hydrophobic patches on the same or other biomolecules. If the linker is susceptible to aqueous hydrolysis or other water-induced cleavage reactions, the components comprising the original bioconjugate separate by diffusion. For example, certain ester moieties are not suitable due to saponification while 3-hydroxycarbonyl or γ-dicarbonyl compounds could lead to retro-aldol or retro-Michael reaction, respectively. Finally, the linker should be inert to functionalities present in the bioconjugate or any other functionality that may be encountered during application of the bioconjugate, which excludes, amongst others, the use of linkers featuring for example a ketone or aldehyde moiety (may lead to imine formation), an α,β-unsaturated carbonyl compound (Michael addition), thioesters or other activated esters (amide bond formation).

Compounds made of linear oligomers of ethylene glycol, so-called polyethylene glycol (PEG) linkers, enjoy particular popularity nowadays in biomolecular conjugation processes. PEG linkers are highly water soluble, non-toxic, non-antigenic, and lead to negligible or no aggregation. For this reason, a large variety of linear, bifunctional PEG linkers are commercially available from various sources, which can be selectively modified at either end with a (bio)molecule of interest. PEG linkers are the product of a polymerization process of ethylene oxide and are therefore typically obtained as stochastic mixtures of chain length, which can be partly resolved into PEG constructs with an average weight distribution centred around 1, 2, 4 kDa or more (up to 60 kDa). Homogeneous, discrete PEGs (dPEGs) are also known with molecular weights up to 4 kDa and branched versions thereof go up to 15 kDa. Interestingly, the PEG unit itself imparts particular characteristics onto a biomolecule. In particular, protein PEGylation may lead to prolonged residence in vivo, decreased degradation by metabolic enzymes and a reduction or elimination of protein immunogenicity. Several PEGylated proteins have been FDA-approved and are currently on the market.

By virtue of its high polarity, PEG linkers are perfectly suitable for bioconjugation of small and/or water-soluble moieties under aqueous conditions. However, in case of conjugation of hydrophobic, non-water-soluble molecules of interest, the polarity of a PEG unit may be insufficient to offset hydrophobicity, leading to significantly reduced reaction rates, lower yields and induced aggregation issues. In such case, lengthy PEG linkers and/or significant amounts of organic co-solvents may be required to solubilize the reagents. For example, in the field of antibody-drug conjugates, the controlled attachment of a distinct number of toxic payloads to a monoclonal antibody is key, with a payload typically selected from the group of auristatins E or F, maytansinoids, duocarmycins, calicheamicins or pyrrolobenzodiazepines (PBDs), with many others are underway. With the exception of auristatin F, all toxic payloads are poorly to non-water-soluble, which necessitates organic co-solvents to achieve successful conjugation, such as 25% dimethylacetamide (DMA) or 50% propylene glycol (PG). In case of hydrophobic payloads, despite the use of aforementioned co-solvents, large stoichiometries of reagents may be required during conjugation while efficiency and yield may be significantly compromised due to aggregation (in process or after product isolation), as for example described by Senter et al. in *Nat. Biotechn.* 2014, 24, 1256-1263, incorporated by reference. The use of long PEG spacers (12 units or more) may partially enhance solubility and/or conjugation efficiency, but it has been shown that long PEG spacers may lead to more rapid in vivo clearance, and hence negatively influence the pharmacokinetic profile of the ADC.

Using conventional linkers (e.g. PEG), effective conjugation is often hampered by the relatively low solubility of the linker-conjugate in aqueous media, especially when a relative water-insoluble or hydrophobic target molecule is used. In their quest for a short, polar spacer that enables fast and efficient conjugation of hydrophobic moieties, the inventors have developed the sulfamide linker, which was found to improve the solubility of the linker-conjugate, which in turn significantly improves the efficiency of the conjugation and reduces both in process and product aggregation. This is disclosed in patent application PCT/NL2015/050697 (WO 2016/053107), which is incorporated herein in its entirety.

Linkers are known in the art, and disclosed in e.g. WO 2008/070291, incorporated by reference. WO 2008/070291 discloses a linker for the coupling of targeting agents to anchoring components. The linker contains hydrophilic regions represented by polyethylene glycol (PEG) and an extension lacking chiral centres that is coupled to a targeting agent.

WO 01/88535, incorporated by reference, discloses a linker system for surfaces for bioconjugation, in particular a linker system having a novel hydrophilic spacer group. The hydrophilic atoms or groups for use in the linker system are selected from the group consisting of O, NH, C=O (keto group), O—C=O (ester group) and $CR^3R^4$, wherein $R^3$ and $R^4$ are independently selected from the group consisting of H, OH, $C_1$-$C_4$ alkoxy and $C_1$-$C_4$ acyloxy.

WO 2014/100762, incorporated by reference, describes compounds with a hydrophilic self-immolative linker, which is cleavable under appropriate conditions and incorporates a hydrophilic group to provide better solubility of the compound. The compounds comprise a drug moiety, a targeting moiety capable of targeting a selected cell population, and a linker which contains an acyl unit, an optional spacer unit for providing distance between the drug moiety and the targeting moiety, a peptide linker which can be cleavable under appropriate conditions, a hydrophilic self-immolative linker, and an optional second self-immolative spacer or cyclization self-elimination linker. The hydrophilic self-immolative linker is e.g. a benzyloxycarbonyl group.

SUMMARY OF THE INVENTION

The invention relates to a method for increasing the therapeutic index of a bioconjugate, the conjugate of a biomolecule and a target molecule. The inventors surprisingly found that a bioconjugate prepared such that it contains a linker L comprising a group according to formula (1) or a salt thereof:

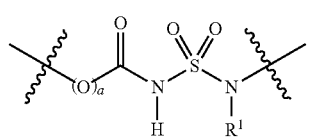

exhibits a greater therapeutic index compared to the same bioconjugate, i.e. the same biomolecule, the same target molecule (e.g. active substance) and the same biomolecule drug ratio, containing a linker without the group according to formula (1) present. That the linker could have an effect on the therapeutic index of a bioconjugate, such as an antibody-drug-conjugate, could not be envisioned based on the current knowledge. In the field, linkers are considered inert when it comes to treatment and are solely present as a consequence of the preparation of the bioconjugate. That the selection of a specific linker has an effect on the therapeutic index is unprecedented and a breakthrough discovery in the field of bioconjugates, in particular antibody-drug-conjugates.

The bioconjugates according to the invention are on one hand more efficacious (therapeutically effective) as the same bioconjugates, i.e. the same biomolecule, the same target molecule (e.g. active substance) and the same biomolecule/target molecule ratio, containing a different linker, and on the other hand exhibit a greater tolerability. This finding has dramatic implications on the treatment of subjects with the bioconjugate according to the invention, as the therapeutic window widens. As a result of the expansion of the therapeutic window, the treatment dosages may be lowered and as a consequence potential, unwanted, side-effects are reduced.

The bioconjugate according to the invention is represented by formula (A):

$$B\text{-}L\text{-}D \qquad (A),$$

wherein:
B is a biomolecule;
L is a linker linking B and D;
D is a target molecule; and
each occurrence of "—" is independently a bond or a spacer moiety.

In group according to formula (1),
a is 0 or 1; and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a further target molecule D, wherein D is optionally connected to N via a spacer moiety.

The present invention thus concerns in a first aspect a method for increasing the therapeutic index of a bioconjugate, comprising the step of preparing the bioconjugate of formula (A) such that linker L as defined above is comprised in the bioconjugate. In one embodiment, the method according to the invention further comprises administering the bioconjugate to a subject in need thereof. The invention according to the first aspect can also be worded as the use of a linker L as defined above in a bioconjugate for increasing the therapeutic index of the bioconjugate.

In a further aspect, the present invention concerns the treatment of a subject in need thereof, comprising the administration of the bioconjugate according to the invention. Typically, the bioconjugate is administered in a therapeutically effective dose. In view of the increased therapeutic efficacy, administration may occur less frequent as in treatment with conventional bioconjugates and/or in a lower dose. Alternatively, in view of the increased tolerability, administration may occur more frequent as in treatment with conventional bioconjugates and/or in a higher dose. Administration may be in a single dose or may e.g. occur 1-4 times a month, preferably 1-2 times a month, more preferable administration occurs once every 3 or 4 weeks, most preferably every 4 weeks. As will be appreciated by the person skilled in the art, the dose of the bioconjugate according to the invention may depend on many factors and optimal doses can be determined by the skilled person via routine experimentation. The bioconjugate is typically administered in a dose of 0.01-50 mg/kg body weight of the subject, more accurately 0.1-25 mg/kg or most accurately 0.5-10 mg/kg. In one embodiment, the administration of the bioconjugate according to the invention is at a dose that is lower than the $TD_{50}$ of the same bioconjugate but not comprising the linker according to the invention, preferably the dose is at most 99-90%, more preferably at most 89-60%, even more preferable 59-30%, most preferably at most 29-10% of the $TD_{50}$ of the same bioconjugate but not comprising the linker according to the invention. Alternatively, the administration of the bioconjugate according to the invention is at a dose that is higher than the $TD_{50}$ of the same bioconjugate but not comprising the linker according to the invention, preferably the dose is at most 10-29%, more preferably at most 30-59%, even more preferable 60-89%, most preferably at most 90-99% of the $TD_{50}$ of the same bioconjugate but not comprising the linker according to the invention.

The preparation of the bioconjugate typically comprises the step of reacting linker-conjugate having the formula $Q^1$-L-D, wherein L and D are as defined above and $Q^1$ is a reactive group capable of reacting with a functional group F, with a biomolecule having the formula B—$F^1$, wherein B is as defined above and $F^1$ is a functional group capable of reacting with $Q^1$. Herein, $Q^1$ and $F^1$ react to form a connecting group $Z^3$, which is located in the bioconjugate according to formula (A) in the spacer moiety between B and L.

DESCRIPTION OF DRAWINGS

FIG. 1 describes the general concept of conjugation of biomolecules: a biomolecule of interest (BOI) containing one or more functional groups $F^1$ is incubated with (excess of) a target molecule D (also referred to as molecule of interest or MOI) covalently attached to a reactive group $Q^1$ via a specific linker. In the process of bioconjugation, a chemical reaction between $F^1$ and $Q^1$ takes place, thereby forming a bioconjugate comprising a covalent connection between the BOI and the MOI. The BOI may e.g. be a peptide/protein, a glycan or a nucleic acid.

FIG. 2 shows several structures of derivatives of UDP sugars of galactosamine, which may be modified with e.g. a 3-mercaptopropionyl group (11a), an azidoacetyl group (11b), or an azidodifluoroacetyl group (11c) at the 2-position, or with an azido azidoacetyl group at the 6-position of N-acetyl galactosamine (11d).

FIG. 5 shows the structures of several compounds wherein an N-maleimidyl reactive group $Q^1$ is connected to a pyrene group (D) via a prior art linker unit 17 or a linker unit 18 according to the invention.

FIG. 6 shows the structures of several compounds wherein a bicyclo[6.1.0]non-4-yn-9-yl] reactive group $Q^1$ (also referred to as a BCN group) is connected to benzylamine (D) via a prior art linker unit (19, 22) or a linker unit according to the invention (20, 21, 23).

FIG. 8 shows the structures of linker-conjugates 30 and 33, wherein a bicyclo[6.1.0]non-4-yn-9-yl] reactive group $Q^1$ (also referred to as a BCN group) is connected to maytansin via a linker unit. Linker-conjugate 33 is according to the invention, while linker-conjugate 30 is not. These two linker-conjugates, conjugated to trastuzumab (i.e. ADCs 97 and 98), have been used in the efficacy and safety studies of examples 29 and 31.

FIG. 11 shows a representative set of functional groups ($F^1$) in a biomolecule, either naturally present or introduced by engineering, which upon reaction with reactive group $Q^1$ lead to connecting group $Z^3$. Functional group $F^1$ may also be artificially introduced (engineered) into a biomolecule at any position of choice. The same functional groups and reactive moieties are suitably used as $F^2$ and $Q^2$, respectively. Connecting group $Z^3$ may also be the result of a reaction between $F^2$ and $Q^2$.

FIG. 13 depicts the preparation of antibody-drug-conjugates 112-114, prepared in Examples 26-28 and used in Example 30. For 112: R=—NH—(CH$_2$CH$_2$O)$_4$—C(O)-Val-Cit-MMAE (prepared by conjugation of 13d with 111); For 113: R=—NH—S(O)$_2$—NH—(CH$_2$CH$_2$O)$_2$—C(O)-Val-Cit-MMAE (prepared by conjugation of 13d with 100); For 114: R=—NH—(CH$_2$)$_3$—C(O)—NH—S(O)$_2$—NM-(CH$_2$CH$_2$O)$_2$—C(O)-Val-Cit-MMAE (prepared by conjugation of 13d with 108).

FIG. 16 shows the safety results of Example 31 for bioconjugates 97, containing a linker according to the invention, and 98, containing a prior art PEG-linker.

FIGS. 17a and 17b depict the results of Example 49, wherein the mean tumour volume (in mm$^3$) is depicted over time for a bioconjugate according to the invention (116, FIG. 17b) and the same bioconjugate having a linker outside the scope of the resent invention (115, FIG. 17a). FIGS. 17a and 17b represent mean tumour volumes as measured in two separate in vivo efficacy studies, in each study with Adcetris as a positive control. The difference in effect of Adcetris on the tumour growth delay in the different studies can be rationalized by the difference in doubling time of the cells (as becomes apparent in the tumour size of the group treated with vehicle).

FIG. 18a shows the mean body weight of the groups treated with 112 at 80, 120, 140 or 160 mg/kg. FIG. 18b shows the mean body weight of the groups treated with 113 at 80, 120, 140 or 160 mg/kg. FIG. 18c shows the mean body weight of the groups treated with 114 at 80, 120, 140 or 160 mg/kg. Based on these results, MTDs are established to be 120 mg/kg for each of 112-114.

FIG. 19a-c show the safety results of Example 51, wherein rats were treated with Adcetris, 115 or 116 (all DAR4 ADCs with same antibody brentuximab and payload MMAE). FIG. 19a shows the mean body weight of the groups treated with Adcetris at 15, 20 or 40 mg/kg. FIG. 19b shows the mean body weight of the groups treated with 115 at 40, 60, 70 or 80 mg/kg. FIG. 19c shows the mean body weight of the groups treated with 116 at 40, 60, 70 or 80 mg/kg. Based on these results, MTDs are established as 15 mg/kg for Adcetris (reported 18 mg/kg) and 60 mg/kg for both 115 and 116.

DETAILED DESCRIPTION OF THE INVENTION

Figure 3:
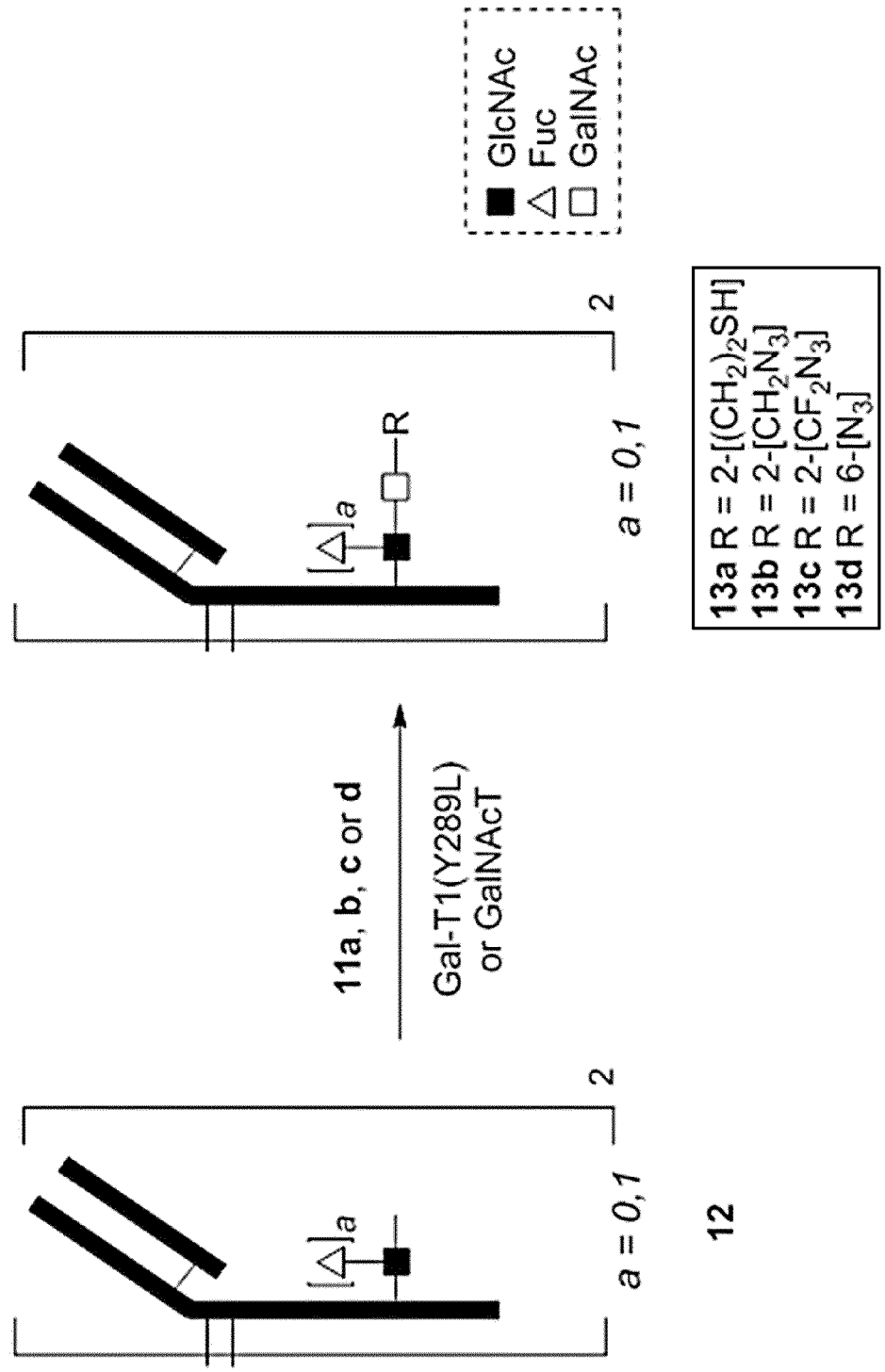
FIG. 3 schematically displays how any of the UDP-sugars 11a-d may be attached to a glycoprotein comprising a GlcNAc moiety 12 (e.g. a monoclonal antibody the glycan of which is trimmed by an endoglycosidase) under the action of a galactosyltransferase mutant or a GalNAc-transferase, thereby generating a 3-glycosidic 1-4 linkage between a GalNAc derivative and GlcNAc (compounds 13a-d, respectively).

In the context of the present invention, the conjugation reaction involves on the one hand the biomolecule (BOI) containing a functional group $F^1$, and on the other hand the target molecule (MOI) containing a reactive group $Q^1$, or a "linker-conjugate" as defined herein, wherein $Q^1$ reacts with $F^1$ to form a connecting group that joins the BOI and the MOI in a bioconjugate. Herein, reactive group $Q^1$ is joined via a linker to the MOI, said linker comprising the sulfamide moiety according to formula (1).

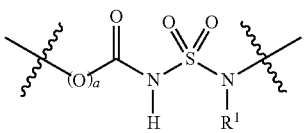

Reactive group $Q^1$ may be attached to either ends of the moiety of formula (1), in which case the MOI is attached to the opposite end of the moiety of formula (1). In one embodiment, reactive group $Q^1$ is attached to the moiety of formula (1) via the carbonyl end and the MOI is attached via the sulfamide end of the moiety of formula (1). In one embodiment, reactive group $Q^1$ is attached to the moiety of formula (1) via the sulfamide end and the MOI is attached via the carbonyl end of the moiety of formula (1).

Definitions

The verb "to comprise", and its conjugations, as used in this description and in the claims is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one".

The compounds disclosed in this description and in the claims may comprise one or more asymmetric centres, and different diastereomers and/or enantiomers may exist of the compounds. The description of any compound in this description and in the claims is meant to include all diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer.

The compounds may occur in different tautomeric forms. The compounds according to the invention are meant to include all tautomeric forms, unless stated otherwise. When the structure of a compound is depicted as a specific tautomer, it is to be understood that the invention of the present application is not limited to that specific tautomer.

The compounds disclosed in this description and in the claims may further exist as exo and endo diastereoisomers. Unless stated otherwise, the description of any compound in the description and in the claims is meant to include both the individual exo and the individual endo diastereoisomers of a compound, as well as mixtures thereof. When the structure of a compound is depicted as a specific endo or exo diastereomer, it is to be understood that the invention of the present application is not limited to that specific endo or exo diastereomer.

Furthermore, the compounds disclosed in this description and in the claims may exist as cis and trans isomers. Unless stated otherwise, the description of any compound in the description and in the claims is meant to include both the individual cis and the individual trans isomer of a compound, as well as mixtures thereof. As an example, when the structure of a compound is depicted as a cis isomer, it is to be understood that the corresponding trans isomer or mixtures of the cis and trans isomer are not excluded from the invention of the present application. When the structure of a compound is depicted as a specific cis or trans isomer, it is to be understood that the invention of the present application is not limited to that specific cis or trans isomer.

Unsubstituted alkyl groups have the general formula $C_nH_{2n+1}$ and may be linear or branched.

Optionally, the alkyl groups are substituted by one or more substituents further specified in this document. Examples of alkyl groups include methyl, ethyl, propyl, 2-propyl, t-butyl, 1-hexyl, 1-dodecyl, etc.

A cycloalkyl group is a cyclic alkyl group. Unsubstituted cycloalkyl groups comprise at least three carbon atoms and have the general formula $C_nH_{2n-1}$. Optionally, the cycloalkyl groups are substituted by one or more substituents further specified in this document. Examples of cycloalkyl groups include cyclopropyl, cyclobutyl, cyclopentyl and cyclohexyl.

An alkenyl group comprises one or more carbon-carbon double bonds, and may be linear or branched. Unsubstituted alkenyl groups comprising one C—C double bond have the general formula $C_nH_{2n-1}$. Unsubstituted alkenyl groups comprising two C—C double bonds have the general formula $C_nH_{2n-3}$. An alkenyl group may comprise a terminal carbon-carbon double bond and/or an internal carbon-carbon double bond. A terminal alkenyl group is an alkenyl group wherein a carbon-carbon double bond is located at a terminal position of a carbon chain. An alkenyl group may also comprise two or more carbon-carbon double bonds. Examples of an alkenyl group include ethenyl, propenyl, isopropenyl, t-butenyl, 1,3-butadienyl, 1,3-pentadienyl, etc. Unless stated otherwise, an alkenyl group may optionally be substituted with one or more, independently selected, substituents as defined below. Unless stated otherwise, an alkenyl group may optionally be interrupted by one or more heteroatoms independently selected from the group consisting of O, N and S.

An alkynyl group comprises one or more carbon-carbon triple bonds, and may be linear or branched. Unsubstituted alkynyl groups comprising one C—C triple bond have the general formula $C_nH_{2n-3}$. An alkynyl group may comprise a terminal carbon-carbon triple bond and/or an internal carbon-carbon triple bond. A terminal alkynyl group is an alkynyl group wherein a carbon-carbon triple bond is located at a terminal position of a carbon chain. An alkynyl group may also comprise two or more carbon-carbon triple bonds. Unless stated otherwise, an alkynyl group may optionally be substituted with one or more, independently selected, substituents as defined below. Examples of an alkynyl group include ethynyl, propynyl, isopropynyl, t-butynyl, etc. Unless stated otherwise, an alkynyl group may optionally be interrupted by one or more heteroatoms independently selected from the group consisting of O, N and S.

An aryl group comprises six to twelve carbon atoms and may include monocyclic and bicyclic structures. Optionally, the aryl group may be substituted by one or more substituents further specified in this document. Examples of aryl groups are phenyl and naphthyl.

Arylalkyl groups and alkylaryl groups comprise at least seven carbon atoms and may include monocyclic and bicyclic structures. Optionally, the arylalkyl groups and alkylaryl may be substituted by one or more substituents further specified in this document. An arylalkyl group is for example benzyl. An alkylaryl group is for example 4-t-butylphenyl.

Heteroaryl groups comprise at least two carbon atoms (i.e. at least $C_2$) and one or more heteroatoms N, O, P or S. A heteroaryl group may have a monocyclic or a bicyclic structure.

Optionally, the heteroaryl group may be substituted by one or more substituents further specified in this document. Examples of suitable heteroaryl groups include pyridinyl, quinolinyl, pyrimidinyl, pyrazinyl, pyrazolyl, imidazolyl, thiazolyl, pyrrolyl, furanyl, triazolyl, benzofuranyl, indolyl, purinyl, benzoxazolyl, thienyl, phospholyl and oxazolyl.

Heteroarylalkyl groups and alkylheteroaryl groups comprise at least three carbon atoms (i.e. at least $C_3$) and may include monocyclic and bicyclic structures. Optionally, the heteroaryl groups may be substituted by one or more substituents further specified in this document.

Where an aryl group is denoted as a (hetero)aryl group, the notation is meant to include an aryl group and a heteroaryl group. Similarly, an alkyl(hetero)aryl group is meant to include an alkylaryl group and a alkylheteroaryl group, and (hetero)arylalkyl is meant to include an arylalkyl group and a heteroarylalkyl group. A $C_2$-$C_{24}$ (hetero)aryl group is thus to be interpreted as including a $C_2$-$C_{24}$ heteroaryl group and a $C_6$-$C_{24}$ aryl group. Similarly, a $C_3$-$C_{24}$ alkyl(hetero)aryl group is meant to include a $C_7$-$C_{24}$ alkylaryl group and a $C_3$-$C_{24}$ alkylheteroaryl group, and a $C_3$-$C_{24}$ (hetero)arylalkyl is meant to include a $C_7$-$C_{24}$ arylalkyl group and a $C_3$-$C_{24}$ heteroarylalkyl group.

A cycloalkynyl group is a cyclic alkynyl group. An unsubstituted cycloalkynyl group comprising one triple bond has the general formula $C_nH_{2n-5}$. Optionally, a cycloalkynyl group is substituted by one or more substituents further specified in this document. An example of a cycloalkynyl group is cyclooctynyl.

A heterocycloalkynyl group is a cycloalkynyl group interrupted by heteroatoms selected from the group of oxygen, nitrogen and sulfur. Optionally, a heterocycloalkynyl group is substituted by one or more substituents further specified in this document. An example of a heterocycloalkynyl group is azacyclooctynyl.

A (hetero)aryl group comprises an aryl group and a heteroaryl group. An alkyl(hetero)aryl group comprises an alkylaryl group and an alkylheteroaryl group. A (hetero) arylalkyl group comprises a arylalkyl group and a heteroarylalkyl groups. A (hetero)alkynyl group comprises an alkynyl group and a heteroalkynyl group. A (hetero)cycloalkynyl group comprises an cycloalkynyl group and a heterocycloalkynyl group.

A (hetero)cycloalkyne compound is herein defined as a compound comprising a (hetero)cycloalkynyl group.

Several of the compounds disclosed in this description and in the claims may be described as fused (hetero) cycloalkyne compounds, i.e. (hetero)cycloalkyne compounds wherein a second ring structure is fused, i.e. annulated, to the (hetero)cycloalkynyl group. For example in a fused (hetero)cyclooctyne compound, a cycloalkyl (e.g. a cyclopropyl) or an arene (e.g. benzene) may be annulated to the (hetero)cyclooctynyl group. The triple bond of the (hetero)cyclooctynyl group in a fused (hetero)cyclooctyne compound may be located on either one of the three possible locations, i.e. on the 2, 3 or 4 position of the cyclooctyne moiety (numbering according to "IUPAC Nomenclature of Organic Chemistry", Rule A31.2). The description of any fused (hetero)cyclooctyne compound in this description and in the claims is meant to include all three individual regioisomers of the cyclooctyne moiety.

Unless stated otherwise, alkyl groups, cycloalkyl groups, alkenyl groups, alkynyl groups, (hetero)aryl groups, (hetero) arylalkyl groups, alkyl(hetero)aryl groups, alkylene groups, alkenylene groups, alkynylene groups, cycloalkylene groups, cycloalkenylene groups, cycloalkynylene groups, (hetero)arylene groups, alkyl(hetero)arylene groups, (hetero)arylalkylene groups, (hetero)arylalkenylene groups, (hetero)arylalkynylene groups, alkenyl groups, alkoxy groups, alkenyloxy groups, (hetero)aryloxy groups, alkynyloxy groups and cycloalkyloxy groups may be substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo and silyl groups, wherein the silyl groups can be represented by the formula $(R^{20})_3Si-$, wherein $R^{20}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S.

The general term "sugar" is herein used to indicate a monosaccharide, for example glucose (Glc), galactose (Gal), mannose (Man) and fucose (Fuc). The term "sugar derivative" is herein used to indicate a derivative of a monosaccharide sugar, i.e. a monosaccharide sugar comprising substituents and/or functional groups. Examples of a sugar derivative include amino sugars and sugar acids, e.g. glucosamine ($GlcNH_2$), galactosamine ($GalNH_2$)N-acetylglucosamine (GlcNAc), N-acetylgalactosamine (GalNAc), sialic acid (Sia) which is also referred to as N-acetylneuraminic acid (NeuNAc), and N-acetylmuramic acid (MurNAc), glucuronic acid (GlcA) and iduronic acid (IdoA).

The term "nucleotide" is herein used in its normal scientific meaning. The term "nucleotide" refers to a molecule that is composed of a nucleobase, a five-carbon sugar (either ribose or 2-deoxyribose), and one, two or three phosphate groups. Without the phosphate group, the nucleobase and sugar compose a nucleoside. A nucleotide can thus also be called a nucleoside monophosphate, a nucleoside diphosphate or a nucleoside triphosphate. The nucleobase may be adenine, guanine, cytosine, uracil or thymine. Examples of a nucleotide include uridine diphosphate (UDP), guanosine diphosphate (GDP), thymidine diphosphate (TDP), cytidine diphosphate (CDP) and cytidine monophosphate (CMP).

The term "protein" is herein used in its normal scientific meaning. Herein, polypeptides comprising about 10 or more amino acids are considered proteins. A protein may comprise natural, but also unnatural amino acids.

The term "glycoprotein" is herein used in its normal scientific meaning and refers to a protein comprising one or more monosaccharide or oligosaccharide chains ("glycans") covalently bonded to the protein. A glycan may be attached to a hydroxyl group on the protein (O-linked-glycan), e.g. to the hydroxyl group of serine, threonine, tyrosine, hydroxylysine or hydroxyproline, or to an amide function on the protein (N-glycoprotein), e.g. asparagine or arginine, or to a carbon on the protein (C-glycoprotein), e.g. tryptophan. A glycoprotein may comprise more than one glycan, may comprise a combination of one or more monosaccharide and one or more oligosaccharide glycans, and may comprise a combination of N-linked, O-linked and C-linked glycans. It is estimated that more than 50% of all proteins have some form of glycosylation and therefore qualify as glycoprotein. Examples of glycoproteins include PSMA (prostate-specific membrane antigen), CAL (candida antartica lipase), gp41, gp120, EPO (erythropoietin), antifreeze protein and antibodies.

The term "glycan" is herein used in its normal scientific meaning and refers to a monosaccharide or oligosaccharide chain that is linked to a protein. The term glycan thus refers to the carbohydrate-part of a glycoprotein. The glycan is attached to a protein via the C-1 carbon of one sugar, which may be without further substitution (monosaccharide) or may be further substituted at one or more of its hydroxyl groups (oligosaccharide). A naturally occurring glycan typically comprises 1 to about 10 saccharide moieties. However, when a longer saccharide chain is linked to a protein, said saccharide chain is herein also considered a glycan. A glycan of a glycoprotein may be a monosaccharide. Typically, a monosaccharide glycan of a glycoprotein consists of a single N-acetylglucosamine (GlcNAc), glucose (Glc), mannose (Man) or fucose (Fuc) covalently attached to the protein. A glycan may also be an oligosaccharide. An oligosaccharide chain of a glycoprotein may be linear or branched. In an oligosaccharide, the sugar that is directly attached to the protein is called the core sugar. In an oligosaccharide, a sugar that is not directly attached to the protein and is attached to at least two other sugars is called an internal sugar. In an oligosaccharide, a sugar that is not directly attached to the protein but to a single other sugar, i.e. carrying no further sugar substituents at one or more of its other hydroxyl groups, is called the terminal sugar. For the avoidance of doubt, there may exist multiple terminal sugars in an oligosaccharide of a glycoprotein, but only one core sugar. A glycan may be an O-linked glycan, an N-linked glycan or a C-linked glycan. In an O-linked glycan a monosaccharide or oligosaccharide glycan is bonded to an O-atom in an amino acid of the protein, typically via a hydroxyl group of serine (Ser) or threonine (Thr). In an N-linked glycan a monosaccharide or oligosaccharide glycan is bonded to the protein via an N-atom in an amino acid of the protein, typically via an amide nitrogen in the side chain of asparagine (Asn) or arginine (Arg). In a C-linked glycan a monosaccharide or oligosaccharide glycan is bonded to a C-atom in an amino acid of the protein, typically to a C-atom of tryptophan (Trp).

The term "antibody" is herein used in its normal scientific meaning. An antibody is a protein generated by the immune system that is capable of recognizing and binding to a specific antigen. An antibody is an example of a glycoprotein. The term antibody herein is used in its broadest sense and specifically includes monoclonal antibodies, polyclonal antibodies, dimers, multimers, multispecific antibodies (e.g. bispecific antibodies), antibody fragments, and double and single chain antibodies. The term "antibody" is herein also meant to include human antibodies, humanized antibodies, chimeric antibodies and antibodies specifically binding cancer antigen. The term "antibody" is meant to include whole antibodies, but also antigen-binding fragments of an antibody, for example an antibody Fab fragment, F(ab')$_2$, Fv fragment or Fc fragment from a cleaved antibody, a scFv-Fc fragment, a minibody, a diabody or a scFv. Furthermore, the term includes genetically engineered antibodies and derivatives of an antibody. Antibodies, fragments of antibodies and genetically engineered antibodies may be obtained by methods that are known in the art. Typical examples of antibodies include, amongst others, abciximab, rituximab, basiliximab, palivizumab, infliximab, trastuzumab, alemtuzumab, adalimumab, tositumomab-1131, cetuximab, ibrituximab tiuxetan, omalizumab, bevacizumab, natalizumab, ranibizumab, panitumumab, eculizumab, certolizumab pegol, golimumab, canakinumab, catumaxomab, ustekinumab, tocilizumab, ofatumumab, denosumab, belimumab, ipilimumab and brentuximab.

A linker is herein defined as a moiety that connects two or more elements of a compound. For example in a bioconjugate, a biomolecule and a target molecule are covalently connected to each other via a linker; in the linker-conjugate a reactive group $Q^1$ is covalently connected to a target molecule via a linker; in a linker-construct a reactive group $Q^1$ is covalently connected to a reactive group $Q^2$ via a linker. A linker may comprise one or more spacer-moieties.

A spacer-moiety is herein defined as a moiety that spaces (i.e. provides distance between) and covalently links together two (or more) parts of a linker. The linker may be part of e.g. a linker-construct, the linker-conjugate or a bioconjugate, as defined below.

A linker-construct is herein defined as a compound wherein a reactive group $Q^1$ is covalently connected to a reactive group $Q^2$ via a linker. A linker-construct comprises a reactive group $Q^1$ capable of reacting with a reactive group present on a biomolecule, and a reactive group $Q^2$ capable of reacting with a reactive group present on a target molecule. $Q^1$ and $Q^2$ may be the same, or different. A linker-construct may also comprise more than one reactive group $Q^1$ and/or more than one reactive group $Q^2$. A linker-construct may also be denoted as $Q^1$-Sp-$Q^2$, wherein $Q^1$ is a reactive group capable of reacting with a reactive group $F^1$ present on a biomolecule, $Q^2$ is a reactive group capable of reacting with a reactive group $F^2$ present on a target molecule and Sp is a spacer moiety. When a linker-construct comprises more than one reactive group $Q^1$ and/or more than one reactive group $Q^2$, the linker-construct may be denoted as $(Q^1)_y$-Sp-$(Q^2)_z$, wherein y is an integer in the range of 1 to 10 and z is an integer in the range of 1 to 10. Preferably, y is 1, 2, 3 or 4, more preferably y is 1 or 2 and most preferably, y is 1. Preferably, z is 1, 2, 3, 4, 5 or 6, more preferably z is 1, 2, 3 or 4, even more preferably z is 1, 2 or 3, yet even more preferably z is 1 or 2 and most preferably z is 1. More preferably, y is 1 or 2, preferably 1, and z is 1, 2, 3 or 4, yet even more preferably y is 1 or 2, preferably 1, and z is 1, 2 or 3, yet even more preferably y is 1 or 2, preferably 1, and z is 1 or 2, and most preferably y is 1 and z is 1.

A bioconjugate is herein defined as a compound wherein a biomolecule is covalently connected to a target molecule via a linker. A bioconjugate comprises one or more biomolecules and/or one or more target molecules. The linker may comprise one or more spacer moieties.

When a compound is herein referred to as a compound comprising an alpha-end and an omega-end, said compound comprises two (or more) ends, the first end being referred to as the alpha-end and the second end being referred to as the omega-end. Said compound may comprise more than two ends, i.e. a third, fourth etc. end may be present in the compound.

A biomolecule is herein defined as any molecule that can be isolated from nature or any molecule composed of smaller molecular building blocks that are the constituents of macromolecular structures derived from nature, in particular nucleic acids, proteins, glycans and lipids. Examples of a biomolecule include an enzyme, a (non-catalytic) protein, a polypeptide, a peptide, an amino acid, an oligonucleotide, a monosaccharide, an oligosaccharide, a polysaccharide, a glycan, a lipid and a hormone.

A target molecule, also referred to as a molecule of interest (MOI), is herein defined as molecular structure possessing a desired property that is imparted onto the biomolecule upon conjugation.

The term "salt thereof" means a compound formed when an acidic proton, typically a proton of an acid, is replaced by a cation, such as a metal cation or an organic cation and the like. Where applicable, the salt is a pharmaceutically acceptable salt, although this is not required for salts that are not intended for administration to a patient. For example, in a salt of a compound the compound may be protonated by an inorganic or organic acid to form a cation, with the conjugate base of the inorganic or organic acid as the anionic component of the salt.

The term "pharmaceutically accepted" salt means a salt that is acceptable for administration to a patient, such as a mammal (salts with counter-ions having acceptable mammalian safety for a given dosage regime). Such salts may be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions known in the art and include, for example, sodium, potassium, calcium, magnesium, ammonium, tetraalkylammonium, etc., and when the molecule contains a basic functionality, salts of organic or inorganic acids, such as hydrochloride, hydrobromide, formate, tartrate, besylate, mesylate, acetate, maleate, oxalate, etc.

Herein, a sulfamide linker and conjugates of said sulfamide linker are disclosed. The term "sulfamide linker" refers to a linker comprising a sulfamide group, more particularly an acylsulfamide group [—C(O)—N(H)—S(O)$_2$—N(R$^1$)—] and/or a carbamoyl sulfamide group [—O—C(O)—N(H)—S(O)$_2$—N(R$^1$)—].

Herein, the term "therapeutic index" (TI) has the conventional meaning well known to a person skilled in the art, and refers to the ratio of the dose of drug that is toxic (i.e. causes adverse effects at an incidence or severity not compatible with the targeted indication) for 50% of the population (TD$_{50}$) divided by the dose that leads to the desired pharmacological effect in 50% of the population (effective dose or ED$_{50}$). Hence, TI=TD$_{50}$/ED$_{50}$. The therapeutic index may be determined by clinical trials or for example by plasma exposure tests. See also Muller, et al. *Nature Reviews Drug Discovery* 2012, 11, 751-761. At an early development stage, the clinical TI of a drug candidate is often not yet known. However, understanding the preliminary TI of a drug candidate is of utmost importance as early as possible, since TI is an important indicator of the probability of the successful development of a drug. Recognizing drug candidates with potentially suboptimal TI at earliest possible stage helps to initiate mitigation or potentially re-deploy resources. At this early stage, TI is typically defined as the quantitative ratio between safety (maximum tolerated dose in mouse or rat) and efficacy (minimal effective dose in a mouse xenograft).

Herein, the term "therapeutic efficacy" denotes the capacity of a substance to achieve a certain therapeutic effect, e.g. reduction in tumour volume. Therapeutic effects can be measured determining the extent in which a substance can achieve the desired effect, typically in comparison with another substance under the same circumstances. A suitable measure for the therapeutic efficacy is the ED$_{50}$ value, which may for example be determined during clinical trials or by plasma exposure tests. In case of preclinical therapeutic efficacy determination, the therapeutic effect of a bioconjugate (e.g. an ADC), can be validated by patient-derived tumour xenografts in mice in which case the efficacy refers to the ability of the ADC to provide a beneficial effect. Alternatively the tolerability of said ADC in a rodent safety study can also be a measure of the therapeutic effect.

Herein, the term "tolerability" refers to the maximum dose of a specific substance that does not cause adverse effects at an incidence or severity not compatible with the targeted indication. A suitable measure for the tolerability for a specific substance is the TD$_{50}$ value, which may for example be determined during clinical trials or by plasma exposure tests.

Linker

The bioconjugate according to the invention contains a linker L linking the biomolecule B and the target molecule D. The linker comprises a group according to formula (1) or a salt thereof:

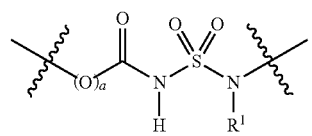

1 wherein:
a is 0 or 1; and
R$^1$ is selected from the group consisting of hydrogen, C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups, the C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups optionally substituted and optionally interrupted by one or more heteroatoms selected from O, S and NR$^3$ wherein R$^3$ is independently selected from the group consisting of hydrogen and C$_1$-C$_4$ alkyl groups, or R$^1$ is a further target molecule D, wherein D is optionally connected to N via a spacer moiety.

When the group of formula (1) comprises a salt, the salt is preferably a pharmaceutically acceptable salt.

In a preferred embodiment, linker L according to the invention comprises a group according to formula (1) wherein a is 0, or a salt thereof. In this embodiment, linker L thus comprises a group according to formula (2) or a salt thereof:

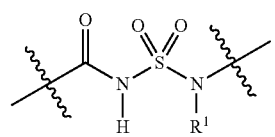

2 wherein R$^1$ is as defined above.

In another preferred embodiment, linker L according to the invention comprises a group according to formula (1) wherein a is 1, or a salt thereof. In this embodiment, linker L thus comprises a group according to formula (3) or a salt thereof:

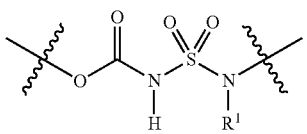

wherein $R^1$ is as defined above.

In the groups according to formula (1), (2) and (3), $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero) arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a further target molecule D, wherein D is optionally connected to N via a spacer moiety.

In a preferred embodiment, $R^1$ is hydrogen or a $C_1$-$C_{20}$ alkyl group, more preferably $R^1$ is hydrogen or a $C_1$-$C_{16}$ alkyl group, even more preferably $R^1$ is hydrogen or a $C_1$-$C_{10}$ alkyl group, wherein the alkyl group is optionally substituted and optionally interrupted by one or more heteroatoms selected from O, S and $NR^3$, preferably O, wherein $R^3$ is independently selected from the group consisting of hydrogen and $C_1$-$C_4$ alkyl groups. In a preferred embodiment, $R^1$ is hydrogen. In another preferred embodiment, $R^1$ is a $C_1$-$C_{20}$ alkyl group, more preferably a $C_1$-$C_{16}$ alkyl group, even more preferably a $C_1$-$C_{10}$ alkyl group, wherein the alkyl group is optionally interrupted by one or more O-atoms, and wherein the alkyl group is optionally substituted with an —OH group, preferably a terminal —OH group. In this embodiment it is further preferred that $R^1$ is a (poly)ethyleneglycol chain comprising a terminal —OH group. In another preferred embodiment, $R^1$ is selected from the group consisting of hydrogen, methyl, ethyl, n-propyl, i-propyl, n-butyl, s-butyl and t-butyl, more preferably from the group consisting of hydrogen, methyl, ethyl, n-propyl and i-propyl, and even more preferably from the group consisting of hydrogen, methyl and ethyl. Yet even more preferably $R^1$ is hydrogen or methyl, and most preferably $R^1$ is hydrogen.

In another preferred embodiment, $R^1$ is a further target molecule D. Optionally, D is connected to N via one or more spacer-moieties. The spacer-moiety, if present, is defined as a moiety that spaces, i.e. provides a certain distance between, and covalently links D and N.

Target molecules in the field of bioconjugation are known to the skilled person, and may also be referred to as payload. Target molecule D may be selected from the group consisting of an active substance, a reporter molecule, a polymer, a solid surface, a hydrogel, a nanoparticle, a microparticle and a biomolecule.

In the context of D, the term "active substance" relates to a pharmacological and/or biological substance, i.e. a substance that is biologically and/or pharmaceutically active, for example a drug, a prodrug, a diagnostic agent, a protein, a peptide, a polypeptide, a peptide tag, an amino acid, a glycan, a lipid, a vitamin, a steroid, a nucleotide, a nucleoside, a polynucleotide, RNA or DNA. Examples of peptide tags include cell-penetrating peptides like human lactoferrin or polyarginine. An example of a glycan is oligomannose. An example of an amino acid is lysine.

When the target molecule is an active substance, the active substance is preferably selected from the group consisting of drugs and prodrugs. More preferably, the active substance is selected from the group consisting of pharmaceutically active compounds, in particular low to medium molecular weight compounds (e.g. about 200 to about 2500 Da, preferably about 300 to about 1750 Da). In a further preferred embodiment, the active substance is selected from the group consisting of cytotoxins, antiviral agents, antibacterials agents, peptides and oligonucleotides. Examples of cytotoxins include colchicine, vinca alkaloids, anthracyclines, camptothecins, doxorubicin, daunorubicin, taxanes, calicheamycins, tubulysins, irinotecans, an inhibitory peptide, amanitin, deBouganin, duocarmycins, maytansines, auristatins or pyrrolobenzodiazepines (PBDs). In view of their poor water solubility, preferred active substances include vinca alkaloids, anthracyclines, camptothecins, taxanes, tubulysins, amanitin, duocarmycins, maytansines, auristatins and pyrrolobenzodiazepines, in particular vinca alkaloids, anthracyclines, camptothecins, taxanes, tubulysins, amanitin, maytansines and auristatins.

The term "reporter molecule" herein refers to a molecule whose presence is readily detected, for example a diagnostic agent, a dye, a fluorophore, a radioactive isotope label, a contrast agent, a magnetic resonance imaging agent or a mass label.

A wide variety of fluorophores, also referred to as fluorescent probes, is known to a person skilled in the art. Several fluorophores are described in more detail in e.g. G. T. Hermanson, "Bioconjugate Techniques", Elsevier, $3^{rd}$ Ed. 2013, Chapter 10: "Fluorescent probes", p. 395-463, incorporated by reference. Examples of a fluorophore include all kinds of Alexa Fluor (e.g. Alexa Fluor 555), cyanine dyes (e.g. Cy3 or Cy5) and cyanine dye derivatives, coumarin derivatives, fluorescein and fluorescein derivatives, rhodamine and rhodamine derivatives, boron dipyrromethene derivatives, pyrene derivatives, naphthalimide derivatives, phycobiliprotein derivatives (e.g. allophycocyanin), chromomycin, lanthanide chelates and quantum dot nanocrystals. In view of their poor water solubility, preferred fluorophores include cyanine dyes, coumarin derivatives, fluorescein and derivatives thereof, pyrene derivatives, naphthalimide derivatives, chromomycin, lanthanide chelates and quantum dot nanocrystals, in particular coumarin derivatives, fluorescein, pyrene derivatives and chromomycin.

Examples of a radioactive isotope label include $^{99m}$Tc, $^{111}$In, $^{14m}$In, $^{115}$In, $^{18}$F, $^{14}$C, $^{64}$Cu, $^{131}$I, $^{125}$I, $^{123}$I $^{212}$Bi, $^{88}$Y, $^{90}$Y, $^{67}$Cu, $^{186}$Rh, $^{188}$Rh, $^{66}$Ga, $^{67}$Ga and $^{10}$B, which is optionally connected via a chelating moiety such as e.g. DTPA (diethylenetriaminepentaacetic anhydride), DOTA (1,4,7,10-tetraazacyclododecane-N,N',N'',N'''tetraacetic acid), NOTA (1,4,7-triazacyclononane N,N',N''-triacetic acid), TETA (1,4,8,11-tetraazacyclotetradecane-N,N'N'', N'''tetraacetic acid), DTTA ($N^1$-(p-isothiocyanatobenzyl)-diethylenetriamine-$N^1$, $N^2$,$N^3$,$N^3$-tetraacetic acid), deferoxamine or DFA ($N^1$-[5-[[4-[[5-(acetylhydroxyamino)pentyl] amino]-1,4-dioxobutyl]hydroxyamino]pentyl]-N-(5-aminopentyl)-N-hydroxybutanediamide) or HYNIC (hydrazinonicotinamide). Isotopic labelling techniques are known to a person skilled in the art, and are described in more detail in e.g. G. T. Hermanson, "Bioconjugate Techniques", Elsevier, $3^{rd}$ Ed. 2013, Chapter 12: "Isotopic labelling techniques", p. 507-534, incorporated by reference.

Polymers suitable for use as a target molecule D in the compound according to the invention are known to a person skilled in the art, and several examples are described in more detail in e.g. G. T. Hermanson, "*Bioconjugate Techniques*", Elsevier, 3$^{rd}$ Ed. 2013, Chapter 18: "*PEGylation and synthetic polymer modification*", p. 787-838, incorporated by reference. When target molecule D is a polymer, target molecule D is preferably independently selected from the group consisting of a polyethylene glycol (PEG), a polyethylene oxide (PEO), a polypropylene glycol (PPG), a polypropylene oxide (PPO), a 1,x-diaminoalkane polymer (wherein x is the number of carbon atoms in the alkane, and preferably x is an integer in the range of 2 to 200, preferably 2 to 10), a (poly)ethylene glycol diamine (e.g. 1,8-diamino-3,6-dioxaoctane and equivalents comprising longer ethylene glycol chains), a polysaccharide (e.g. dextran), a poly(amino acid) (e.g. a poly(L-lysine)) and a poly(vinyl alcohol). In view of their poor water solubility, preferred polymers include a 1,x-diaminoalkane polymer and poly(vinyl alcohol).

Solid surfaces suitable for use as a target molecule D are known to a person skilled in the art. A solid surface is for example a functional surface (e.g. a surface of a nanomaterial, a carbon nanotube, a fullerene or a virus capsid), a metal surface (e.g. a titanium, gold, silver, copper, nickel, tin, rhodium or zinc surface), a metal alloy surface (wherein the alloy is from e.g. aluminium, bismuth, chromium, cobalt, copper, gallium, gold, indium, iron, lead, magnesium, mercury, nickel, potassium, plutonium, rhodium, scandium, silver, sodium, titanium, tin, uranium, zinc and/or zirconium), a polymer surface (wherein the polymer is e.g. polystyrene, polyvinylchloride, polyethylene, polypropylene, poly(dimethylsiloxane) or polymethylmethacrylate, polyacrylamide), a glass surface, a silicone surface, a chromatography support surface (wherein the chromatography support is e.g. a silica support, an agarose support, a cellulose support or an alumina support), etc. When target molecule D is a solid surface, it is preferred that D is independently selected from the group consisting of a functional surface or a polymer surface.

Hydrogels are known to the person skilled in the art. Hydrogels are water-swollen networks, formed by crosslinks between the polymeric constituents. See for example A. S. Hoffman, Adv. Drug Delivery Rev. 2012, 64, 18, incorporated by reference. When the target molecule is a hydrogel, it is preferred that the hydrogel is composed of poly(ethylene)glycol (PEG) as the polymeric basis. Micro- and nanoparticles suitable for use as a target molecule D are known to a person skilled in the art. A variety of suitable micro- and nanoparticles is described in e.g. G. T. Hermanson, "*Bioconjugate Techniques*", Elsevier, 3$^{rd}$ Ed. 2013, Chapter 14: "*Microparticles and nanoparticles*", p. 549-587, incorporated by reference. The micro- or nanoparticles may be of any shape, e.g. spheres, rods, tubes, cubes, triangles and cones. Preferably, the micro- or nanoparticles are of a spherical shape. The chemical composition of the micro- and nanoparticles may vary. When target molecule D is a micro- or a nanoparticle, the micro- or nanoparticle is for example a polymeric micro- or nanoparticle, a silica micro- or nanoparticle or a gold micro- or nanoparticle. When the particle is a polymeric micro- or nanoparticle, the polymer is preferably polystyrene or a copolymer of styrene (e.g. a copolymer of styrene and divinylbenzene, butadiene, acrylate and/or vinyltoluene), polymethylmethacrylate (PMMA), polyvinyltoluene, poly(hydroxyethyl methacrylate (pHEMA) or polyethylene glycol dimethacrylate/2-hydroxyethyl methacrylate) [poly(EDGMA/HEMA)]. Optionally, the surface of the micro- or nanoparticles is modified, e.g. with detergents, by graft polymerization of secondary polymers or by covalent attachment of another polymer or of spacer moieties, etc.

Target molecule D may also be a biomolecule. Biomolecules, and preferred embodiments thereof, are described in more detail below. When target molecule D is a biomolecule, it is preferred that the biomolecule is selected from the group consisting of proteins (including glycoproteins and antibodies), polypeptides, peptides, glycans, lipids, nucleic acids, oligonucleotides, polysaccharides, oligosaccharides, enzymes, hormones, amino acids and monosaccharides.

To obtain the bioconjugate of formula (A), the group of formula (1) can be introduced in one of three options. First of all, the linker L comprising the group according to formula (1) or a salt thereof may be present in the linker-conjugate represented by $Q^1$-D, wherein L is the spacer between $Q^1$ and D. Secondly, the linker L comprising the group according to formula (1) or a salt thereof may be present in the biomolecule represented by B—$F^1$, wherein L is the spacer between B and $F^1$. Thirdly, the group according to formula (1) or a salt thereof may be formed during the conjugation reaction itself. In the latter option, $Q^1$ and $F^1$ are selected as such that their reaction product, i.e. connecting group $Z^3$, contains or is the group according to formula (1) or a salt thereof. Preferably, the group according to formula (1) or a salt thereof is introduced according to the first or second of the above mentioned options, most preferably according to the first option. In case the group according to formula (1) or a salt thereof is already present as such during the conjugation reaction, the positive effect on solubility and absence of in-process aggregation, as recited above, improve the efficiency of the conjugation reaction. In case the group according to formula (1) or a salt thereof is present in the linker-conjugate, even hydrophobic drugs can readily be subjected to the conjugation reaction.

Linker-Conjugate

The linker-conjugate is represented by $Q^1$-D, preferably by $Q^1$-L-D, wherein D is a target molecule, L is a linker linking $Q^1$ and D as further defined above, $Q^1$ is a reactive group capable of reacting with functional group $F^1$ on the biomolecule and each occurrence of "—" is independently a bond or a spacer moiety. In one embodiment, "—" is a spacer moiety as defined herein. In one embodiment, "—" is a bond, typically a covalent bond. The linker-conjugate is a compound wherein a target molecule is covalently connected to a reactive group $Q^1$, preferably via a linker or spacer, most preferably via linker L as defined above. The linker-conjugate may be obtained via reaction of a reactive group $Q^2$ present on a linker-construct with a reactive group present on a target molecule.

Preferably, the group according to formula (1), or the salt thereof, is situated in between $Q^1$ and D. In other words, reactive group $Q^1$ is covalently bonded to a first end of the group according to formula (1), and target molecule D is covalently bonded to a second end of the group according to formula (1). Herein, "first end" and "second end" both refer to either the carbonyl or carboxy end of the group according to formula (1) or to the sulfamide end of the group according to formula (1), but logically not to the same end.

As will be appreciated by the person skilled in the art, the linker-conjugate according to the invention may comprise more than one target molecule D, e.g. two, three, four, five, etc. Consequently, the linker-conjugate may thus comprise more than one "second end". Similarly, the linker-conjugate may comprise more than one reactive group $Q^1$, i.e. the linker-conjugate may comprise more than one first end. When more than one reactive group $Q^1$ is present the groups $Q^1$ may be the same or different, and when more than one target molecule D is present the target molecule D may be the same or different.

The linker-conjugate according to the invention may therefore also be denoted as $(Q^1)_y Sp(D)_z$, wherein y is an integer in the range of 1 to 10 and z is an integer in the range of 1 to 10. Herein:

y is an integer in the range of 1 to 10;
z is an integer in the range of 1 to 10;
$Q^1$ is a reactive group capable of reacting with a functional group $F^1$ present on a biomolecule;
D is an target molecule;
Sp is a spacer moiety, wherein a spacer moiety is defined as a moiety that spaces (i.e. provides a certain distance between) and covalently links reactive group $Q^1$ and target molecule D, preferably wherein said spacer moiety is linker L as defined above, and thus comprises a group according to formula (1) or a salt thereof.

Preferably, y is 1, 2, 3 or 4, more preferably y is 1 or 2 and most preferably, y is 1. Preferably, z is 1, 2, 3, 4, 5 or 6, more preferably z is 1, 2, 3 or 4, even more preferably z is 1, 2 or 3, yet even more preferably z is 1 or 2 and most preferably z is 1. More preferably, y is 1 or 2, preferably 1, and z is 1, 2, 3 or 4, yet even more preferably y is 1 or 2, preferably 1, and z is 1, 2 or 3, yet even more preferably y is 1 or 2, preferably 1, and z is 1 or 2, and most preferably y is 1 and z is 1. In a preferred embodiment, the linker-conjugate is according to the formula $Q^1 Sp(D)_4$, $Q^1 Sp(D)_3$, $Q^1 Sp(D)_2$ or $Q^1 SpD$.

Target molecule D is defined above. D is preferably an "active substance" or "pharmaceutically active substance", and refers to a pharmacological and/or biological substance, i.e. a substance that is biologically and/or pharmaceutically active, for example a drug, a prodrug, a diagnostic agent. Preferably, the active substance is selected from the group consisting of drugs and prodrugs. More preferably, the active substance is a pharmaceutically active compounds, in particular low to medium molecular weight compounds (e.g. about 200 to about 2500 Da, preferably about 300 to about 1750 Da). In a further preferred embodiment, the active substance is selected from the group consisting of cytotoxins, antiviral agents, antibacterials agents, peptides and oligonucleotides. Examples of cytotoxins include colchicine, vinca alkaloids, anthracyclines, camptothecins, doxorubicin, daunorubicin, taxanes, calicheamycins, tubulysins, irinotecans, an inhibitory peptide, amanitin, deBouganin, duocarmycins, maytansines, auristatins or pyrrolobenzodiazepines (PBDs). Preferred active substances include vinca alkaloids, anthracyclines, camptothecins, taxanes, tubulysins, amanitin, duocarmycins, maytansines, auristatins and pyrrolobenzodiazepines, in particular vinca alkaloids, anthracyclines, camptothecins, taxanes, tubulysins, amanitin, maytansines and auristatins.

The linker-conjugate comprises a reactive group $Q^1$ that is capable of reacting with a functional group $F^1$ present on a biomolecule. Functional groups are known to a person skilled in the art and may be defined as any molecular entity that imparts a specific property onto the molecule harbouring it. For example, a functional group in a biomolecule may constitute an amino group, a thiol group, a carboxylic acid, an alcohol group, a carbonyl group, a phosphate group, or an aromatic group. The functional group in the biomolecule may be naturally present or may be placed in the biomolecule by a specific technique, for example a (bio)chemical or a genetic technique. The functional group that is placed in the biomolecule may be a functional group that is naturally present in nature, or may be a functional group that is prepared by chemical synthesis, for example an azide, a terminal alkyne or a phosphine moiety. Herein, the term "reactive group" may refer to a certain group that comprises a functional group, but also to a functional group itself. For example, a cyclooctynyl group is a reactive group comprising a functional group, namely a C—C triple bond. Similarly, an N-maleimidyl group is a reactive group, comprising a C—C double bond as a functional group. However, a functional group, for example an azido functional group, a thiol functional group or an amino functional group, may herein also be referred to as a reactive group.

The linker-conjugate may comprise more than one reactive group $Q^1$. When the linker-conjugate comprises two or more reactive groups $Q^1$, the reactive groups $Q^1$ may differ from each other. Preferably, the linker-conjugate comprises one reactive group $Q^1$.

Reactive group $Q^1$ that is present in the linker-conjugate, is able to react with a functional group $F^1$ that is present in a biomolecule to form connecting group $Z^3$. In other words, reactive group $Q^1$ needs to be complementary to a functional group $F^1$ present in a biomolecule. Herein, a reactive group is denoted as "complementary" to a functional group when said reactive group reacts with said functional group selectively to form connecting group $Z^3$, optionally in the presence of other functional groups. Complementary reactive and functional groups are known to a person skilled in the art, and are described in more detail below. Preferably, reactive group $Q^1$ and functional group $F^1$ are capable of reacting in a bioorthogonal reaction, as those reactions do not interfere with the biomolecules present during this reaction. Bioorthogonal reactions and functional groups suitable therein are known to the skilled person, for example from Gong and Pan, *Tetrahedron Lett.* 2015, 56, 2123-2132, and include Staudinger ligations and copper-free Click chemistry. It is thus preferred that $Q^1$ is selected from the group consisting of 1,3-dipoles, alkynes, (hetero)cyclooctynes, cyclooctenes, tetrazines, ketones, aldehydes, alkoxyamines, hydrazines and triphenylphosphine.

In a preferred embodiment, reactive group $Q^1$ is selected from the group consisting of, optionally substituted, N-maleimidyl groups, halogenated N-alkylamido groups, sulfonyloxy N-alkylamido groups, ester groups, carbonate groups, sulfonyl halide groups, thiol groups or derivatives thereof, alkenyl groups, alkynyl groups, (hetero)cycloalkynyl groups, bicyclo[6.1.0]non-4-yn-9-yl] groups, cycloalkenyl groups, tetrazinyl groups, azido groups, phosphine groups, nitrile oxide groups, nitrone groups, nitrile imine groups, diazo groups, ketone groups, (O-alkyl)hydroxylamino groups, hydrazine groups, halogenated N-maleimidyl groups, 1,1-bis(sulfonylmethyl)methylcarbonyl groups or elimination derivatives thereof, carbonyl halide groups, allenamide groups, 1,2-quinone groups or triazine groups.

In a preferred embodiment, $Q^1$ is an N-maleimidyl group. When $Q^1$ is an N-maleimidyl group, $Q^1$ is preferably unsubstituted. $Q^1$ is thus preferably according to formula (9a), as shown below. A preferred example of such a maleimidyl group is 2,3-diaminopropionic acid (DPR) maleimidyl, which may be connected to the remainder of the linker-conjugate through the carboxylic acid moiety. In another preferred embodiment, $Q^1$ is a halogenated N-alkylamido group. When $Q^1$ is a halogenated N-alkylamido group, it is preferred that $Q^1$ is according to formula (9b), as shown below, wherein k is an integer in the range of 1 to 10 and $R^4$ is selected from the group consisting of —Cl, —Br and —I. Preferably k is 1, 2, 3 or 4, more preferably k is 1 or 2 and most preferably k is 1. Preferably, $R^4$ is —I or —Br. More preferably, k is 1 or 2 and $R^4$ is —I or —Br, and most preferably k is 1 and $R^4$ is —I or Br.

In another preferred embodiment, $Q^1$ is a sulfonyloxy N-alkylamido group. When $Q^1$ is a sulfonyloxy N-alkylamido group, it is preferred that $Q^1$ is according to formula (9b), as shown below, wherein k is an integer in the range of 1 to 10 and $R^4$ is selected from the group consisting of —O-mesyl, —O-phenylsulfonyl and —O-tosyl. Preferably k is 1, 2, 3 or 4, more preferably k is 1 or 2, even more preferably k is 1. Most preferably k is 1 and $R^4$ is selected from the group consisting of —O-mesyl, —O-phenylsulfonyl and —O-tosyl.

In another preferred embodiment, $Q^1$ is an ester group. When $Q^1$ is an ester group, it is preferred that the ester group is an activated ester group. Activated ester groups are known to the person skilled in the art. An activated ester group is herein defined as an ester group comprising a good leaving group, wherein the ester carbonyl group is bonded to said good leaving group. Good leaving groups are known to the person skilled in the art. It is further preferred that the activated ester is according to formula (9c), as shown below, wherein $R^5$ is selected from the group consisting of —N—succinimidyl (NHS), —N-sulfo-succinimidyl (sulfo-NHS), -(4-nitrophenyl), -pentafluorophenyl or -tetrafluorophenyl (TFP).

In another preferred embodiment, $Q^1$ is a carbonate group. When $Q^1$ is a carbonate group, it is preferred that the carbonate group is an activated carbonate group. Activated carbonate groups are known to a person skilled in the art. An activated carbonate group is herein defined as a carbonate group comprising a good leaving group, wherein the carbonate carbonyl group is bonded to said good leaving group. It is further preferred that the carbonate group is according to formula (9d), as shown below, wherein $R^7$ is selected from the group consisting of —N-succinimidyl, —N-sulfo-succinimidyl, -(4-nitrophenyl), -pentafluorophenyl or -tetrafluorophenyl. In another preferred embodiment, $Q^1$ is a sulfonyl halide group according to formula (9e) as shown below, wherein X is selected from the group consisting of F, Cl, Br and I. Preferably X is $C_1$ or Br, more preferably Cl.

In another preferred embodiment, $Q^1$ is a thiol group (9f), or a derivative or a precursor of a thiol group. A thiol group may also be referred to as a mercapto group. When $Q^1$ is a derivative or a precursor of a thiol group, the thiol derivative is preferably according to formula (9g), (9h) or (9zb) as shown below, wherein $R^8$ is an, optionally substituted, $C_1$-$C_{12}$ alkyl group or a $C_2$-$C_{12}$ (hetero)aryl group, V is O or S and $R^{16}$ is an, optionally substituted, $C_1$-$C_{12}$ alkyl group. More preferably $R^8$ is an, optionally substituted, $C_1$-$C_6$ alkyl group or a $C_2$-$C_6$ (hetero)aryl group, and even more preferably $R^8$ is methyl, ethyl, n-propyl, i-propyl, n-butyl, s-butyl, t-butyl or phenyl. Even more preferably, $R^8$ is methyl or phenyl, most preferably methyl. More preferably $R^{16}$ is an optionally substituted $C_1$-$C_6$ alkyl group, and even more preferably $R^{16}$ is methyl, ethyl, n-propyl, i-propyl, n-butyl, s-butyl or t-butyl, most preferably methyl. When $Q^1$ is a thiol-derivative according to formula (9g) or (9zb), and $Q^1$ is reacted with a reactive group $F^1$ on a biomolecule, said thiol-derivative is converted to a thiol group during the process. When $Q^1$ is according to formula (9h), $Q^1$ is —SC(O)O$R^8$ or —SC(S)O$R^8$, preferably SC(O)O$R^8$, wherein $R^8$, and preferred embodiments thereof, are as defined above.

In another preferred embodiment, $Q^1$ is an alkenyl group, wherein the alkenyl group is linear or branched, and wherein the alkenyl group is optionally substituted. The alkenyl group may be a terminal or an internal alkenyl group. The alkenyl group may comprise more than one C—C double bond, and if so, preferably comprises two C—C double bonds. When the alkenyl group is a dienyl group, it is further preferred that the two C—C double bonds are separated by one C—C single bond (i.e. it is preferred that the dienyl group is a conjugated dienyl group). Preferably said alkenyl group is a $C_2$-$C_{24}$ alkenyl group, more preferably a $C_2$-$C_{12}$ alkenyl group, and even more preferably a $C_2$-$C_6$ alkenyl group. It is further preferred that the alkenyl group is a terminal alkenyl group. More preferably, the alkenyl group is according to formula (9i) as shown below, wherein l is an integer in the range of 0 to 10, preferably in the range of 0 to 6, and p is an integer in the range of 0 to 10, preferably 0 to 6. More preferably, l is 0, 1, 2, 3 or 4, more preferably l is 0, 1 or 2 and most preferably l is 0 or 1. More preferably, p is 0, 1, 2, 3 or 4, more preferably p is 0, 1 or 2 and most preferably p is 0 or 1. It is particularly preferred that p is 0 and l is 0 or 1, or that p is 1 and l is 0 or 1.

In another preferred embodiment, $Q^1$ is an alkynyl group, wherein the alkynyl group is linear or branched, and wherein the alkynyl group is optionally substituted. The alkynyl group may be a terminal or an internal alkynyl group. Preferably said alkynyl group is a $C_2$-$C_{24}$ alkynyl group, more preferably a $C_2$-$C_{12}$ alkynyl group, and even more preferably a $C_2$-$C_6$ alkynyl group. It is further preferred that the alkynyl group is a terminal alkynyl group. More preferably, the alkynyl group is according to formula (9j) as shown below, wherein l is an integer in the range of 0 to 10, preferably in the range of 0 to 6. More preferably, l is 0, 1, 2, 3 or 4, more preferably l is 0, 1 or 2 and most preferably l is 0 or 1. In a further preferred embodiment, the alkynyl group is according to formula (9j) wherein l is 3.

In another preferred embodiment, $Q^1$ is a cycloalkenyl group. The cycloalkenyl group is optionally substituted. Preferably said cycloalkenyl group is a $C_3$-$C_{24}$ cycloalkenyl group, more preferably a $C_3$-$C_{12}$ cycloalkenyl group, and even more preferably a $C_3$-$C_8$ cycloalkenyl group. In a preferred embodiment, the cycloalkenyl group is a trans-cycloalkenyl group, more preferably a trans-cyclooctenyl group (also referred to as a TCO group) and most preferably a trans-cyclooctenyl group according to formula (9zi) or (9zj) as shown below. In another preferred embodiment, the cycloalkenyl group is a cyclopropenyl group, wherein the cyclopropenyl group is optionally substituted. In another preferred embodiment, the cycloalkenyl group is a norbornenyl group, an oxanorbornenyl group, a norbornadienyl group or an oxanorbornadienyl group, wherein the norbornenyl group, oxanorbornenyl group, norbornadienyl group or an oxanorbornadienyl group is optionally substituted. In a further preferred embodiment, the cycloalkenyl group is according to formula (9k), (9l), (9m) or (9zc) as shown below, wherein T is $CH_2$ or O, $R^9$ is independently selected from the group consisting of hydrogen, a linear or branched $C_1$-$C_{12}$ alkyl group or a $C_4$-$C_{12}$ (hetero)aryl group, and $R^{19}$ is selected from the group consisting of hydrogen and fluorinated hydrocarbons. Preferably, $R^9$ is independently hydrogen or a $C_1$-$C_6$ alkyl group, more preferably $R^9$ is independently hydrogen or a $C_1$-$C_4$ alkyl group. Even more preferably $R^9$ is independently hydrogen or methyl, ethyl, n-propyl, i-propyl, n-butyl, s-butyl or t-butyl. Yet even more preferably $R^9$ is independently hydrogen or methyl. In a further preferred embodiment, $R^{19}$ is selected from the group of hydrogen and —$CF_3$, —$C_2F_5$, —$C_3F_7$ and —$C_4F_9$, more preferably hydrogen and —$CF_3$. In a further preferred embodiment, the cycloalkenyl group is according to formula (9k), wherein one $R^9$ is hydrogen and the other $R_9$ is a methyl group. In another further preferred embodiment, the cycloalkenyl group is according to formula (9l), wherein both $R^9$ are hydrogen. In these embodiments it is further preferred that l is 0 or 1. In another further preferred embodiment, the cycloalkenyl group is a norbornenyl (T is $CH_2$) or an oxanorbornenyl (T is O) group according to formula (9m), or a norbornadienyl (T is $CH_2$) or an oxanorbornadienyl (T is O) group according to formula (9zc), wherein $R^9$ is hydrogen and $R^{19}$ is hydrogen or —$CF_3$, preferably —$CF_3$.

In another preferred embodiment, $Q^1$ is a (hetero)cycloalkynyl group. The (hetero)cycloalkynyl group is optionally substituted. Preferably, the (hetero)cycloalkynyl group is a (hetero)cyclooctynyl group, i.e. a heterocyclooctynyl group or a cyclooctynyl group, wherein the (hetero)cyclooctynyl group is optionally substituted. In a further preferred embodiment, the (hetero)cyclooctynyl group is substituted with one or more halogen atoms, preferably fluorine atoms, more preferably the (hetero)cyclooctynyl group is substituted with one fluorine atom, as in mono-fluoro-cyclooctcyne (MCFO). Preferably, the mono-fluoro-cyclooctcyne group is according to formula (9zo). In a further preferred embodiment, the (hetero)cyclooctynyl group is according to formula (9n), also referred to as a DIBO group, (9o), also referred to as a DIBAC group or (9p), also referred to as a BARAC group, or (9zk), also referred to as a COMBO group, all as shown below, wherein U is O or $NR^9$, and preferred embodiments of $R^9$ are as defined above. The aromatic rings in (9n) are optionally O-sulfonylated at one or more positions, whereas the rings of (9o) and (9p) may be halogenated at one or more positions. For (9n), U is preferably O.

In an especially preferred embodiment, the nitrogen atom attached to $R^1$ in compound (4b) is the nitrogen atom in the ring of the heterocycloalkyne group such as the nitrogen atom in (9o). In other words, c, d and g are 0 in compound (4b) and $R^1$ and $Q^1$, together with the nitrogen atom they are attached to, form a heterocycloalkyne group, preferably a heterocyclooctyne group, most preferably the heterocyclooctyne group according to formula (9o) or (9p). Herein, the carbonyl moiety of (9o) is replaced by the sulfonyl group of the group according to formula (1). Alternatively, the nitrogen atom to which $R^1$ is attached is the same atom as the atom designated as U in formula (9n). In other words, when $Q^1$ is according to formula (9n), U may be the right nitrogen atom of the group according to formula (1), or U=$NR^9$ and $R^9$ is the remainder of the group according to formula (1) and $R^1$ is the cyclooctyne moiety.

In another preferred embodiment, $Q^1$ is an, optionally substituted, bicyclo[6.1.0]non-4-yn-9-yl]group, also referred to as a BCN group. Preferably, the bicyclo[6.1.0] non-4-yn-9-yl] group is according to formula (9q) as shown below.

In another preferred embodiment, $Q^1$ is a conjugated (hetero)diene group capable of reacting in a Diels-Alder reaction. Preferred (hetero)diene groups include optionally substituted tetrazinyl groups, optionally substituted 1,2-quinone groups and optionally substituted triazine groups. More preferably, said tetrazinyl group is according to formula (9r), as shown below, wherein $R^9$ is selected from the group consisting of hydrogen, a linear or branched $C_1$-$C_{12}$ alkyl group or a $C_4$-$C_{12}$ (hetero)aryl group. Preferably, $R^9$ is hydrogen, a $C_1$-$C_6$ alkyl group or a $C_4$-$C_{10}$ (hetero)aryl group, more preferably $R^9$ is hydrogen, a $C_1$-$C_4$ alkyl group or a $C_4$-$C_6$ (hetero)aryl group. Even more preferably $R^9$ is hydrogen, methyl, ethyl, n-propyl, i-propyl, n-butyl, s-butyl, t-butyl or pyridyl. Yet even more preferably $R^9$ is hydrogen, methyl or pyridyl. More preferably, said 1,2-quinone group is according to formula (9zl) or (9zm). Said triazine group may be any regioisomer. More preferably, said triazine group is a 1,2,3-triazine group or a 1,2,4-triazine group, which may be attached via any possible location, such as indicated in formula (9zn). The 1,2,3-triazine is most preferred as triazine group.

In another preferred embodiment, $Q^1$ is an azido group according to formula (9s) as shown below. In another preferred embodiment, $Q^1$ is an, optionally substituted, triarylphosphine group that is suitable to undergo a Staudinger ligation reaction. Preferably, the phosphine group is according to formula (9t) as shown below, wherein $R^{10}$ is a (thio)ester group. When $R^{10}$ is a (thio)ester group, it is preferred that $R^{10}$ is —C(O)—V—$R^{11}$, wherein V is O or S and $R^{11}$ is a $C_1$-$C_{12}$ alkyl group. Preferably, $R^{11}$ is a $C_1$-$C_6$ alkyl group, more preferably a $C_1$-$C_4$ alkyl group. Most preferably, $R^{11}$ is a methyl group.

In another preferred embodiment, $Q^1$ is a nitrile oxide group according to formula (9u) as shown below.

In another preferred embodiment, $Q^1$ is a nitrone group. Preferably, the nitrone group is according to formula (9v) as shown below, wherein $R^{12}$ is selected from the group consisting of linear or branched $C_1$-$C_{12}$ alkyl groups and $C_6$-$C_{12}$ aryl groups. Preferably, $R^{12}$ is a $C_1$-$C_6$ alkyl group, more preferably $R^{12}$ is a $C_1$-$C_4$ alkyl group. Even more preferably $R^{12}$ is methyl, ethyl, n-propyl, i-propyl, n-butyl, s-butyl or t-butyl. Yet even more preferably $R^{12}$ is methyl.

In another preferred embodiment, $Q^1$ is a nitrile imine group. Preferably, the nitrile imine group is according to formula (9w) or (9zd) as shown below, wherein $R^{13}$ is selected from the group consisting of linear or branched $C_1$-$C_{12}$ alkyl groups and $C_6$-$C_{12}$ aryl groups. Preferably, $R^{13}$ is a $C_1$-$C_6$ alkyl group, more preferably $R^{13}$ is a $C_1$-$C_4$ alkyl group. Even more preferably $R^{13}$ is methyl, ethyl, n-propyl, i-propyl, n-butyl, s-butyl or t-butyl. Yet even more preferably $R^{13}$ is methyl. In another preferred embodiment, $Q^1$ is a diazo group. Preferably, the diazo group is according to formula (9x) as shown below, wherein $R^{14}$ is selected from the group consisting of hydrogen or a carbonyl derivative. More preferably, $R^{14}$ is hydrogen.

In another preferred embodiment, $Q^1$ is a ketone group. More preferably, the ketone group is according to formula (9y) as shown below, wherein $R^{15}$ is selected from the group consisting of linear or branched $C_1$-$C_{12}$ alkyl groups and $C_6$-$C_{12}$ aryl groups. Preferably, $R^{15}$ is a $C_1$-$C_6$ alkyl group, more preferably $R^{15}$ is a $C_1$-$C_4$ alkyl group. Even more preferably $R^{15}$ is methyl, ethyl, n-propyl, i-propyl, n-butyl, s-butyl or t-butyl. Yet even more preferably $R^{15}$ is methyl.

In another preferred embodiment, $Q^1$ is an (O-alkyl) hydroxylamino group. More preferably, the (O-alkyl)hydroxylamino group is according to formula (9z) as shown below.

In another preferred embodiment, $Q^1$ is a hydrazine group. Preferably, the hydrazine group is according to formula (9za) as shown below.

In another preferred embodiment, $Q^1$ is a halogenated N-maleimidyl group or a sulfonylated N-maleimidyl group. When $Q^1$ is a halogenated or sulfonylated N-maleimidyl group, $Q^1$ is preferably according to formula (9ze) as shown below, wherein $R^6$ is independently selected from the group consisting of hydrogen F, Cl, Br, I—$SR^{18a}$ and —OS(O)$_2$ $R^{18b}$, wherein $R^{18a}$ is an optionally substituted $C_4$-$C_{12}$ (hetero)aryl groups, preferably phenyl or pyrydyl, and $R^{18b}$ is selected from the group consisting of, optionally substituted, $C_1$-$C_{12}$ alkyl groups and $C_4$-$C_{12}$ (hetero)aryl groups, preferably tolyl or methyl, and with the proviso that at least one $R^6$ is not hydrogen. When $R^6$ is halogen (i.e. when $R^6$ is F, Cl, Br or I), it is preferred that $R^6$ is Br. In one embodiment, the halogenated N-maleimidyl group is halogentated 2,3-diaminopropionic acid (DPR) maleimidyl, which may be connected to the remainder of the linker-conjugate through the carboxylic acid moiety.

In another preferred embodiment, $Q^1$ is a carbonyl halide group according to formula (9zf) as shown below, wherein X is selected from the group consisting of F, Cl, Br and I. Preferably, X is $C_1$ or Br, and most preferably, X is $C_1$.

In another preferred embodiment, $Q^1$ is an allenamide group according to formula (9zg). In another preferred embodiment, $Q^1$ is a 1,1-bis(sulfonylmethyl)methylcarbonyl group according to formula (9zh), or an elimination derivative thereof, wherein $R^{18}$ is selected from the group consisting of, optionally substituted, $C_1$-$C_{12}$ alkyl groups and $C_4$-$C_{12}$ (hetero)aryl groups. More preferably, $R^{18}$ is an, optionally substituted, $C_1$-$C_6$ alkyl group or a $C_4$-$C_6$ (hetero)aryl group, and most preferably a phenyl group.

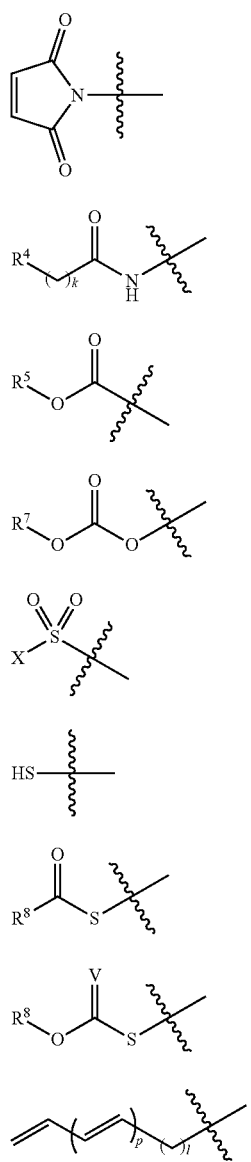
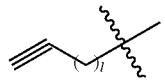
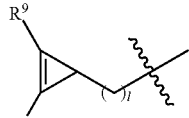
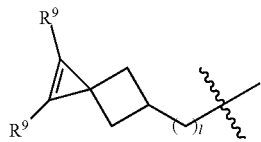
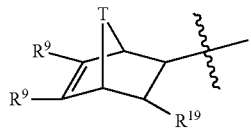
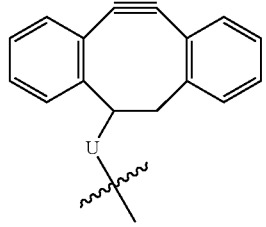
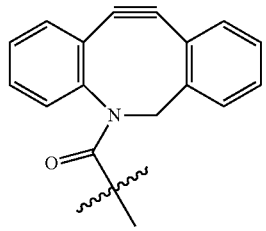
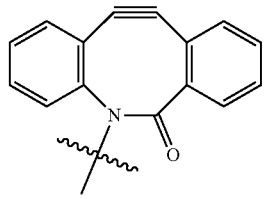
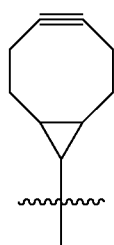

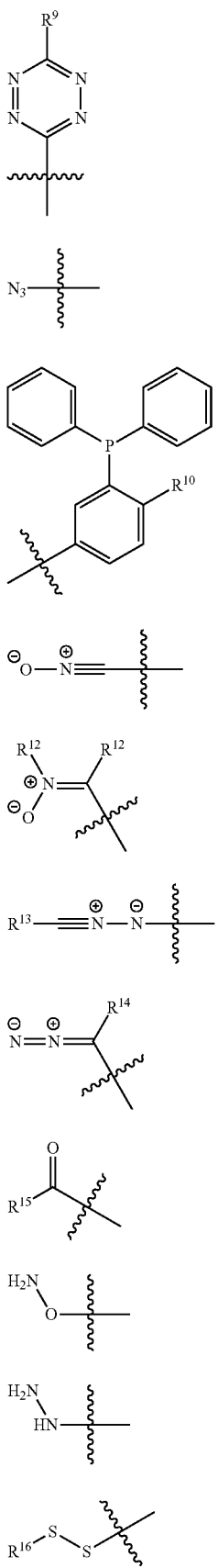
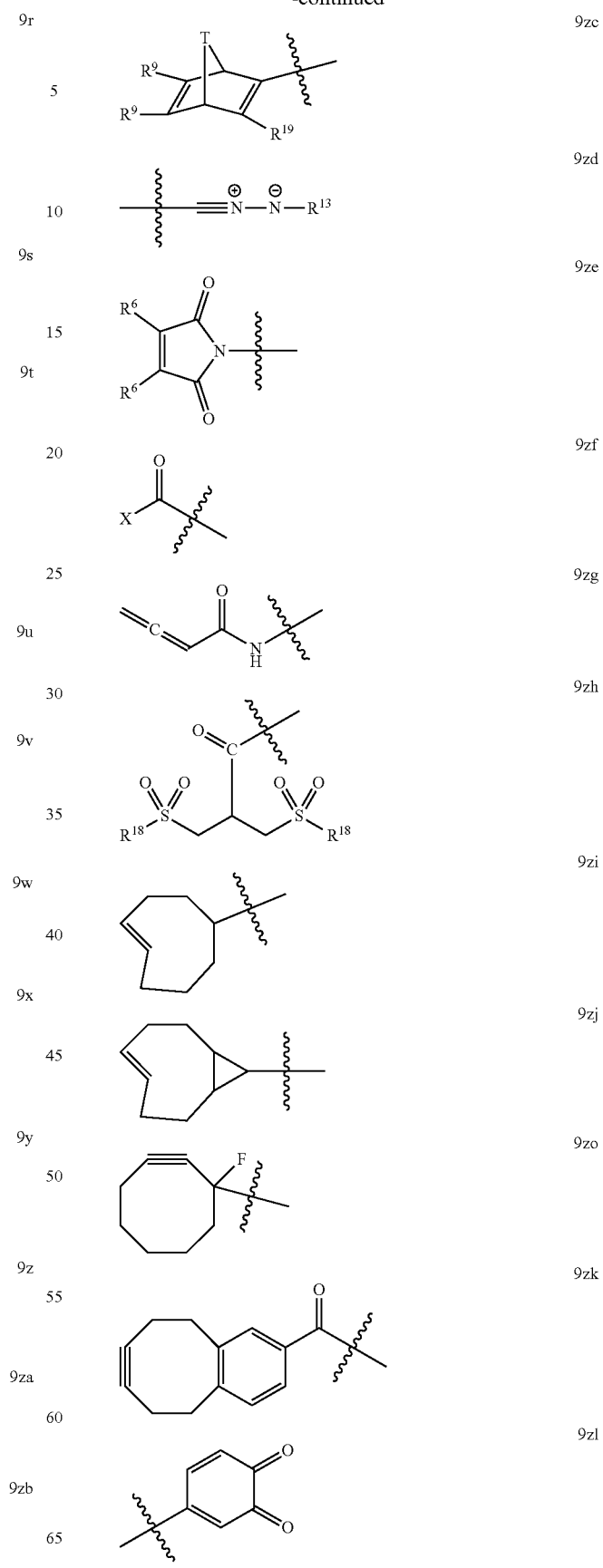

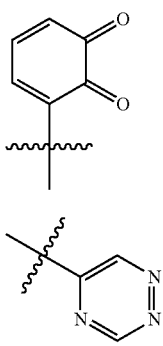

wherein k, l, X, T, U, V, R⁴, R⁵, R⁶, R⁷, R⁸, R⁹, R¹⁰, R¹¹, R¹², R¹³, R¹⁴, R¹⁵, R¹⁶, R¹⁷, R¹⁸ and R¹⁹ are as defined above.

In a preferred embodiment of the conjugation process according to the invention as described herein below, conjugation is accomplished via a cycloaddition, such as a Diels-Alder reaction or a 1,3-dipolar cycloaddition, preferably the 1,3-dipolar cycloaddition. According to this embodiment, the reactive group $Q^1$ (as well as $F^1$ on the biomolecule) is selected from groups reactive in a cycloaddition reaction. Herein, reactive groups $Q^1$ and $F^1$ are complementary, i.e. they are capable of reacting with each other in a cycloaddition reaction, the obtained cyclic moiety being connecting group $Z^3$.

For a Diels-Alder reaction, one of $F^1$ and $Q^1$ is a diene and the other of $F^1$ and $Q^1$ is a dienophile. As appreciated by the skilled person, the term "diene" in the context of the Diels-Alder reaction refers to 1,3-(hetero)dienes, and includes conjugated dienes ($R_2C=CR-CR=CR_2$), imines (e.g. $R_2C=CR-N=CR_2$ or $R_2C=CR-CR=NR$, $R_2C=N-N=CR_2$) and carbonyls (e.g. $R_2C=CR-CR=O$ or $O=CR-CR=O$). Hetero-Diels-Alder reactions with N- and O-containing dienes are known to a person skilled in the art. Any diene known in the art to be suitable for Diels-Alder reactions may be used as reactive group $Q^1$ or F. Preferred dienes include tetrazines as described above, 1,2-quinones as described above and triazines as described above. Although any dienophile known in the art to be suitable for Diels-Alder reactions may be used as reactive groups $Q^1$ or $F^1$, the dienophile is preferably an alkene or alkyne group as described above, most preferably an alkyne group. For conjugation via a Diels-Alder reaction, it is preferred that $F^1$ is the diene and $Q^1$ is the dienophile. Herein, when $Q^1$ is a diene, $F^1$ is a dienophile and when $Q^1$ is a dienophile, $F^1$ is a diene.

Most preferably, $Q^1$ is a dienophile, preferably $Q^1$ is or comprises an alkynyl group, and $F^1$ is a diene, preferably a tetrazine, 1,2-quinone or triazine group.

For a 1,3-dipolar cycloaddition, one of $F^1$ and $Q^1$ is a 1,3-dipole and the other of $F^1$ and $Q^1$ is a dipolarophile. Any 1,3-dipole known in the art to be suitable for 1,3-dipolar cycloadditions may be used as reactive group $Q^1$ or $F^1$. Preferred 1,3-dipoles include azido groups, nitrone groups, nitrile oxide groups, nitrile imine groups and diazo groups. Although any dipolarophile known in the art to be suitable for 1,3-dipolar cycloadditions may be used as reactive groups $Q^1$ or $F^1$, the dipolarophile is preferably an alkene or alkyne group, most preferably an alkyne group. For conjugation via a 1,3-dipolar cycloaddition, it is preferred that $F^1$ is the 1,3-dipole and $Q^1$ is the dipolarophile. Herein, when $Q^1$ is a 1,3-dipole, $F^1$ is a dipolarophile and when $Q^1$ is a dipolarophile, $F^1$ is a 1,3-dipole. Most preferably, $Q^1$ is a dipolarophile, preferably $Q^1$ is or comprises an alkynyl group, and $F^1$ is a 1,3-dipole, preferably an azido group.

Thus, in a preferred embodiment, $Q^1$ is selected from dipolarophiles and dienophiles. Preferably, $Q^1$ is an alkene or an alkyne group. In an especially preferred embodiment, $Q^1$ comprises an alkyne group, preferably selected from the alkynyl group as described above, the cycloalkenyl group as described above, the (hetero)cycloalkynyl group as described above and a bicyclo[6.1.0]non-4-yn-9-yl] group, more preferably $Q^1$ is selected from the formulae (9j), (9n), (9o), (9p), (9q), (9zk) and (9zo) as defined above and depicted below, such as selected from the formulae (9j), (9n), (9o), (9p), (9q) and (9zk), more preferably selected from the formulae (9n), (9o), (9p), (9q) and (9zk) or from the formulae (9j), (9n), (9q) and (9zo). Most preferably, $Q^1$ is a bicyclo[6.1.0]non-4-yn-9-yl]group, preferably of formula (9q). These groups are known to be highly effective in the conjugation with azido-functionalized biomolecules as described herein, and when the sulfamide linker according to the invention is employed in such linker-conjugates, any aggregation is beneficially reduced to a minimum.

As was described above, in the linker-conjugate, $Q^1$ is capable of reacting with a reactive group $F^1$ that is present on a biomolecule. Complementary reactive groups $F^1$ for reactive group $Q^1$ are known to a person skilled in the art, and are described in more detail below. Some representative examples of reaction between $F^1$ and $Q^1$ and their corresponding products comprising connecting group $Z^3$ are depicted in FIG. 11.

As described above, D and $Q^1$ are covalently attached in the linker-conjugate according to the invention, preferably via linker L as defined above. Covalent attachment of D to the linker may occur for example via reaction of a functional group $F^2$ present on D with a reactive group $Q^2$ present on the linker. Suitable organic reactions for the attachment of D to a linker are known to a person skilled in the art, as are functional groups $F^2$ that are complementary to a reactive group $Q^2$. Consequently, D may be attached to the linker via a connecting group Z.

The term "connecting group" herein refers to the structural element connecting one part of a compound and another part of the same compound. As will be understood by the person skilled in the art, the nature of a connecting group depends on the type of organic reaction with which the connection between the parts of said compound was obtained. As an example, when the carboxyl group of R—C(O)—OH is reacted with the amino group of $H_2N$—R' to form R—C(O)—N(H)—R', R is connected to R' via connecting group Z, and Z may be represented by the group —C(O)—N(H)—.

Reactive group $Q^1$ may be attached to the linker in a similar manner. Consequently, $Q^1$ may be attached to the spacer-moiety via a connecting group Z.

Numerous reactions are known in the art for the attachment of a target molecule to a linker, and for the attachment of a reactive group $Q^1$ to a linker. Consequently, a wide variety of connecting groups Z may be present in the linker-conjugate.

In one embodiment, the linker-conjugate is a compound according to the formula:

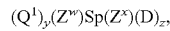

wherein:
y is an integer in the range of 1 to 10;
z is an integer in the range of 1 to 10;
$Q^1$ is a reactive group capable of reacting with a functional group $F^1$ present on a biomolecule;

D is a target molecule;
Sp is a spacer moiety, wherein a spacer moiety is defined as a moiety that spaces (i.e. provides a certain distance between) and covalently links $Q^1$ and D;
$Z^w$ is a connecting group connecting $Q^1$ to said spacer moiety;
$Z^x$ is a connecting group connecting D to said spacer moiety; and wherein said spacer moiety is linker L, and thus comprises a group according to formula (1) or a salt thereof, wherein the group according to formula (1) is as defined above.

In a preferred embodiment, a in the group according to formula (1) is 0. In another preferred embodiment, a in the group according to formula (1) is 1.

Preferred embodiments for y and z are as defined above for $(Q^1)_y Sp(D)_z$. It is further preferred that the compound is according to the formula $Q^1(Z^w)Sp(Z^x)(D)_4$, $Q^1(Z^w)Sp(Z^x)(D)_3$, $Q^1(Z^w)Sp(Z^x)(D)_2$ or $Q^1(Z^w)Sp(Z^x)D$, more preferably $Q^1(Z^w)Sp(Z^x)(D)_2$ or $Q^1(Z^w)Sp(Z^x)D$ and most preferably $Q^1(Z^w)Sp(Z^x)D$, wherein $Z^w$ and $Z^x$ are as defined above.

Preferably, $Z^w$ and $Z^x$ are independently selected from the group consisting of —O—, —S—, —NR$^2$—, —N=N—, —C(O)—, —C(O)NR$^2$—, —OC(O)—, —OC(O)O—, —OC(O)NR$^2$, —NR$_2$C(O)—, —NR$^2$C(O)O—, —NR$^2$C(O)NR$^2$—, —SC(O)—, —SC(O)O—, —SC(O)NR$^2$—, —S(O)—, —S(O)$_2$—, —OS(O)$_2$—, —OS(O)$_2$O—, —OS(O)$_2$NR$^2$—, —OS(O)—, —OS(O)O—, —OS(O)NR$^2$—, —ONR$^2$C(O)—, —ONR$^2$C(O)O—, —ONR$^2$C(O)NR$^2$—, —NR$^2$OC(O)—, —NR$^2$OC(O)O—, —NR$^2$OC(O)NR$^2$—, —ONR$^2$C(S)—, —ONR$^2$C(S)O—, —ONR$^2$C(S)NR$^2$—, —NR$^2$OC(S)—, —NR$^2$OC(S)O—, —NR$^2$OC(S)NR$^2$—, —OC(S)—, —OC(S)O—, —OC(S)NR$^2$—, —NR$^2$C(S)—, —NR$^2$C(S)O—, —NR$^2$C(S)NR$^2$—, —SS(O)$_2$—, —SS(O)$_2$O—, —SS(O)$_2$NR$^2$—, —NR$_2$OS(O)—, —NR$_2$OS(O)O—, —NR$_2$OS(O)NR$^2$—, —NR$^2$OS(O)$_2$—, —NR$_2$OS(O)$_2$O—, —NR$_2$OS(O)$_2$NR$^2$—, —ONR$^2$S(O)—, —ONR$^2$S(O)O—, —ONR$^2$S(O)NR$^2$—, —ONR$^2$S(O)$_2$—, —ONR$^2$S(O)$_2$O—, —ONR$^2$S(O)$_2$NR$^2$—, —ONR$^2$S(O)$_2$—, —OP(O)(R$^2$)$_2$—, —SP(O)(R$^2$)$_2$—, —NR$^2$P(O)(R$^2$)$_2$— and combinations of two or more thereof, wherein R$^2$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Preferred embodiments for D and $Q^1$ are as defined above.

In one embodiment, the linker-conjugate is compound according to formula (4a) or (4b), or a salt thereof:

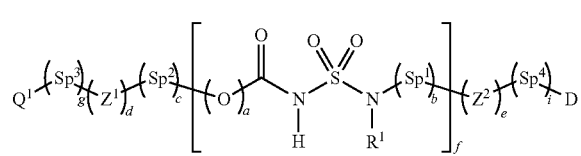

4a

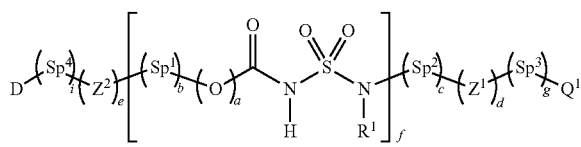

4b wherein:
a is independently 0 or 1;
b is independently 0 or 1;
c is 0 or 1;
d is 0 or 1;
e is 0 or 1;
f is an integer in the range of 1 to 150;
g is 0 or 1;
i is 0 or 1;
D is a target molecule;
$Q^1$ is a reactive group capable of reacting with a functional group $F^1$ present on a biomolecule;
$Sp^1$ is a spacer moiety;
$Sp^2$ is a spacer moiety;
$Sp^3$ is a spacer moiety;
$Sp^4$ is a spacer moiety;
$Z^1$ is a connecting group that connects $Q^1$ or $Sp^3$ to $Sp^2$, O or C(O) or N(R');
$Z^2$ is a connecting group that connects D or $Sp^4$ to $Sp^1$, N(R$^1$), O or C(O); and
$R^1$ is selected from the group consisting of hydrogen, $C_1$-$C_{24}$ alkyl groups, $C_3$-$C_{24}$ cycloalkyl groups, $C_1$-$C_{24}$ (hetero)aryl groups, $C_1$-$C_{24}$ alkyl(hetero)aryl groups and $C_1$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and NR$^3$ wherein R$^3$ is independently selected from the group consisting of hydrogen and $C_1$-$C_4$ alkyl groups; or
$R^1$ is D, $-[(Sp^1)_b(Z^2)_e(Sp^4)_i D]$ or $-[(Sp^2)_c(Z^1)_d(Sp^3)_g Q^1]$, wherein D is a further target molecule and $Sp^1$, $Sp^2$, $Sp^3$, $Sp^4$, $Z^1$, $Z^2$, $Q^1$, b, c, d, e, g and i are as defined above.

In a preferred embodiment, a is 1 in the compound according to formula (4a) or (4b). In another preferred embodiment, a is 0 in the compound according to formula (4a) or (4b).

As defined above, $Z^1$ is a connecting group that connects $Q^1$ or $Sp^3$ to $Sp^2$, O or C(O) or N(R$^1$), and $Z^2$ is a connecting group that connects D or $Sp^4$ to $Sp^1$, N(R$^1$), O or C(O). As described in more detail above, the term "connecting group" refers to a structural element connecting one part of a compound and another part of the same compound.

In a compound according to formula (4a), connecting group $Z^1$, when present (i.e. when d is 1), connects $Q^1$ (optionally via a spacer moiety $Sp^3$) to the O-atom or the C(O) group of the compound according to formula (4a), optionally via a spacer moiety $Sp^2$. More particularly, when $Z^1$ is present (i.e. d is 1), and when $Sp^3$ and $Sp^2$ are absent (i.e. g is 0 and c is 0), $Z^1$ connects $Q^1$ to the O-atom (a is 1) or to the C(O) group (a is 0) of the linker-conjugate according to formula (4a). When $Z^1$ is present (i.e. when d is 1), $Sp^3$ is present (i.e. g is 1) and $Sp^2$ is absent (i.e. c is 0), $Z^1$ connects spacer moiety $Sp^3$ to the O-atom (a is 1) or to the C(O) group (a is 0) of the linker-conjugate according to formula (4a). When $Z^1$ is present (i.e. d is 1), and when $Sp^3$ and $Sp^2$ are present (i.e. g is 1 and c is 1), $Z^1$ connects spacer moiety $Sp^3$ to spacer moiety $Sp^2$ of the linker-conjugate according to formula (4a). When $Z^1$ is present (i.e. when d is 1), $Sp^3$ is absent (i.e. g is 0) and $Sp^2$ is present (i.e. c is 1), $Z^1$ connects $Q^1$ to spacer moiety $Sp^2$ of the linker-conjugate according to formula (4a).

In a compound according to formula (4b), connecting group $Z^1$, when present (i.e. when d is 1), connects $Q^1$ (optionally via a spacer moiety $Sp^3$) to the N-atom of the N(R$^1$) group in the linker-conjugate according to formula (4b), optionally via a spacer moiety $Sp^2$. More particularly, when $Z^1$ is present (i.e. d is 1), and when $Sp^3$ and $Sp^2$ are absent (i.e. g is 0 and c is 0), $Z^1$ connects $Q^1$ to the N-atom of the $N(R^1)$ group of the linker-conjugate according to formula (4b). When $Z^1$ is present (i.e. when d is 1), $Sp^3$ is present (i.e. g is 1) and $Sp^2$ is absent (i.e. c is 0), $Z^1$ connects spacer moiety $Sp^3$ to the N-atom of the $N(R^1)$ group of the linker-conjugate according to formula (4b). When $Z^1$ is present (i.e. d is 1), and when $Sp^3$ and $Sp^2$ are present (i.e. g is 1 and c is 1), $Z^1$ connects spacer moiety $Sp^3$ to spacer moiety $Sp^2$ of the linker-conjugate according to formula (4b). When $Z^1$ is present (i.e. when d is 1), $Sp^3$ is absent (i.e. g is 0) and $Sp^2$ is present (i.e. c is 1), $Z^1$ connects $Q^1$ to spacer moiety $Sp^2$ of the linker-conjugate according to formula (4b).

In the compound according to formula (4a), when c, d and g are all 0, then $Q^1$ is attached directly to the O-atom (when a is 1) or to the C(O) group (when a is 0) of the linker-conjugate according to formula (4a).

In the compound according to formula (4b), when c, d and g are all 0, then $Q^1$ is attached directly to the N-atom of the $N(R^1)$ group of the linker-conjugate according to formula (4b).

In a compound according to formula (4a), connecting group $Z^2$, when present (i.e. when e is 1), connects D (optionally via a spacer moiety $Sp^4$) to the N-atom of the $N(R^1)$ group in the linker-conjugate according to formula (4a), optionally via a spacer moiety $Sp^1$. More particularly, when $Z^2$ is present (i.e. e is 1), and when $Sp^1$ and $Sp^4$ are absent (i.e. b is 0 and i is 0), $Z^2$ connects D to the N-atom of the $N(R^1)$ group of the linker-conjugate according to formula (4a). When $Z^2$ is present (i.e. when e is 1), $Sp^4$ is present (i.e. i is 1) and $Sp^1$ is absent (i.e. b is 0), $Z^2$ connects spacer moiety $Sp^4$ to the N-atom of the $N(R^1)$ group of the linker-conjugate according to formula (4a). When $Z^2$ is present (i.e. e is 1), and when $Sp^1$ and $Sp^4$ are present (i.e. b is 1 and i is 1), $Z^2$ connects spacer moiety $Sp^1$ to spacer moiety $Sp^4$ of the linker-conjugate according to formula (4a). When $Z^2$ is present (i.e. when e is 1), $Sp^4$ is absent (i.e. i is 0) and $Sp^1$ is present (i.e. b is 1), $Z^2$ connects D to spacer moiety $Sp^1$ of the linker-conjugate according to formula (4a).

In the compound according to formula (4a), when b, e and i are all 0, then D is attached directly to N-atom of the $N(R^1)$ group of the linker-conjugate according to formula (4a).

In the compound according to formula (4b), when b, e and i are all 0, then D is attached directly to the O-atom (when a is 1) or to the C(O) group (when a is 0) of the linker-conjugate according to formula (4b).

As will be understood by the person skilled in the art, the nature of a connecting group depends on the type of organic reaction with which the connection between the specific parts of said compound was obtained. A large number of organic reactions are available for connecting a reactive group $Q^1$ to a spacer moiety, and for connecting a target molecule to a spacer-moiety. Consequently, there is a large variety of connecting groups $Z^1$ and $Z^2$.

In a preferred embodiment of the linker-conjugate according to formula (4a) and (4b), $Z^1$ and $Z^2$ are independently selected from the group consisting of —O—, —S—, —SS—, —$NR^2$—, —N=N—, —C(O)—, —C(O)$NR^2$—, —OC(O)—, —OC(O)O—, —OC(O)$NR^2$—, —$NR_2$C(O)—, —$NR^2$C(O)O—, —$NR^2$C(O)$NR^2$—, —SC(O)—, —SC(O)O—, —S—C(O)$NR^2$—, —S(O)—, —S(O)$_2$—, —OS(O)$_2$—, —OS(O)$_2$O—, —OS(O)$_2NR^2$—, —OS(O)—, —OS(O)O—, —OS(O)$NR^2$—, —ONR$^2$C(O)—, —ONR$^2$C(O)O—, —ONR$^2$C(O)$NR^2$—, —$NR^2$OC(O)—, —$NR^2$OC(O)O—, —$NR^2$OC(O)$NR^2$—, —ONR$^2$C(S)—, —ONR$^2$C(S)O—, —ONR$^2$C(S)$NR^2$—, —$NR^2$OC(S)—, —$NR^2$OC(S)O—, —$NR^2$OC(S)$NR^2$—, —OC(S)—, —OC(S)O—, —OC(S)$NR^2$—, —$NR^2$C(S)—, —$NR^2$C(S)O—, —$NR^2$C(S)$NR^2$—, —SS(O)$_2$—, —SS(O)$_2$O—, —SS(O)$_2NR^2$—, —NR$_2$OS(O)—, —NR$_2$OS(O)O—, —NR$_2$OS(O)$NR^2$—, —$NR^2$OS(O)$_2$—, —NR$_2$OS(O)$_2$O—, —NR$_2$OS(O)$_2$NR$^2$—, —ONR$^2$S(O)—, —ONR$^2$S(O)O—, —ONR$^2$S(O)$NR^2$—, —ONR$^2$S(O)$_2$O—, —ONR$^2$S(O)$_2NR^2$—, —ONR$^2$S(O)$_2$—, —OP(O)($R^2$)$_2$—, —SP(O)($R^2$)$_2$—, —$NR^2$P(O)($R^2$)$_2$— and combinations of two or more thereof, wherein $R^2$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

As described above, in the compound according to formula (4a) or (4b), $Sp^1$, $Sp^2$, $Sp^3$ and $Sp^4$ are spacer-moieties. $Sp^1$, $Sp^2$, $Sp^3$ and $Sp^4$ may be, independently, absent or present (b, c, g and i are, independently, 0 or 1). $Sp^1$, if present, may be different from $Sp^2$, if present, from $Sp^3$ and/or from $Sp^4$, if present.

Spacer-moieties are known to a person skilled in the art. Examples of suitable spacer-moieties include (poly)ethylene glycol diamines (e.g. 1,8-diamino-3,6-dioxaoctane or equivalents comprising longer ethylene glycol chains), polyethylene glycol chains or polyethylene oxide chains, polypropylene glycol chains or polypropylene oxide chains and 1,x-diaminoalkanes wherein x is the number of carbon atoms in the alkane.

Another class of suitable spacer-moieties comprises cleavable spacer-moieties, or cleavable linkers. Cleavable linkers are well known in the art. For example Shabat et al., *Soft Matter* 2012, 6, 1073, incorporated by reference herein, discloses cleavable linkers comprising self-immolative moieties that are released upon a biological trigger, e.g. an enzymatic cleavage or an oxidation event. Some examples of suitable cleavable linkers are disulfide-linkers that are cleaved upon reduction, peptide-linkers that are cleaved upon specific recognition by a protease, e.g. cathepsin, plasmin or metalloproteases, or glycoside-based linkers that are cleaved upon specific recognition by a glycosidase, e.g. glucuronidase, or nitroaromatics that are reduced in oxygen-poor, hypoxic areas. Herein, suitable cleavable spacer-moieties also include spacer moieties comprising a specific, cleavable, sequence of amino acids. Examples include e.g. spacer-moieties comprising a Val-Ala (valine-alanine) or Val-Cit (valine-citrulline) moiety.

In a preferred embodiment of the linker-conjugate according to formula (4a) and (4b), spacer moieties $Sp^1$, $Sp^2$, $Sp^3$ and/or $Sp^4$, if present, comprise a sequence of amino acids. Spacer-moieties comprising a sequence of amino acids are known in the art, and may also be referred to as peptide linkers. Examples include spacer-moieties comprising a Val-Cit moiety, e.g. Val-Cit-PABC, Val-Cit-PAB, Fmoc-Val-Cit-PAB, etc. Preferably, a Val-Cit-PABC moiety is employed in the linker-conjugate.

In a preferred embodiment of the linker-conjugate according to formula (4a) and (4b), spacer moieties $Sp^1$, $Sp^2$, $Sp^3$ and $Sp^4$, if present, are independently selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups and $C_9$-$C_{200}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. When the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are interrupted by one or more heteroatoms as defined above, it is preferred that said groups are interrupted by one or more O-atoms, and/or by one or more S—S groups.

More preferably, spacer moieties $Sp^1$, $Sp^2$, $Sp^3$ and $Sp^4$, if present, are independently selected from the group consisting of linear or branched $C_1$-$C_{100}$ alkylene groups, $C_2$-$C_{100}$ alkenylene groups, $C_2$-$C_{100}$ alkynylene groups, $C_3$-$C_{100}$ cycloalkylene groups, $C_5$-$C_{100}$ cycloalkenylene groups, $C_5$-$C_{100}$ cycloalkynylene groups, $C_7$-$C_{100}$ alkylarylene groups, $C_7$-$C_{100}$ arylalkylene groups, $C_5$-$C_{100}$ arylalkenylene groups and $C_9$-$C_{100}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. Even more preferably, spacer moieties $Sp^1$, $Sp^2$, $Sp^3$ and $Sp^4$, if present, are independently selected from the group consisting of linear or branched $C_1$-$C_{50}$ alkylene groups, $C_2$-$C_{50}$ alkenylene groups, $C_2$-$C_{50}$ alkynylene groups, $C_3$-$C_{50}$ cycloalkylene groups, $C_5$-$C_{50}$ cycloalkenylene groups, $C_5$-$C_{50}$ cycloalkynylene groups, $C_7$-$C_{50}$ alkylarylene groups, $C_7$-$C_{50}$ arylalkylene groups, $C_5$-$C_{50}$ arylalkenylene groups and $C_9$-$C_{50}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. Yet even more preferably, spacer moieties $Sp^1$, $Sp^2$, $Sp^3$ and $Sp^4$, if present, are independently selected from the group consisting of linear or branched $C_1$-$C_{20}$ alkylene groups, $C_2$-$C_{20}$ alkenylene groups, $C_2$-$C_{20}$ alkynylene groups, $C_3$-$C_{20}$ cycloalkylene groups, $C_5$-$C_{20}$ cycloalkenylene groups, $C_8$-$C_{20}$ cycloalkynylene groups, $C_7$-$C_{20}$ alkylarylene groups, $C_7$-$C_{20}$ arylalkylene groups, $C_8$-$C_{20}$ arylalkenylene groups and $C_9$-$C_{20}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. In these preferred embodiments it is further preferred that the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are unsubstituted and optionally interrupted by one or more heteroatoms selected from the group of O, S and $NR^3$, preferably O, wherein $R^3$ is independently selected from the group consisting of hydrogen and $C_1$-$C_4$ alkyl groups, preferably hydrogen or methyl.

Most preferably, spacer moieties $Sp^1$, $Sp^2$, $Sp^3$ and $Sp^4$, if present, are independently selected from the group consisting of linear or branched $C_1$-$C_{20}$ alkylene groups, the alkylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. In this embodiment, it is further preferred that the alkylene groups are unsubstituted and optionally interrupted by one or more heteroatoms selected from the group of O, S and $NR^3$, preferably O and/or S, wherein $R^3$ is independently selected from the group consisting of hydrogen and $C_1$-$C_4$ alkyl groups, preferably hydrogen or methyl.

Preferred spacer moieties $Sp^1$, $Sp^2$, $Sp^3$ and $Sp^4$ thus include $-(CH_2)_n-$, $-(CH_2CH_2)_n-$, $-(CH_2CH_2O)_n-$, $-(OCH_2CH_2)_n-$, $-(CH_2CH_2O)_nCH_2CH_2-$, $-CH_2CH_2(OCH_2CH_2)_n-$, $-(CH_2CH_2CH_2O)_n-$, $-(OCH_2CH_2CH_2)_n-$, $-(CH_2CH_2CH_2O)_nCH_2CH_2-$ and $-CH_2CH_2CH_2(OCH_2CH_2CH_2)_n-$, wherein n is an integer in the range of 1 to 50, preferably in the range of 1 to 40, more preferably in the range of 1 to 30, even more preferably in the range of 1 to 20 and yet even more preferably in the range of 1 to 15. More preferably n is 1, 2, 3, 4, 5, 6, 7, 8, 9 or 10, more preferably 1, 2, 3, 4, 5, 6, 7 or 8, even more preferably 1, 2, 3, 4, 5 or 6, yet even more preferably 1, 2, 3 or 4.

Since $Sp^1$, $Sp^2$, $Sp^3$ and $Sp^4$ are independently selected, $Sp^1$, if present, may be different from $Sp^2$, if present, from $Sp^3$ and/or from $Sp^4$, if present.

Reactive groups $Q^1$ are described in more detail above. In the linker-conjugate according to formula (4a) and (4b), it is preferred that reactive group $Q^1$ is selected from the group consisting of, optionally substituted, N-maleimidyl groups, halogenated N-alkylamido groups, sulfonyloxy N-alkylamido groups, ester groups, carbonate groups, sulfonyl halide groups, thiol groups or derivatives thereof, alkenyl groups, alkynyl groups, (hetero)cycloalkynyl groups, bicyclo[6.1.0]non-4-yn-9-yl] groups, cycloalkenyl groups, tetrazinyl groups, azido groups, phosphine groups, nitrile oxide groups, nitrone groups, nitrile imine groups, diazo groups, ketone groups, (O-alkyl)hydroxylamino groups, hydrazine groups, halogenated N-maleimidyl groups, carbonyl halide groups, allenamide groups and 1,1-bis(sulfonylmethyl) methylcarbonyl groups or elimination derivatives thereof. In a further preferred embodiment, $Q^1$ is according to formula (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj) or (9zk), wherein (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zo) and preferred embodiments thereof, are as defined above. In a preferred embodiment, $Q^1$ is according to formula (9a), (9b), (9c), (9f), (9j), (9n), (9o), (9p), (9q), (9s), (9t), (9zh), (9zo) or (9r). In an even further preferred embodiment, $Q^1$ is according to formula (9a), (9j), (9n), (9o), (9q), (9p), (9t), (9zh), (9zo) or (9s), and in a particularly preferred embodiment, $Q^1$ is according to formula (9a), (9q), (9n), (9o), (9p), (9t), (9zo) or (9zh), and preferred embodiments thereof, as defined above.

Target molecule D and preferred embodiments for target molecule D in the linker-conjugate according to formula (4a) and (4b) are as defined above.

As described above, $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is D, -[(Sp$^1$)$_b$(Z$^2$)$_e$(Sp$^4$)$_i$D] or -[(Sp$^2$)$_c$(Z$^1$)$_d$(Sp$^3$)$_g$Q$^1$], wherein D is a further target molecule and $Sp^1$, $Sp^2$, $Sp^3$, $Sp^4$, $Z^1$, $Z^2$, $Q^1$, b, c, d, e, g and i are as defined above.

In a preferred embodiment, $R^1$ is hydrogen or a $C_1$-$C_{20}$ alkyl group, more preferably $R^1$ is hydrogen or a $C_1$-$C_{16}$ alkyl group, even more preferably $R^1$ is hydrogen or a $C_1$-$C_0$ alkyl group, wherein the alkyl group is optionally substituted and optionally interrupted by one or more heteroatoms selected from O, S and $NR^3$, preferably O, wherein $R^3$ is independently selected from the group consisting of hydrogen and $C_1$-$C_4$ alkyl groups. In a further preferred embodiment, $R^1$ is hydrogen. In another further preferred embodiment, $R^1$ is a $C_1$-$C_{20}$ alkyl group, more preferably a $C_1$-$C_{16}$ alkyl group, even more preferably a $C_1$-$C_{10}$ alkyl group, wherein the alkyl group is optionally interrupted by one or more O-atoms, and wherein the alkyl group is optionally substituted with an —OH group, preferably a terminal —OH group. In this embodiment it is further preferred that $R^1$ is a polyethyleneglycol chain comprising a terminal —OH group. In another further preferred embodiment, $R^1$ is a $C_1$-$C_{12}$ alkyl group, more preferably a $C_1$-$C_6$ alkyl group, even more preferably a $C_1$-$C_4$ alkyl group, and yet even more preferably $R^1$ is selected from the group consisting of methyl, ethyl, n-propyl, i-propyl, n-butyl, s-butyl and t-butyl.

In another preferred embodiment, $R^1$ is a further target molecule D, -[(Sp$^1$)$_b$(Z$^2$)$_e$(Sp$^4$)$_i$D] or -[(Sp$^2$)$_c$(Z$^1$)$_d$(Sp$^3$)$_g$Q$^1$], wherein D is a target molecule and $Sp^1$, $Sp^2$, $Sp^3$, $Sp^4$, $Z^1$, $Z^2$, $Q^1$, b, c, d, e, g and i are as defined above. When $R^1$ is D or -[(Sp$^1$)$_b$(Z$^2$)$_e$(Sp$^4$)$_i$D], it is further preferred that the linker-conjugate is according to formula (4a). In this embodiment, linker-conjugate (4a) comprises two target molecules D, which may be the same or different. When $R^1$ is -[(Sp$^1$)$_b$(Z$^2$)$_e$(Sp$^4$)$_i$D], $Sp^1$, b, $Z^2$, e, $Sp^4$, i and D in -[(Sp$^1$)$_b$(Z$^2$)$_e$(Sp$^4$)$_i$D] may be the same or different from $Sp^1$, b, $Z^2$, e, $Sp^4$, i and D in -[(Sp$^1$)$_b$(Z$^2$)$_e$(Sp$^4$)$_i$D] that is attached to the N-atom of $N(R^1)$. In a preferred embodiment, both -[(Sp$^1$)$_b$(Z$^2$)$_e$(Sp$^4$)$_i$D] and -[(Sp$^1$)$_b$(Z$^2$)$_e$(Sp$^4$)$_i$D] on the N-atom of $N(R^1)$ are the same.

When $R^1$ is -[(Sp$^2$)$_c$(Z$^1$)$_d$(Sp$^3$)$_g$Q$^1$], it is further preferred that the linker-conjugate is according to formula (4b). In this embodiment, linker-conjugate (4b) comprises two target molecules $Q^1$, which may be the same or different. When $R^1$ is -[(Sp$^2$)$_c$(Z$^1$)$_d$(Sp$^3$)$_g$Q$^1$], $Sp^2$, c, $Z^1$, d, $Sp^3$, g and D in -[(Sp$^1$)$_b$(Z$^2$)$_e$(Sp$^4$)$_i$D] may be the same or different from $Sp^1$, b, $Z^2$, e, $Sp^4$, i and $Q^1$ in the other -[(Sp$^2$)$_c$(Z$^1$)$_d$(Sp$^3$)$_g$Q$^1$] that is attached to the N-atom of $N(R^1)$. In a preferred embodiment, -[(Sp$^2$)$_c$(Z$^1$)$_d$(Sp$^3$)$_g$Q$^1$] groups on the N-atom of $N(R^1)$ are the same.

In the linker-conjugate according to formula (4a) and (4b), f is an integer in the range of 1 to 150. The linker-conjugate may thus comprise more than one group according to formula (1), the group according to formula (1) being as defined above. When more than one group according to formula (1) is present, i.e. when f is 2 or more, then a, b, $Sp^1$ and $R^1$ are independently selected. In other words, when f is 2 or more, each a is independently 0 or 1, each b is independently 0 or 1, each $Sp^1$ may be the same or different and each $R^1$ may be the same or different. In a preferred embodiment, f is an integer in the range of 1 to 100, preferably in the range of 1 to 50, more preferably in the range of 1 to 25, and even more preferably in the range of 1 to 15. More preferably, f is 1, 2, 3, 4, 5, 6, 7, 8, 9 or 10, even more preferably f is 1, 2, 3, 4, 5, 6, 7 or 8, yet even more preferably f is 1, 2, 3, 4, 5 or 6, yet even more preferably f is 1, 2, 3 or 4, and most preferably f is 1 in this embodiment. In another preferred embodiment, f is an integer in the range of 2 to 150, preferably in the range of 2 to 100, more preferably in the range of 2 to 50, more preferably in the range of 2 to 25, and even more preferably in the range of 2 to 15. More preferably, f is 2, 3, 4, 5, 6, 7, 8, 9 or 10, even more preferably f is 2, 3, 4, 5, 6, 7 or 8, yet even more preferably f is 2, 3, 4, 5 or 6, yet even more preferably f is 2, 3 or 4, and most preferably f is 2 in this embodiment.

As described above, in a preferred embodiment, a is 0 in the compound according to formula (4a) or (4b). The linker-conjugate may therefore also be a compound according to formula (6a) or (6b), or a salt thereof:

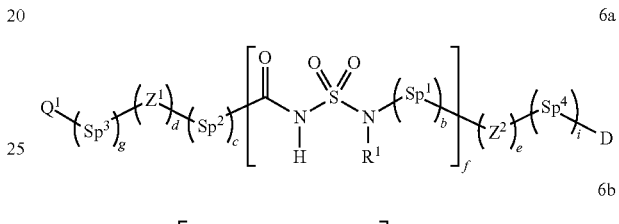

wherein a, b, c, d, e, f, g, i, D, $Q^1$, $Sp^1$, $Sp^2$, $Sp^3$, $Sp^4$, $Z^1$, $Z^2$ and $R^1$, and their preferred embodiments, are as defined above for (4a) and (4b).

As described above, in another preferred embodiment, a is 1 in the compound according to formula (4a) or (4b). The linker-conjugate may therefore also be a compound according to formula (7a) or (7b), or a salt thereof:

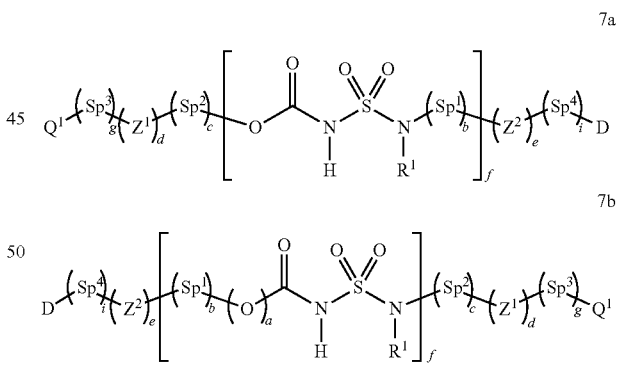

wherein a, b, c, d, e, f, g, i, D, $Q^1$, $Sp^1$, $Sp^2$, $Sp^3$, $Sp^4$, $Z^1$, $Z^2$ and $R^1$, and their preferred embodiments, are as defined above for (4a) and (4b).

When $Sp^4$ is absent in the linker-conjugate according to formula (4a), i.e. when i is 0, D is linked to $Z^2$ (when e is 1), to $Sp^1$ (when e is 0 and b is 1) or to $N(R^1)$ (when e is 0 and b is 0). When $Sp^4$ is absent in the linker-conjugate according to formula (4b), i.e. when i is 0, D is linked to $Z^2$ (when e is 1), to $Sp^1$ (when e is 0 and b is 1), to the O-atom (when a is 1 and b and e are 0) or to the C(O) group (when a is 0 and b and e are 0). The linker-conjugate therefore also may be a compound according to formula (4c) or (4d), or a salt thereof:

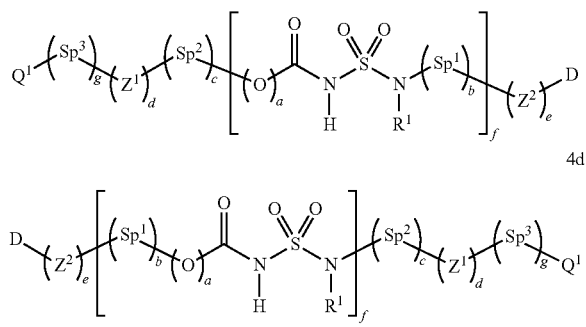

wherein a, b, c, d, e, f, g, D, $Q^1$, $Sp^1$, $Sp^2$, $Sp^3$, $Z^1$, $Z^2$ and $R^1$, and their preferred embodiments, are as defined above for (4a) and (4b).

In a preferred embodiment, in the linker-conjugate according to formula (4c) or (4d), a is 0. In another preferred embodiment, in the linker-conjugate according to formula (4c) or (4d), a is 1.

In a specific embodiment of the linker-conjugate, particularly a linker-conjugate according to formula (4a), (4b), (4c), (4d), (6a), (6b), (7a) or (7b), $Sp^1$, $Sp^2$ $Sp^3$ and $Sp^4$, if present, are independently selected from the group consisting of linear or branched $C_1$-$C_{20}$ alkylene groups, the alkylene groups being optionally substituted and optionally interrupted by one or more heteroatoms selected from the group consisting of O, S and $NR^3$, wherein $R^3$ is independently selected from the group consisting of hydrogen and $C_1$-$C_4$ alkyl groups, and $Q^1$ is according to formula (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg) (9zh), (9zi), (9zj) or (9zk), wherein (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zo) and preferred embodiments thereof, are as defined above. In a preferred embodiment, $Q^1$ is according to formula (9a), (9b), (9c), (9f), (9j), (9n), (9o), (9p), (9q), (9s) (9t), (9zh), (9zo) or (9r). In an even further preferred embodiment, $Q^1$ is according to formula (9a), (9j), (9n), (9o), (9p), (9q), (9t), (9zh), (9zo) or (9s), and in a particularly preferred embodiment, $Q^1$ is according to formula (9a), (9q), (9n), (9p), (9t), (9zh), (9zo) or (9o), and preferred embodiments thereof, as defined above.

Linker L, as preferably comprised in the linker-conjugate according to formula (4a), (4b), (4c), (4d), (6a), (6b), (7a) or (7b) as defined above, linker as defined above may be represented by formula (8a) and (8b), respectively:

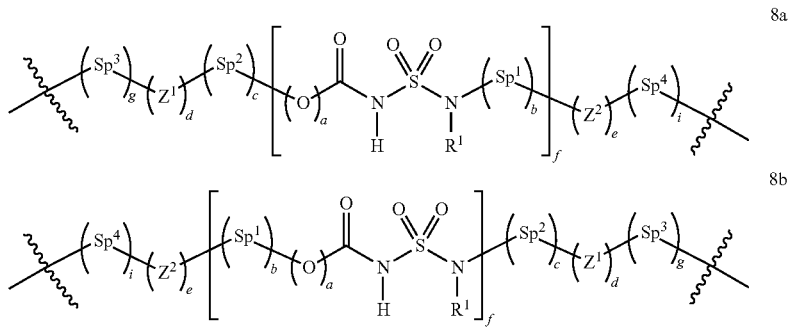

As will be understood by the person skilled in the art, preferred embodiments of spacer-moieties (8a) and (8b) may depend on e.g. the nature of reactive groups $Q^1$ and D in the linker-conjugate, the synthetic method to prepare the linker-conjugate (e.g. the nature of complementary functional group $F^2$ on a target molecule), the nature of a bioconjugate that is prepared using the linker-conjugate (e.g. the nature of complementary functional group $F^1$ on the biomolecule).

When $Q^1$ is for example a cyclooctynyl group according to formula (9n), (9o), (9p), (9q) or (9zk) as defined above, then preferably $Sp^3$ is present (g is 1).

When for example the linker-conjugate was prepared via reaction of a reactive group $Q^2$ that is a cyclooctynyl group according to formula (9n), (9o), (9p), (9q) or (9zk) with an azido functional group $F^2$, then preferably $Sp^4$ is present (i is 1).

Furthermore, it is preferred that at least one of $Sp^1$, $Sp^2$, $Sp^3$ and $Sp^4$ is present, i.e. at least one of b, c, g, and i is not 0. In another preferred embodiment, at least one of $Sp^1$ and $Sp^4$ and at least one of $Sp^2$ and $Sp^3$ are present.

When f is 2 or more, it is preferred that $Sp^1$ is present (b is 1).

These preferred embodiments of the linker-moiety (8a) and (8b) also hold for the linker-conjugate when comprised in the bioconjugates according to the invention as described in more detail below.

Preferred embodiments of $Sp^1$, $Sp^2$, $Sp^3$ and $Sp^4$ are as defined above.

Biomolecule

The biomolecule is represented by B—$F^1$, wherein B is a biomolecule and $F^1$ is a functional group capable of reacting with reactive group $Q^1$ on the linker-conjugate and "—" is a bond or a spacer moiety. In one embodiment, "—" is a spacer moiety as defined herein. In one embodiment, "—" is a bond, typically a covalent bond. The biomolecule may also be referred to as "biomolecule of interest" (BOI). The biomolecule may be a biomolecule as naturally occurring, wherein functional group $F^1$ is a already present in the biomolecule of interest, such as for example a thiol, an amine, an alcohol or a hydroxyphenol unit. Conjugation with the linker-conjugate then occurs via the first approach as defined above. Alternatively, the biomolecule may be a modified biomolecule, wherein functional group $F^1$ is specifically incorporated into the biomolecule of interest and conjugation with the linker-conjugate occurs via this engineered functionality, i.e. the two-stage approach of bioconjugation as defined above. Such modification of biomolecules to incorporate a specific functionality is known, e.g. from WO 2014/065661, incorporated herein by reference in its entirety. In the bioconjugate according to the invention, biomolecule B is preferably selected from the group consisting of proteins (including glycoproteins and antibodies), polypeptides, peptides, glycans, lipids, nucleic acids, oligonucleotides, polysaccharides, oligosaccharides, enzymes, hormones, amino acids and monosaccharides. More preferably, biomolecule B is selected from the group consisting of proteins (including glycoproteins and antibodies), polypeptides, peptides, glycans, nucleic acids, oligonucleotides, polysaccharides, oligosaccharides and enzymes. More preferably, biomolecule B is selected from the group consisting of proteins, including glycoproteins and antibodies, polypeptides, peptides and glycans. Most preferably, biomolecule B is an antibody or an antigen-binding fragment thereof.

Functional group $F^1$ is capable of reacting with reactive group $Q^1$ on the linker-conjugate to form a connecting group $Z^3$. To a skilled person, it is clear which functional group $F^1$ is capable of reacting with a complementary reactive group $Q^1$. Functional groups $F^1$ that are complementary to reactive groups $Q^1$, as defined above, and known to a person skilled in the art, are described in more detail below. Some representative examples of reaction between $F^1$ and $Q^1$ and their corresponding products comprising connecting group $Z^3$ are depicted in FIG. 11.

In the process for the preparation of a bioconjugate according to the invention, a reactive group $Q^1$ that is present in the linker-conjugate is typically reacted with functional group $F^1$. More than one functional group $F^1$ may be present in the biomolecule. When two or more functional groups are present, said groups may be the same or different. In another preferred embodiment, the biomolecule comprises two or more functional groups F, which may be the same or different, and two or more functional groups react with a complementary reactive group Q of a linker-conjugate.

For example a biomolecule comprising two functional groups F, i.e. $F^1$ and $F^2$, may react with two linker-conjugates comprising a functional group $Q^1$, which may be the same or different, to form a bioconjugate.

Examples of a functional group $F^1$ in a biomolecule comprise an amino group, a thiol group, a carboxylic acid, an alcohol group, a carbonyl group, a phosphate group, or an aromatic group. The functional group in the biomolecule may be naturally present or may be placed in the biomolecule by a specific technique, for example a (bio)chemical or a genetic technique. The functional group that is placed in the biomolecule may be a functional group that is naturally present in nature, or may be a functional group that is prepared by chemical synthesis, for example an azide, a terminal alkyne, a cyclopropene moiety or a phosphine moiety. In view of the preferred mode of conjugation by cycloaddition, it is preferred that $F^1$ is group capable of reacting in a cycloaddition, such as a diene, a dienophile, a 1,3-dipole or a dipolarophile, preferably $F^1$ is selected from a 1,3-dipole (typically an azido group, nitrone group, nitrile oxide group, nitrile imine group or diazo group) or a dipolarophile (typically an alkenyl or alkynyl group). Herein, $F^1$ is a 1,3-dipole when $Q^1$ is a dipolarophile and $F^1$ is a dipolarophile when $Q^1$ is a 1,3-dipole, or $F^1$ is a diene when $Q^1$ is a dienophile and $F^1$ is a dienophile when $Q^1$ is a diene. Most preferably, $F^1$ is a 1,3-dipole, preferably $F^1$ is or comprises an azido group.

Several examples of a functional group that is placed into a biomolecule are shown in FIG. 2. FIG. 2 shows several structures of derivatives of UDP sugars of galactosamine, which may be modified with e.g. a thiopropionyl group (11a), an azidoacetyl group (11b), or an azidodifluoroacetyl group (11c) at the 2-position, or with an azido group at the 6-position of N-acetyl galactosamine (11d). In one embodiment, functional group $F^1$ is a thiopropionyl group, an azidoacetyl group, or an azidodifluoroacetyl group.

FIG. 3 schematically displays how any of the UDP-sugars 11a-d may be attached to a glycoprotein comprising a GlcNAc moiety 12 (e.g. a monoclonal antibody the glycan of which is trimmed by an endoglycosidase) under the action of a galactosyltransferase mutant or a GalNAc-transferase, thereby generating a β-glycosidic 1-4 linkage between a GalNAc derivative and GlcNAc (compounds 13a-d, respectively).

Preferred examples of naturally present functional groups $F^1$ include a thiol group and an amino group. Preferred examples of a functional group that is prepared by chemical synthesis for incorporation into the biomolecule include a ketone group, a terminal alkyne group, an azide group, a cyclo(hetero)alkyne group, a cyclopropene group, or a tetrazine group.

As was described above, complementary reactive groups $Q^1$ and functional groups $F^1$ are known to a person skilled in the art, and several suitable combinations of $Q^1$ and $F^1$ are described above, and shown in FIG. 11. A list of complementary groups $Q^1$ and $F^1$ is disclosed in Table 3.1, pages 230-232 of Chapter 3 of G. T. Hermanson, "*Bioconjugate Techniques*", Elsevier, $3^{rd}$ Ed. 2013 (ISBN:978-0-12-382239-0), and the content of this Table is expressly incorporated by reference herein.

Bioconjugate

A bioconjugate is herein defined as a compound wherein a biomolecule is covalently connected to a target molecule D via a linker. A bioconjugate comprises one or more biomolecules and/or one or more target molecules. The linker may comprise one or more spacer moieties. The bioconjugate according to the invention is conveniently prepared by the process for preparation of a bioconjugate according to the invention, wherein the linker-conjugate comprising reactive group $Q^1$ is conjugated to a biomolecule comprising functional group F. In this conjugation reaction, groups $Q^1$ and $F^1$ react with each other to form a connecting group $Z^3$ which connects the target molecule D with the biomolecule B. All preferred embodiments described herein for the linker-conjugate and the biomolecule thus equally apply to the bioconjugate according to the invention, except for all said for $Q^1$ and F, wherein the bioconjugate according to the invention contains the reaction product of $Q^1$ and $F^1$, i.e. connecting group $Z^3$.

The bioconjugate according to the invention has formula (A):

B-L-D  (A), wherein:
B is a biomolecule;
L is a linker linking B and D;
D is a target molecule; and
each occurrence of "—" is independently a bond or a spacer moiety,
wherein L comprises a group according to formula (1) or a salt thereof:

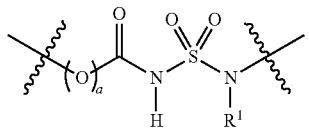

wherein:
a is 0 or 1; and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups; or $R^1$ is a target molecule D, wherein D is optionally connected to N via a spacer moiety.

In one embodiment, "—" is a spacer moiety as defined herein. In one embodiment, "—" is a bond, typically a covalent bond.

In a preferred embodiment, the bioconjugate is presented by B—$Z^3$-L-D, wherein B, L, D and "—" are as defined above and $Z^3$ is a connecting group which is obtainable by reaction of $Q^1$ with $F^1$. Preferably, moiety $Z^3$ is obtainable by a cycloaddition, preferably a 1,3-dipolar cycloaddition reaction, most preferably $Z^3$ is a 1,2,3-triazole ring, which is located in a spacer moiety, preferably the spacer moiety between B and L, most preferably between B and the carbonyl or carboxyl end of the group according to formula (1).

When the bioconjugate according to the invention comprises a salt of the group according to formula (1), the salt is preferably a pharmaceutically acceptable salt.

The bioconjugate according to the invention may comprise more than one target molecule.

Similarly, the bioconjugate may comprise more than one biomolecule. Biomolecule B and target molecule D, and preferred embodiments thereof, are described in more detail above. Preferred embodiments for D in the bioconjugate according to the invention correspond to preferred embodiments of D in the linker-conjugate according to the invention as were described in more detail above. Preferred embodiments for the linker (8a) or (8b) in the bioconjugate according to the invention correspond to preferred embodiments of the linker in the linker-conjugate, as were described in more detail above. Preferred embodiments for B in the bioconjugate according to the invention correspond to preferred embodiments of B in the biomolecule according to the invention as were described in more detail above.

The bioconjugate according to the invention may also be defined as a bioconjugate wherein a biomolecule is conjugated to a target molecule via a spacer-moiety, wherein the spacer-moiety comprises a group according to formula (1), or a salt thereof, wherein the group according to formula (1) is as defined above.

The bioconjugate according to the invention may also be denoted as $(B)_y Sp(D)_z$, wherein y is an integer in the range of 1 to 10 and z is an integer in the range of 1 to 10.

The invention thus also relates to a bioconjugate according to the formula:

$(B)_y Sp(D)_z$, wherein:
y is an integer in the range of 1 to 10;
z is an integer in the range of 1 to 10;
B is a biomolecule;
D is a target molecule;
Sp is a spacer moiety, wherein a spacer moiety is defined as a moiety that spaces (i.e. provides a certain distance between) and covalently links biomolecule B and target molecule D; and wherein said spacer moiety comprises a group according to formula (1) or a salt thereof, wherein the group according to formula (1) is as defined above.

In a preferred embodiment, said spacer moiety further comprises a moiety that is obtainable by a cycloaddition, preferably a 1,3-dipolar cycloaddition reaction, most preferably a 1,2,3-triazole ring, which is located between B and said group according to formula (1).

Preferably, y is 1, 2, 3 or 4, more preferably y is 1 or 2 and most preferably, y is 1. Preferably, z is 1, 2, 3, 4, 5 or 6, more preferably z is 1, 2, 3 or 4, even more preferably z is 1, 2 or 3, yet even more preferably z is 1 or 2 and most preferably z is 1. More preferably, y is 1 or 2, preferably 1, and z is 1, 2, 3 or 4, yet even more preferably y is 1 or 2, preferably 1, and z is 1, 2 or 3, yet even more preferably y is 1 or 2, preferably 1, and z is 1 or 2, and most preferably y is 1 and z is 1. In a preferred embodiment, the bioconjugate is according to the formula $BSp(D)_4$, $BSp(D)_3$, $BSp(D)_2$ or BSpD.

As described above, the bioconjugate according to the invention comprises a group according to formula (1) as defined above, or a salt thereof. In a preferred embodiment, the bioconjugate comprises a group according to formula (1) wherein a is 0, or a salt thereof. In this embodiment, the bioconjugate thus comprises a group according to formula (2) or a salt thereof, wherein (2) is as defined above.

In another preferred embodiment, the bioconjugate comprises a group according to formula (1) wherein a is 1, or a salt thereof. In this embodiment, the bioconjugate thus comprises a group according to formula (3) or a salt thereof, wherein (3) is as defined above.

In the bioconjugate according to the invention, $R^1$, spacer moiety Sp, as well as preferred embodiments of $R^1$ and Sp, are as defined above for the linker-conjugate according to the invention. In a preferred embodiment, the bioconjugate is according to formula (5a) or (5b), or a salt thereof:

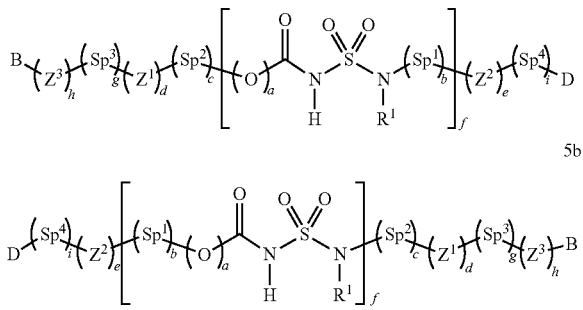

wherein
a, b, c, d, e, f, g, h, i, D, $Sp^1$, $Sp^2$, $Sp^3$, $Sp^4$, $Z^1$, $Z^2$, $Z^3$ and $R^1$, and preferred embodiments thereof, are as defined above for linker-conjugate (4a) and (4b); and
h is 0 or 1;
$Z^3$ is a connecting group that connects B to $Sp^3$, $Z^1$, $Sp^2$, O or C(O); and
B is a biomolecule.
Preferably, h is 1.

Preferred embodiments of biomolecule B are as defined above.

When the bioconjugate according to the invention is a salt of (5a) or (5b), the salt is preferably a pharmaceutically acceptable salt.

$Z^3$ is a connecting group. As described above, the term "connecting group" herein refers to the structural element connecting one part of a compound and another part of the same compound. Typically, a bioconjugate is prepared via reaction of a reactive group $Q^1$ present in the linker-conjugate with a functional group $F^1$ present in a biomolecule. As will be understood by the person skilled in the art, the nature of connecting group $Z^3$ depends on the type of organic reaction that was used to establish the connection between the biomolecule and the linker-conjugate. In other words, the nature of $Z^3$ depends on the nature of reactive group $Q^1$ of the linker-conjugate and the nature of functional group $F^1$ in the biomolecule. Since there is a large number of different chemical reactions available for establishing the connection between a biomolecule and a linker-conjugate, consequently there is a large number of possibilities for $Z^3$.

Several examples of suitable combinations of $F^1$ and $Q^1$, and of connecting group $Z^3$ that will be present in a bioconjugate when a linker-conjugate comprising $Q^1$ is conjugated to a biomolecule comprising a complementary functional group $F^1$, are shown in FIG. 11.

When $F^1$ is for example a thiol group, complementary groups $Q^1$ include N-maleimidyl groups and alkenyl groups, and the corresponding connecting groups $Z^3$ are as shown in FIG. 11. When $F^1$ is a thiol group, complementary groups $Q^1$ also include allenamide groups.

When $F^1$ is for example an amino group, complementary groups $Q^1$ include ketone groups and activated ester groups, and the corresponding connecting groups $Z^3$ are as shown in FIG. 11.

When $F^1$ is for example a ketone group, complementary groups $Q^1$ include (O-alkyl)hydroxylamino groups and hydrazine groups, and the corresponding connecting groups $Z^3$ are as shown in FIG. 11.

When $F^1$ is for example an alkynyl group, complementary groups $Q^1$ include azido groups, and the corresponding connecting group $Z^3$ is as shown in FIG. 11.

When $F^1$ is for example an azido group, complementary groups $Q^1$ include alkynyl groups, and the corresponding connecting group $Z^3$ is as shown in FIG. 11.

When $F^1$ is for example a cyclopropenyl group, a trans-cyclooctene group or a cyclooctyne group, complementary groups $Q^1$ include tetrazinyl groups, and the corresponding connecting group $Z^3$ is as shown in FIG. 11. In these particular cases, $Z^3$ is only an intermediate structure and will expel $N_2$, thereby generating a dihydropyridazine (from the reaction with alkene) or pyridazine (from the reaction with alkyne).

Additional suitable combinations of $F^1$ and $Q^1$, and the nature of resulting connecting group $Z^3$ are known to a person skilled in the art, and are e.g. described in G. T. Hermanson, "Bioconjugate Techniques", Elsevier, 3$^{rd}$ Ed. 2013 (ISBN:978-0-12-382239-0), in particular in Chapter 3, pages 229-258, incorporated by reference. A list of complementary reactive groups suitable for bioconjugation processes is disclosed in Table 3.1, pages 230-232 of Chapter 3 of G. T. Hermanson, "Bioconjugate Techniques", Elsevier, 3$^{rd}$ Ed. 2013 (ISBN:978-0-12-382239-0), and the content of this Table is expressly incorporated by reference herein.

In the bioconjugate according to (5a) and (5b), it is preferred that at least one of $Z^3$, $Sp^3$, $Z^1$ and $Sp^2$ is present, i.e. at least one of h, g, d and c is not 0. It is also preferred that at least one of $Sp^1$, $Z^2$ and $Sp^4$ is present, i.e. that at least one of b, e and i is not 0. More preferably, at least one of $Z^3$, $Sp^3$, $Z^1$ and $Sp^2$ is present and at least one of $Sp^1$, $Z^2$ and $Sp^4$ is present, i.e. it is preferred that at least one of b, e and i is not 0 and at least one of h, g, d and c is not 0.

Process for the Preparation of a Bioconjugate

In the various aspects of the present invention, the bioconjugate according to the invention is typically obtained by a process for the preparation of a bioconjugate as defined herein. As the presence of the group according to formula (1) or a salt thereof in linker L of the bioconjugate is key in the present invention, any method of preparing the bioconjugate can be used as long as the obtained bioconjugate comprises linker L as defined herein. The group according to formula (1) may be present in linker L between B and $Z^3$, i.e. it originates form the biomolecule, or between $Z^3$ and D, i.e. it originates from the linker-conjugate, or $Z^3$ is or comprises the group according to formula (1), i.e. the group according to formula (1) is formed upon conjugation. Preferably, the group according to formula (1) is present in linker L between B and $Z^3$ or between $Z^3$ and D, most preferably, the group according to formula (1) is present in linker L between $Z^3$ and D. Likewise, the exact mode of conjugation, including the nature of $Q^1$ and $F^1$ have a great flexibility in the context of the present invention. Many techniques for conjugating BOIs to MOIs are known to a person skilled in the art and can be used in the context of the present invention. Conjugation occurs under condition such that reactive group $Q^1$ is reacted with the functional group $F^1$ of the biomolecule to covalently link the biomolecule to the linker-conjugate.

In one embodiment, the mode of conjugation is selected from any of the conjugation modes depicted in FIG. 11, i.e. from thiol-alkene conjugation (preferably cysteine-alkene conjugation, preferably wherein the alkene is a pendant alkene (—C=$CH_2$) or a maleimide moiety, most preferably a maleimide moiety) to from a connecting moiety $Z^3$ that may be represented as (10a) or (10b), amino-(activated) carboxylic acid conjugation (wherein the (activated) carboxylic acid is represented by —C(O)X, wherein X is a leaving group) to from a connecting moiety $Z^3$ that may be represented as (10c), ketone-hydrazino conjugation (preferably acetyl-hydrazino conjugation) to from a connecting moiety $Z^3$ that may be represented as (10d) wherein Y═NH, ketone-oxyamino conjugation (preferably acetyl-oxyamino conjugation) to from a connecting moiety $Z^3$ that may be represented as (10d) wherein Y═O, alkyne-azide conjugation (preferably wherein the alkyne is a pendant alkyne (—C—CH) or a cyclooctyne moiety, most preferably a cyclooctyne moiety) to from a connecting moiety $Z^3$ that may be represented as (10e), (10f), (10i), (10g), (10j) or (10k), preferably (10e), (10f) or (10g), alkene-1,2,4,5-tetrazine conjugation or alkyne-1,2,4,5-tetrazine conjugation to from a connecting moiety $Z^3$ that may be represented as (10h) from which $N_2$ will eliminate, giving dihydropyridazine products. Especially preferred conjugation modes are cysteine-alkene conjugation and alkyne-azide conjugation, more preferably cysteine-maleimide conjugation and cyclooctyne-azide conjugation.

In one embodiment, the conjugation mode is a(n) (cyclo) alkyne-azide conjugation to from a connecting moiety $Z^3$ that is represented by (10e), (10i), (10g), (10j) or (10k), preferably by (10e), (10i), (10g), most preferably by (10g), as represented by:

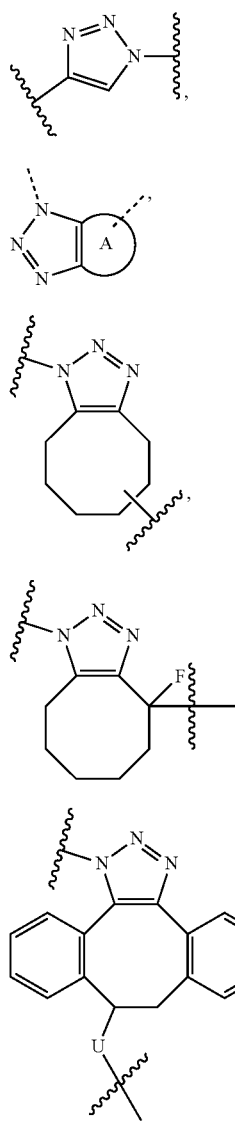

10e

10i

10g

10j

10k wherein cycle A is a 7-10-membered (hetero)cyclic moiety. Connecting moieties (10e), (10j) and (10k) may exist in either one of the possible two regioisomers.

The bioconjugate according to the invention is typically prepared by a process comprising the step of reacting a reactive group $Q^1$ of the linker-conjugate as defined herein with a functional group $F^1$ of the biomolecule, also referred to as a biomolecule. The linker-conjugate and the biomolecule, and preferred embodiments thereof, are described in more detail above. Such a process is known to a person skilled in the art as conjugation or bioconjugation. FIG. 1 shows the general concept of conjugation of biomolecules: a biomolecule of interest (BOI) comprising one or more functional groups $F^1$ is incubated with (excess of) a target molecule D (also referred to as molecule of interest or MOI), covalently attached to a reactive group $Q^1$ via a specific linker. In the process of bioconjugation, a chemical reaction between $F^1$ and $Q^1$ takes place, thereby forming a bioconjugate comprising a covalent bond between the BOI and the MOI. The BOI may e.g. be a peptide/protein, a glycan or a nucleic acid.

The bioconjugation reaction typically comprises the step of reacting a reactive group $Q^1$ of the linker-conjugate with a functional group $F^1$ of a the biomolecule, wherein a bioconjugate of formula (A) is formed, wherein linker L comprises a group according to formula (1) or a salt thereof:

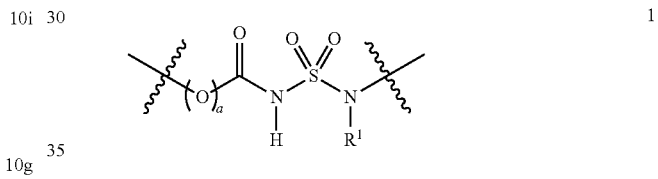

1 wherein:

a is 0 or 1; and $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a further target molecule D, which is optionally connected to N via a spacer moiety.

In a preferred embodiment, the bioconjugate is prepared via a cycloaddition, such as a (4+2)-cycloaddition (e.g. a Diels-Alder reaction) or a (3+2)-cycloaddition (e.g. a 1,3-dipolar cycloaddition).

Preferably, the conjugation is a Diels-Alder reaction or a 1,3-dipolar cycloaddition. The preferred Diels-Alder reaction is the inverse-electron demand Diels-Alder cycloaddition. In another preferred embodiment, the 1,3-dipolar cycloaddition is used, more preferably the alkyne-azide cycloaddition, and most preferably wherein $Q^1$ is or comprises an alkyne group and $F^1$ is an azido group. Cycloadditions, such as Diels-Alder reactions and 1,3-dipolar cycloadditions are known in the art, and the skilled person knows how to perform them.

When $Q^1$ reacts with F, a covalent connection between the biomolecule and the target molecule originating of the linker-conjugate is formed. Complementary reactive groups $Q^1$ and functional groups $F^1$ are described in more detail above and below.

In a preferred embodiment of the process for preparing the bioconjugate, a is 0 in the group according to formula (1). In this embodiment, the linker-conjugate thus comprises a group according to formula (2), as defined above. In another preferred embodiment of the process for preparing the bioconjugate, a is 1 in the group according to formula (1). In this embodiment, the linker-conjugate thus comprises a group according to formula (3), as defined above.

Biomolecules are described in more detail above. Preferably, in the process according to the invention the biomolecule is selected from the group consisting of proteins (including glycoproteins and antibodies), polypeptides, peptides, glycans, lipids, nucleic acids, oligonucleotides, polysaccharides, oligosaccharides, enzymes, hormones, amino acids and monosaccharides. More preferably, biomolecule B is selected from the group consisting of proteins (including glycoproteins and antibodies), polypeptides, peptides, glycans, nucleic acids, oligonucleotides, polysaccharides, oligosaccharides and enzymes. More preferably, biomolecule B is selected from the group consisting of proteins, including glycoproteins and antibodies, polypeptides, peptides and glycans. Most preferably, B is an antibody or an antigen-binding fragment thereof.

In the process for preparing the bioconjugate, it is preferred that reactive group $Q^1$ is selected from the group consisting of, optionally substituted, N-maleimidyl groups, halogenated N-alkylamido groups, sulfonyloxy N-alkylamido groups, ester groups, carbonate groups, sulfonyl halide groups, thiol groups or derivatives thereof, alkenyl groups, alkynyl groups, (hetero)cycloalkynyl groups, bicyclo[6.1.0]non-4-yn-9-yl] groups, cycloalkenyl groups, tetrazinyl groups, azido groups, phosphine groups, nitrile oxide groups, nitrone groups, nitrile imine groups, diazo groups, ketone groups, (O-alkyl)hydroxylamino groups, hydrazine groups, halogenated N-maleimidyl groups, 1,1-bis(sulfonylmethyl)methylcarbonyl groups or elimination derivatives thereof, carbonyl halide groups and allenamide groups.

In a further preferred embodiment, $Q^1$ is according to formula (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj) or (9zk), wherein (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zo), and preferred embodiments thereof, are as defined above for the linker-conjugate according to the invention. More preferably, $Q^1$ is according to formula (9a), (9b), (9c), (9f), (9j), (9n), (9o), (9p), (9q), (9s), (9t), (9ze), (9zh), (9zo) or (9r). Even more preferably, $Q^1$ is according to formula (9a), (9j), (9n), (9o), (9p), (9q), (9t), (9ze), (9zh), (9zo) or (9s), and most preferably, $Q^1$ is according to formula (9a), (9p), (9q), (9n), (9t), (9ze), (9zh), (9zo) or (9o), and preferred embodiments thereof, as defined above.

In an especially preferred embodiment, $Q^1$ comprises an alkyne group, preferably selected from the alkynyl group as described above, the cycloalkenyl group as described above, the (hetero)cycloalkynyl group as described above and a bicyclo[6.1.0]non-4-yn-9-yl] group, more preferably $Q^1$ is selected from the formulae (9j), (9n), (9o), (9p), (9q), (9zo) and (9zk), as defined above. Most preferably, $Q^1$ is a bicyclo[6.1.0]non-4-yn-9-yl] group, preferably of formula (9q).

In a further preferred embodiment of the process for preparing the bioconjugate, the linker-conjugate is according to formula (4a) or (4b), or a salt thereof:

4a $$Q^1 \text{---} (Sp^3)_g \text{---} (Z^1)_d \text{---} (Sp^2)_c \text{---} [(O)_a \text{---} C(O) \text{---} N(H) \text{---} S(O)_2 \text{---} N(R^1) \text{---} (Sp^1)_b]_f \text{---} (Z^2)_e \text{---} (Sp^4)_i \text{---} D$$

4b $$D \text{---} (Sp^4)_i \text{---} (Z^2)_e \text{---} (Sp^1)_b \text{---} [(O)_a \text{---} C(O) \text{---} N(H) \text{---} S(O)_2 \text{---} N(R^1) \text{---} (Sp^2)_c]_f \text{---} (Z^1)_d \text{---} (Sp^3)_g \text{---} Q^1$$

wherein:
a is independently 0 or 1;
b is independently 0 or 1;
c is 0 or 1;
d is 0 or 1;
e is 0 or 1;
f is an integer in the range of 1 to 150;
g is 0 or 1;
i is 0 or 1;
D is a target molecule;
$Q^1$ is a reactive group capable of reacting with a functional group $F^1$ present on a biomolecule;
$Sp^1$ is a spacer moiety;
$Sp^2$ is a spacer moiety;
$Sp^3$ is a spacer moiety;
$Sp^4$ is a spacer moiety;
$Z^1$ is a connecting group that connects $Q^1$ or $Sp^3$ to $Sp^2$, O or C(O) or N(R');
$Z^2$ is a connecting group that connects D or $Sp^4$ to $Sp^1$, N($R^1$), O or C(O); and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups; or $R^1$ is D, -[$(Sp^1)_b(Z^2)_e(Sp^4)_i$ D] or -[$(Sp^2)_c(Z^1)_d(Sp^3)_g Q^1$], wherein D is a target molecule and $Sp^1$, $Sp^2$, $Sp^3$, $Sp^4$, $Z^1$, $Z^2$, $Q^1$, b, c, d, e, g and i are as defined above.

$Sp^1$, $Sp^2$, $Sp^3$ and $Sp^4$ are, independently, spacer moieties, in other words, $Sp^1$, $Sp^2$, $Sp^3$ and $Sp^4$ may differ from each other. $Sp^1$, $Sp^2$, $Sp^3$ and $Sp^4$ may be present or absent (b, c, g and i are, independently, 0 or 1). However, it is preferred that at least one of $Sp^1$, $Sp^2$, $Sp^3$ and $Sp^4$ is present, i.e. it is preferred that at least one of b, c, g and i is not 0.

If present, preferably $Sp^1$, $Sp^2$, $Sp^3$ and $Sp^4$ are independently selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups and $C_9$-$C_{200}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. When the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are interrupted by one or more heteroatoms as defined above, it is preferred that said groups are interrupted by one or more O-atoms, and/or by one or more S—S groups.

More preferably, spacer moieties $Sp^1$, $Sp^2$, $Sp^3$ and $Sp^4$, if present, are independently selected from the group consisting of linear or branched $C_1$-$C_{100}$ alkylene groups, $C_2$-$C_{100}$ alkenylene groups, $C_2$-$C_{100}$ alkynylene groups, $C_3$-$C_{100}$ cycloalkylene groups, $C_5$-$C_{100}$ cycloalkenylene groups, $C_5$-$C_{100}$ cycloalkynylene groups, $C_7$-$C_{100}$ alkylarylene groups, $C_7$-$C_{100}$ arylalkylene groups, $C_5$-$C_{100}$ arylalkenylene groups and $C_9$-$C_{100}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. Even more preferably, spacer moieties $Sp^1$, $Sp^2$, $Sp^3$ and $Sp^4$, if present, are independently selected from the group consisting of linear or branched $C_1$-$C_{50}$o alkylene groups, $C_2$-$C_{50}$ alkenylene groups, $C_2$-$C_{50}$ alkynylene groups, $C_3$-$C_{50}$ cycloalkylene groups, $C_5$-$C_{50}$ cycloalkenylene groups, $C_5$-$C_{50}$ cycloalkynylene groups, $C_7$-$C_{50}$ alkylarylene groups, $C_7$-$C_{50}$ arylalkylene groups, $C_5$-$C_{50}$ arylalkenylene groups and $C_9$-$C_{50}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. Yet even more preferably, spacer moieties $Sp^1$, $Sp^2$, $Sp^3$ and $Sp^4$, if present, are independently selected from the group consisting of linear or branched $C_1$-$C_{20}$ alkylene groups, $C_2$-$C_{20}$ alkenylene groups, $C_2$-$C_{20}$ alkynylene groups, $C_3$-$C_{20}$ cycloalkylene groups, $C_5$-$C_{20}$ cycloalkenylene groups, $C_8$-$C_{20}$ cycloalkynylene groups, $C_7$-$C_{20}$ alkylarylene groups, $C_7$-$C_{20}$ arylalkylene groups, $C_8$-$C_{20}$ arylalkenylene groups and $C_9$-$C_{20}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. In these preferred embodiments it is further preferred that the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are unsubstituted and optionally interrupted by one or more heteroatoms selected from the group of O, S and $NR^3$, preferably O, wherein $R^3$ is independently selected from the group consisting of hydrogen and $C_1$-$C_4$ alkyl groups, preferably hydrogen or methyl.

Most preferably, spacer moieties $Sp^1$, $Sp^2$, $Sp^3$ and $Sp^4$, if present, are independently selected from the group consisting of linear or branched $C_1$-$C_{20}$ alkylene groups, the alkylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. In this embodiment, it is further preferred that the alkylene groups are unsubstituted and optionally interrupted by one or more heteroatoms selected from the group of O, S and $NR^3$, preferably O and/or S—S, wherein $R^3$ is independently selected from the group consisting of hydrogen and $C_1$-$C_4$ alkyl groups, preferably hydrogen or methyl.

Particularly preferred spacer moieties $Sp^1$, $Sp^2$, $Sp^3$ and $Sp^4$ include —$(CH_2)_n$—, —$(CH_2CH_2)_n$—, —$(CH_2CH_2O)_n$—, —$(OCH_2CH_2)_n$—, —$(CH_2CH_2O)_nCH_2CH_2$—, —$CH_2CH_2(OCH_2CH_2)_n$—, —$(CH_2CH_2CH_2O)_n$—, —$(OCH_2CH_2CH_2)_n$—, —$(CH_2CH_2CH_2O)_nCH_2CH_2CH_2$— and —$CH_2CH_2CH_2(OCH_2CH_2CH_2)_n$—, wherein n is an integer in the range of 1 to 50, preferably in the range of 1 to 40, more preferably in the range of 1 to 30, even more preferably in the range of 1 to 20 and yet even more preferably in the range of 1 to 15. More preferably n is 1, 2, 3, 4, 5, 6, 7, 8, 9 or 10, more preferably 1, 2, 3, 4, 5, 6, 7 or 8, even more preferably 1, 2, 3, 4, 5 or 6, yet even more preferably 1, 2, 3 or 4.

In another preferred embodiment of the process according to the invention, in the linker-conjugates according to formula (4a) and (4b), spacer moieties $Sp^1$, $Sp^2$, $Sp^3$ and/or $Sp^4$, if present, comprise a sequence of amino acids. Spacer-moieties comprising a sequence of amino acids are known in the art, and may also be referred to as peptide linkers. Examples include spacer-moieties comprising a Val-Ala moiety or a Val-Cit moiety, e.g. Val-Cit-PABC, Val-Cit-PAB, Fmoc-Val-Cit-PAB, etc.

As described above, $Z^1$ and $Z^2$ are a connecting groups. In a preferred embodiment of the process according to the invention, $Z^1$ and $Z^2$ are independently selected from the group consisting of —O—, —S—, —$NR^2$—, —N=N—, —C(O)—, —$C(O)NR^2$—, —OC(O)—, —OC(O)O—, —$OC(O)NR^2$, —$NR_2C(O)$—, —$NR^2C(O)O$—, —$NR^2C(O)NR^2$—, —SC(O)—, —SC(O)O—, —$SC(O)NR^2$—, —S(O)—, —$S(O)_2$—, —$OS(O)_2$—, —$OS(O)_2O$—, —$OS(O)_2NR^2$—, —OS(O)—, —OS(O)O—, —$OS(O)NR^2$—, —$ONR^2C(O)$—, —$ONR^2C(O)O$—, —$ONR^2C(O)NR^2$—, —NR²OC(O)—, —NR²OC(O)O—, —NR²OC(O)NR²—, —ONR²C(S)—, —ONR²C(S)O—, —ONR²C(S)NR²—, —NR²OC(S)—, —NR²OC(S)O—, —NR²OC(S)NR²—, —OC(S)—, —OC(S)O—, —OC(S)NR²—, —NR²C(S)—, —NR²C(S)O—, —NR²C(S)NR²—, —SS(O)₂—, —SS(O)₂O—, —SS(O)₂NR²—, —NR₂OS(O)—, —NR₂OS(O)O—, —NR²OS(O)NR²—, —NR²OS(O)₂—, —NR²OS(O)₂O—, —NR²OS(O)₂NR²—, —ONR²S(O)—, —ONR²S(O)O—, —ONR²S(O)NR²—, —ONR²S(O)₂O—, —ONR²S(O)₂NR²—, —ONR²S(O)₂—, —OP(O)(R²)₂—, —SP(O)(R²)₂—, —NR²P(O)(R²)₂— and combinations of two or more thereof, wherein R² is independently selected from the group consisting of hydrogen, C₁-C₂₄ alkyl groups, C₂-C₂₄ alkenyl groups, C₂-C₂₄ alkynyl groups and C₃-C₂₄ cycloalkyl groups, the alkyl groups, alkenyl groups, alkynyl groups and cycloalkyl groups being optionally substituted.

In a particularly preferred process according to the invention, Sp¹, Sp², Sp³ and Sp⁴, if present, are independently selected from the group consisting of linear or branched C₁-C₂₀ alkylene groups, the alkylene groups being optionally substituted and optionally interrupted by one or more heteroatoms selected from the group consisting of O, S and NR³, wherein R³ is independently selected from the group consisting of hydrogen and C₁-C₄ alkyl groups, and wherein Q¹ is according to formula (9a), (9j), (9p), (9q), (9n), (9t), (9ze), (9zh), (9zo) or (9oo):

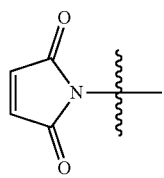
9a

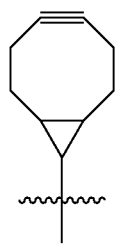
9q

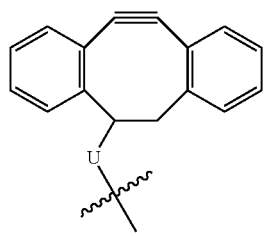
9n

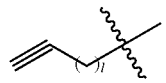
9j

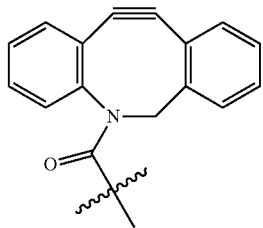
9o

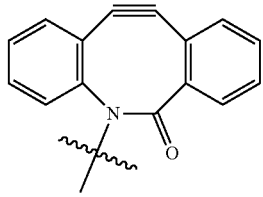
9p

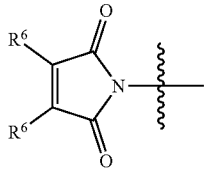
9ze

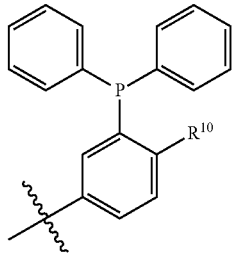
9t

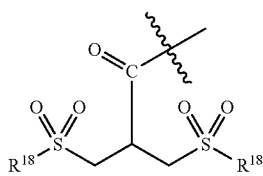
9zh

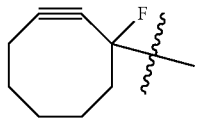
9zo wherein:
l is an integer in the range 0-10;
R¹⁰ is a (thio)ester group; and
R¹⁸ is selected from the group consisting of, optionally substituted, C₁-C₁₂ alkyl groups and C₄-C₁₂ (hetero)aryl groups.

Figure 4:
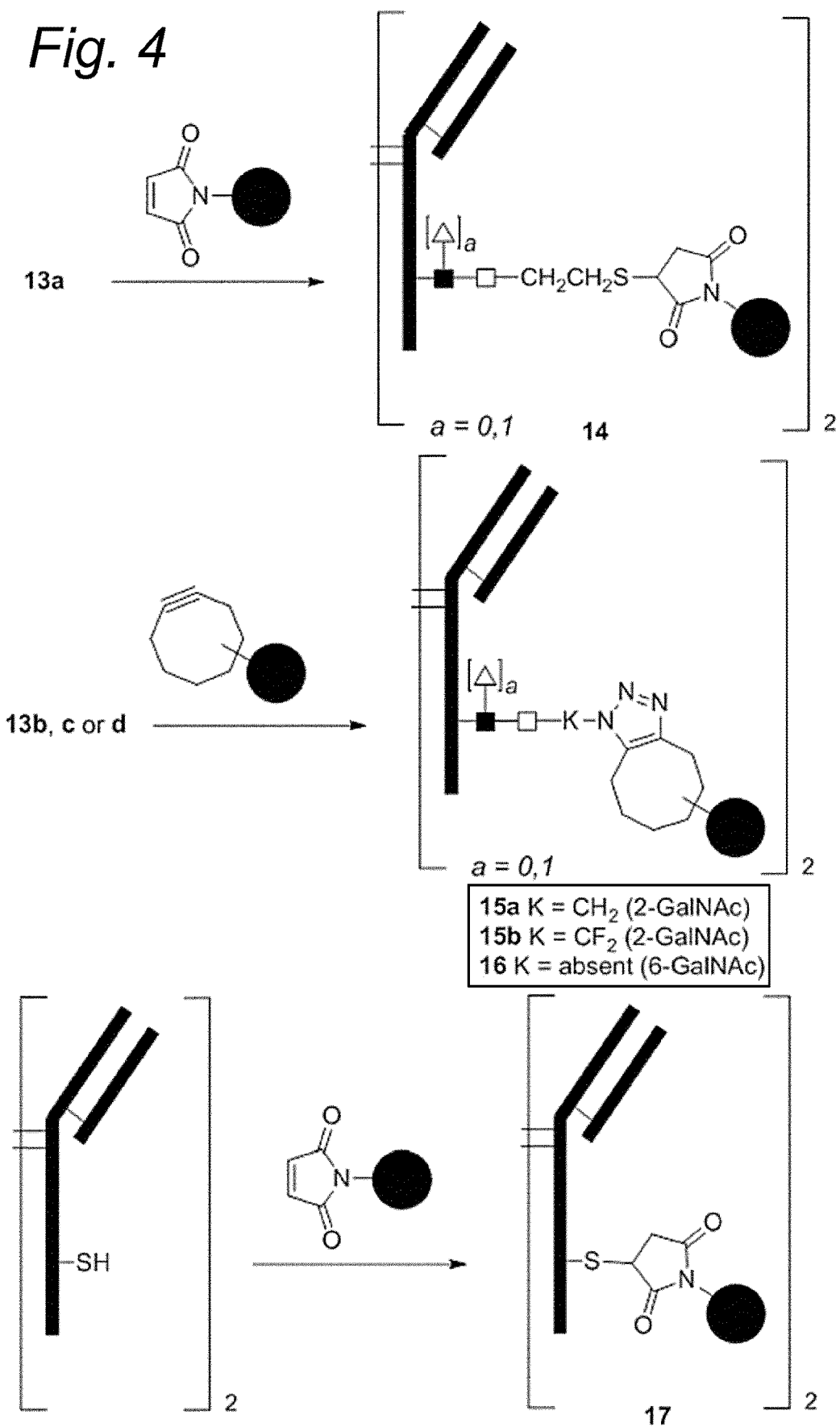
FIG. 4 shows how a modified antibody 13a-d may undergo a bioconjugation process by means of nucleophilic addition to maleimide (as for 3-mercaptopropionyl-galactosamine-modified 13a leading to thioether conjugate 14, or for conjugation to a engineered cysteine residue leading to thioether conjugate 17) or upon strain-promoted cycloaddition with a cyclooctyne reagent (as for 13b, 13c or 13d leading to triazoles 15a, 15b or 16, respectively).
Figure 7:
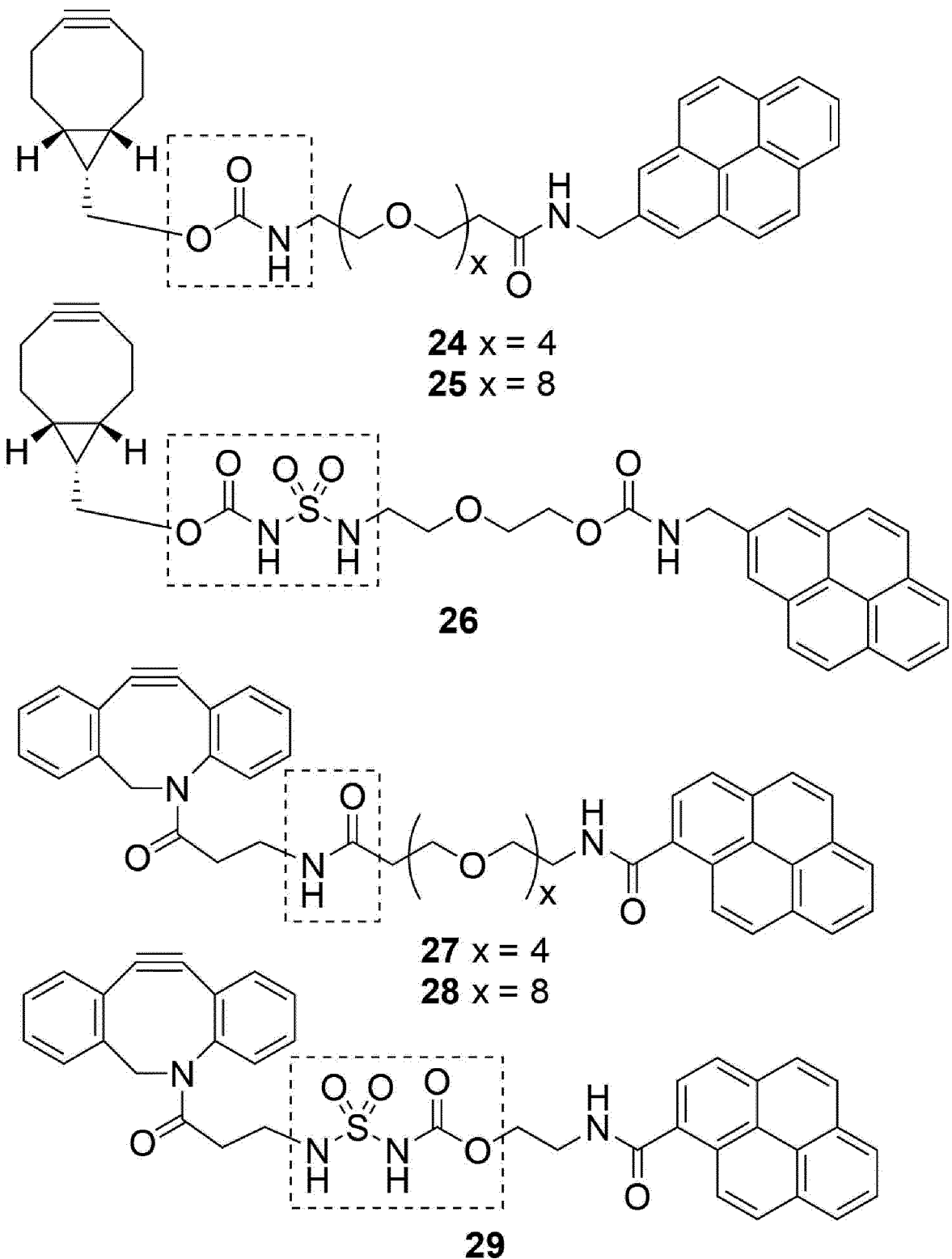
FIG. 7 shows the structures of several compounds wherein a bicyclo[6.1.0]non-4-yn-9-yl] reactive group $Q^1$ (also referred to as a BCN group) or a dibenzoazocyclooctyne reactive group $Q^1$ (also referred to as a DIBAC group or DBCO group) is connected to pyrene via a linker unit. Linkers 26 and 29 are according to the invention, linkers 24, 25, 27 and 28 are not according to the invention.
Figure 9:
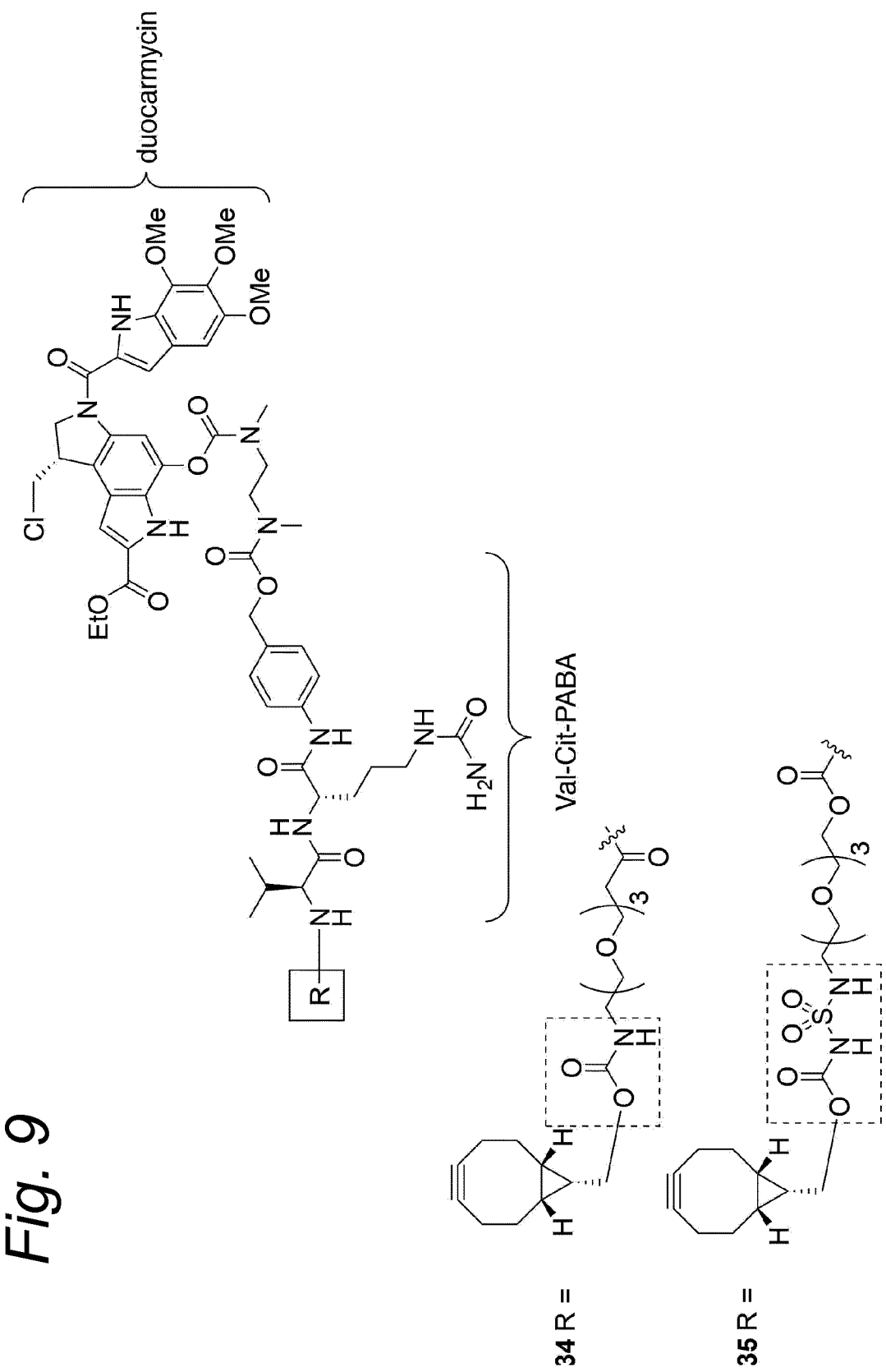
FIG. 9 shows the structures of two compounds wherein a bicyclo[6.1.0]non-4-yn-9-yl] reactive group $Q^1$ (also referred to as a BCN group) is connected to a Val-Cit-PABA-duocarmycin construct via a linker unit. Linker-conjugate 35 is according to the invention, while linker-conjugate 34 is not.
Figure 10:
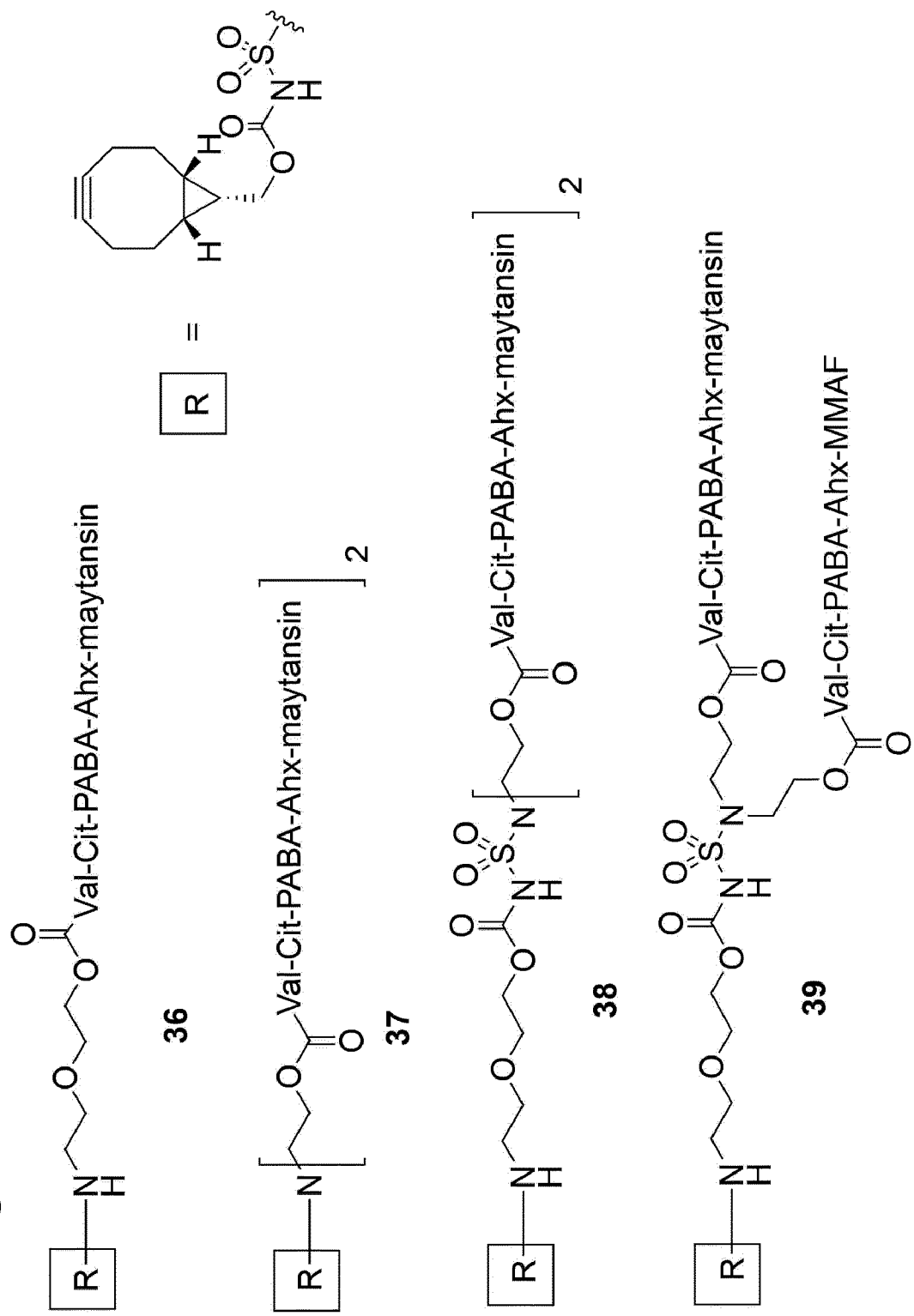
FIG. 10 shows the structures of compounds 36-39 that are suitable as linker-conjugates according to the present invention wherein a bicyclo[6.1.0]non-4-yn-9-yl] reactive group $Q^1$ (also referred to as a BCN group) is conjugated to Val-Cit-PABA-Ahx-maytansin via a sulfamide linker.
Figure 12:
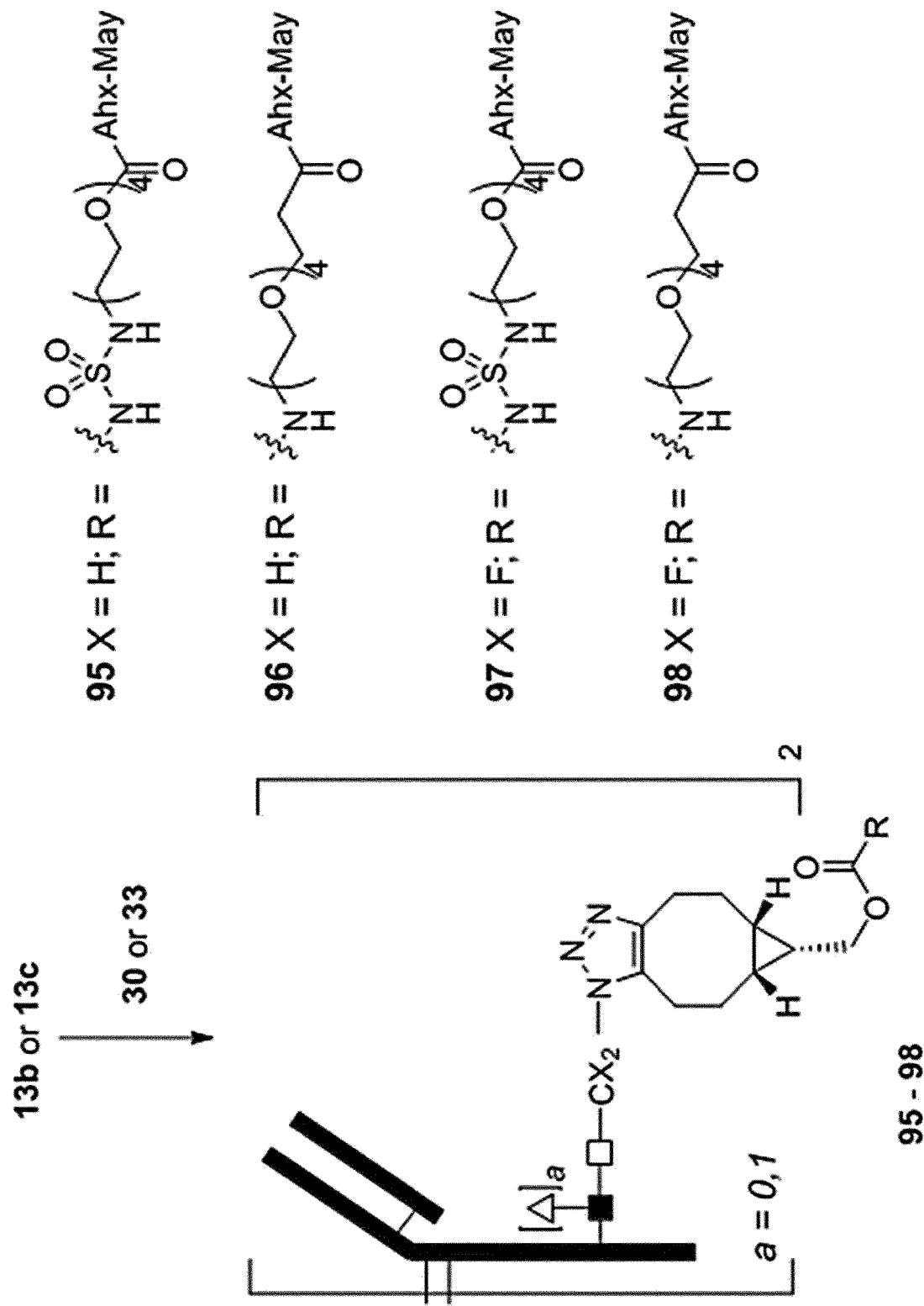
FIG. 12 shows the preparation of antibody-drug-conjugates 95-98, prepared in Examples 1-4 and used in Examples 29 and 31.

An embodiment of the process for preparing the bioconjugate is depicted in FIG. 4. FIG. 4 shows how a modified antibody 13a-d may undergo a bioconjugation process by means of nucleophilic addition with maleimide (as for 3-mercaptopropionyl-galactosamine-modified 13a leading to thioether conjugate 14, or for conjugation to an engineered cysteine residue leading to thioether conjugate 17) or upon strain-promoted cycloaddition with a cyclooctyne reagent (as for 13b, 13c or 13d, leading to triazoles 15a, 15b or 16, respectively).

In addition to the increased therapeutic index of the bioconjugates according to the invention, a further advantages of the process for the preparation of a bioconjugate as described herein, and of the linker-conjugates and sulfamide linker according to the invention is that conjugation efficiency increases in case a sulfamide linker is used instead of a typical polyethylene glycol (PEG) spacer. An additional advantage of a sulfamide group, in particular of an acylsulfamide or a carbamoylsulfamide group, is its high polarity, which imparts a positive effect on the solubility of a linker comprising such group, and on the construct as a whole, before, during and after conjugation. In view of this increased polarity, conjugation with linker-conjugate containing the sulfamide linker according to the invention are particularly suited to conjugate hydrophobic target compounds to a biomolecule. The high polarity of the sulfamides also has a positive impact in case hydrophobic moieties are conjugated to a biomolecule of interest, which is known to require large amounts of organic cosolvent during conjugation and/or induce aggregation of the bioconjugate. High levels of cosolvent (up to 25% of DMF or even 50% of DMA, propylene glycol, or DMSO) may induce protein denaturation during the conjugation process and/or may require special equipment in the manufacturing process. Thus, the problem of aggregation associated with the hydrophobic linking moieties in bioconjugates is efficiently solved by using the sulfamide linker according to the invention in the spacer between the target molecule and the reactive group $Q^1$ in the linker-conjugate in the formation of the bioconjugate. An additional advantage of a sulfamide linker according the invention, and its use in bioconjugation processes, is its ease of synthesis and high yields.

For evidence of these beneficial effects of the use of the sulfamide linker according to the present invention, reference is made to PCT/NL2015/050697 (WO 2016/053107), in particular to Tables 1-3, FIGS. 11-14, 23 and 24, and Examples 57, 58, 60 and 61 therein. These Tables, Figures and Examples of PCT/NL2015/050697(WO 2016/053107) are incorporated herein.

Method According to the First Aspect

The invention thus concerns in a first aspect a method for increasing the therapeutic index of a bioconjugate, comprising the step of preparing the bioconjugate of formula (A):

$$B\text{-}L\text{-}D \qquad (A),$$

wherein:
B is a biomolecule;
L is a linker linking B and D;
D is a target molecule; and
each occurrence of "—" is independently a bond or a spacer moiety, by reacting a reactive group $Q^1$ on a target molecule (D) with a functional group $F^1$ on a biomolecule (B), such that L comprises a group according to formula (1) or a salt thereof:

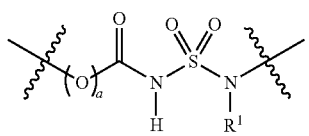

wherein:
a is 0 or 1; and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is an additional target molecule D, wherein D is optionally connected to N via a spacer moiety.

The bioconjugate of formula (A) is described a great detail above, which equally applies to the bioconjugate used in the first aspect of the invention.

Herein, the therapeutic index is increased compared to a bioconjugate of formula (A), wherein linker L does not comprise a group according to formula (1) or a salt thereof. The inventors surprisingly found that the therapeutic index of the bioconjugates according to the invention was significantly increased when linker L according to the present invention was used, even if all other factors, in particular the type of biomolecule and the type of target molecule and biomolecule-target molecule-ratio, were kept constant. The increased therapeutic index could solely be attributed to the presence of a group according to formula (1) in the linker.

The increased therapeutic index is preferably an increased therapeutic index in the treatment of cancer.

The method according to the first aspect of the invention may also be worded as a method for increasing the therapeutic index of a bioconjugate, comprising the step of providing a bioconjugate represented by formula (A):

$$B\text{-}L\text{-}D \qquad (A),$$

wherein:
B is a biomolecule;
L is a linker linking B and D;
D is a target molecule; and
each occurrence of "—" is independently a bond or a spacer moiety,
wherein L comprises a group according to formula (1) or a salt thereof:

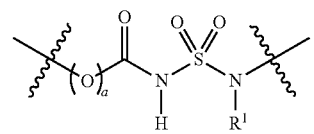

wherein:
a is 0 or 1; and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is an additional target molecule D, wherein the target molecule is optionally connected to N via a spacer moiety.

The inventors found that the linker according to the invention, as comprised in the bioconjugates according to the invention, has an effect on both aspects of the therapeutic index: (a) on the therapeutic efficacy and (b) on the tolerability. Thus, the method for increasing the therapeutic index is preferably for (a) increasing the therapeutic efficacy, and/or (b) increasing the tolerability of a bioconjugate of formula (A).

Thus, in one embodiment, the method according to the first aspect is for increasing the therapeutic efficacy of a bioconjugate of formula (A). Herein, "increasing the therapeutic efficacy" can also be worded as "lowering the effective dose" or "lowering the $ED_{50}$ value" or "increasing the protective index". Likewise, in one embodiment, the method according to the first aspect is for increasing the tolerability of a bioconjugate of formula (A). Herein, "increasing the tolerability" can also be worded as "increasing the maximum tolerated dose (MTD)", "increasing the $TD_{50}$ value" or "reducing the toxicity". In one especially preferred embodiment, the method according to the first aspect is for (a) increasing the therapeutic efficacy and (b) increasing the tolerability of a bioconjugate of formula (A).

The method according to the first aspect is largely non-medical. In one embodiment, the method is a non-medical or non-therapeutic method for increasing the therapeutic efficacy of a bioconjugate.

The first aspect of the invention can also be worded as linker L for use in improving the therapeutic efficacy of a bioconjugate of formula (A), wherein L and (A) are as defined above. In other words, the first aspect concerns the use of a linker L for the preparation of a bioconjugate of formula (A) for improving the therapeutic efficacy of the bioconjugate, wherein L and (A) are as defined above. The invention according to the first aspect can also be worded as the use of a linker L in a bioconjugate of formula (A), or in the preparation of a bioconjugate of formula (A), for increasing the therapeutic efficacy of the bioconjugate, wherein L and (A) are as defined above. The use as defined herein may be referred to as a non-medical or non-therapeutic use.

The bioconjugate used in the method according to the present aspect is preferably obtainable by the process for the preparation of a bioconjugate as defined above, more preferably the bioconjugate is obtained by the process for the preparation of a bioconjugate as defined above. It was found that bioconjugates thus obtained had an even further improved therapeutic index.

In one embodiment, the method, use or linker for use according to the first aspect of the invention further comprises the administration of the bioconjugate according to the invention to a subject in need thereof, most suitably a cancer patient. The use of bioconjugates such as antibody-drug-conjugates, is well-known in the field of cancer treatment, and the bioconjugates according to the invention are especially suited in this respect.

Typically, the bioconjugate is administered in a therapeutically effective dose. Administration may be in a single dose or may e.g. occur 1-4 times a month, preferably 1-2 times a month. In a preferred embodiment, administration occurs once every 3 or 4 weeks, most preferably every 4 weeks. In view of the increased therapeutic efficacy, administration may occur less frequent as would be the case during treatment with conventional bioconjugates. As will be appreciated by the person skilled in the art, the dose of the bioconjugate according to the invention may depend on many factors and the optimal dosing regime can be determined by the skilled person via routine experimentation. The bioconjugate is typically administered in a dose of 0.01-50 mg/kg body weight of the subject, more accurately 0.1-25 mg/kg or most accurately 0.5-10 mg/kg. In one embodiment, administration occurs via intravenous injection.

Method According to the Second Aspect

The invention concerns in a second aspect a method for the treatment of a subject in need thereof, comprising the administration of the bioconjugate of formula (A) as defined above. The subject in need thereof is most preferably a cancer patient. The use of bioconjugates such as antibody-drug-conjugates, is well-known in the field of cancer treatment, and the bioconjugates according to the invention are especially suited in this respect. The method as described is typically suited for the treatment of cancer. The bioconjugate of formula (A) is described a great detail above, which equally applies to the bioconjugate used in the second aspect of the invention.

The second aspect of the invention can also be worded as a bioconjugate of formula (A) for use in the treatment of a subject in need thereof, preferably for the treatment of cancer, wherein (A) is as defined above. In other words, the second aspect concerns the use of a bioconjugate of formula (A) for the preparation of a medicament for use in the treatment of a subject in need thereof, preferably for use in the treatment of cancer, wherein (A) is as defined above.

The method according to the second aspect may also be worded as a method for targeting tumour cells. In the context of the present aspect, the targeting of tumour cells includes one or more of treating, imaging, diagnosing, preventing the proliferation of, containing and reducing tumour cells. The method according to the second aspect may also be worded as a method for targeting tumours. In the context of the present aspect, the targeting of tumour cells includes one or more of treating, imaging, diagnosing, preventing the proliferation of, containing and reducing tumours. Most preferably, the present aspect is for the treatment of tumours.

The skilled person understands that the choice of target molecule D may be determined by the specific intended use of the bioconjugate according to the invention according to the present aspect. For example, in case the method according to the present aspect is for treating, it is preferred that target molecule D is a drug, more preferably a cytotoxin. Likewise, in case the method according to the present aspect is for imaging or diagnosing, it is preferred that target molecule D is a reporter molecule. In the context of the method according to the present aspect, it is preferred that biomolecule B is an antibody. Likewise, it is preferred that the bioconjugate is an antibody-drug-conjugate.

The bioconjugate used in the method according to the present aspect is preferably obtainable by the process for the preparation of a bioconjugate as defined above, more preferably bioconjugate is obtained by the process for the preparation of a bioconjugate as defined above.

In the method according to the second aspect, the bioconjugate is typically administered in a therapeutically effective dose. Administration may be in a single dose or may e.g. occur 1-4 times a month, preferably 1-2 times a month. In a preferred embodiment, administration occurs once every 3 or 4 weeks, most preferably every 4 weeks. As will be appreciated by the person skilled in the art, the dose of the bioconjugate according to the invention may depend on many factors and the optimal dosing regime can be determined by the skilled person via routine experimentation. The bioconjugate is typically administered in a dose of 0.01-50 mg/kg body weight of the subject, more accurately 0.1-25 mg/kg, most accurately or 0.5-10 mg/kg. In one embodiment, administration occurs via intravenous injection.

In view of the increased therapeutic efficacy, administration may occur less frequent as in treatment with conventional bioconjugates and/or at a lower dose. In one embodiment, the administration of the bioconjugate according to the invention is at a dose that is lower than the $TD_{50}$ of the same bioconjugate but not comprising the linker according to the invention, preferably the dose is at most 99-90%, more preferably at most 89-60%, even more preferable at most 59-30%, most preferably at most 29-10% of the $TD_{50}$ of the same bioconjugate but not comprising the linker according to the invention. In one embodiment, the administration of the bioconjugate according to the invention is at a dose that is lower than the $ED_{50}$ of the same bioconjugate but not comprising the linker according to the invention, preferably the dose is at most 99-90%, more preferably at most 89-60%, even more preferable at most 59-30%, most preferably at most 29-10% of the $ED_{50}$ of the same bioconjugate but not comprising the linker according to the invention. In one embodiment, the administration of the bioconjugate according to the invention occurs less frequent as administration would occur for the same bioconjugate but not comprising the linker according to the invention, preferably the number of administration events is at most 75%, more preferably at most 50% of the number of administration events of the same bioconjugate but not comprising the linker according to the invention. Alternatively, in view of the increased tolerability, administration may occur in a higher dose as in treatment with conventional bioconjugates. In one embodiment, the administration of the bioconjugate according to the invention is at a dose that is higher than the $TD_{50}$ of the same bioconjugate but not comprising the linker according to the invention, preferably the dose is at most 25-50%, more preferably at most 50-75%, most preferably at most 75-100% of the $TD_{50}$ of the same bioconjugate but not comprising the linker according to the invention. In one embodiment, the dose is at least a factor 1.1-1.49 higher, more preferably at least a factor 1.5-1.99 higher, even more preferable a factor 2-4.99 higher, most preferably at least a factor 5-10 higher of the $TD_{50}$ of the same bioconjugate but not comprising the linker according to the invention.

EXAMPLES

Reference to PCT/NL2015/050697 (WO 2016/053107) is made for the synthesis of the following compounds that are suitable as linker-conjugates to be used in the method according to the invention, or a model thereof:
Compound 18 (Example 20);
Compound 20 (Examples 21, 23-25);
Compound 21 (Examples 26-27);
Compound 23 (Examples 29-31);
Compound 26 (Examples 36-38);
Compound 30 (Examples 43-1, 32);
Compound 33 (Examples 36-37, 47);
Compound 35 (Examples 36-37, 49);
Compound 36 (Examples 29, 50);
Compound 37 (Examples 51-53);
Compound 38 (Examples 29, 54-55);
Compound 39 (Examples 29, 54, 56).

The preparation of the following modified biomolecules, suitable as biomolecule to be used in the method according to the invention, is described in PCT/NL2015/050697 (WO 2016/053107):
trastuzumab(GalNProSH)$_2$ 13a (Examples 1-6, 12-14);
trastuzumab(GalNAz)$_2$ 13b (Examples 12, 13, 15, 16-1);
trastuzumab(F$_2$-GalNAz)$_2$ 13c (Examples 1, 7-13, 16-2)

Bioconjugates according to the present invention can be prepared according to Example 59 of PCT/NL2015/050697 (WO 2016/053107). Conjugates of linker-conjugate 30 or 33 with modified biomolecule 13b or 13c have been prepared as such (conjugates 95-98, see Examples 1-4 and FIG. 12) and are used in the in vivo studies of Examples 29 and 31.

All of the aforementioned examples of PCT/NL2015/050697 (WO 2016/053107) are incorporated herein by reference.

RP-HPLC Analysis of Reduced Monoclonal Antibodies

Prior to RP-HPLC analysis samples were reduced by incubating a solution of 10 µg (modified) IgG for 15 minutes at 37° C. with 10 mM DTT and 100 mM Tris pH 8.0 in a total volume of 50 µL. A solution of 49% ACN, 49% MQ and 2% formic acid (50 µL) was added to the reduced sample. Reverse phase HPLC was performed on a Agilent 1100 HPLC using a ZORBAX Phoroshell 300SB-C8 1×75 5 µm (Agilent Technologies) column run at 1 ml/min at 70° C. using a 16.9 minute linear gradient from 25 to 50% buffer B (with buffer A=90% MQ, 10% ACN, 0.1% TFA and buffer B=90% ACN, 10% MQ, 0.1% TFA).

Mass Spectral Analysis of Monoclonal Antibodies

Prior to mass spectral analysis, IgGs were either treated with DTT, which allows analysis of both light and heavy chain, or treated with Fabricator™ (commercially available from Genovis, Lund, Sweden), which allows analysis of the Fc/2 fragment. For analysis of both light and heavy chain, a solution of 20 µg (modified) IgG was incubated for 5 minutes at 37° C. with 100 mM DTT in a total volume of 4 µL. If present, azide-functionalities are reduced to amines under these conditions. For analysis of the Fc/2 fragment, a solution of 20 µg (modified) IgG was incubated for 1 hour at 37° C. with Fabricator™ (1.25 U/µL) in phosphate-buffered saline (PBS) pH 6.6 in a total volume of 10 µL. After reduction or Fabricator-digestion the samples were washed trice with milliQ using an Amicon Ultra-0.5, Ultracel-10 Membrane (Millipore) resulting in a final sample volume of approximately 40 µL. Next, the samples were analysed by electrospray ionization time-of-flight (ESI-TOF) on a JEOL AccuTOF. Deconvoluted spectra were obtained using Magtran software.

Example 1: Conjugation of 13b with 30 to Obtain Conjugate 96

The bioconjugate according to the invention was prepared by conjugation of compound 30 as linker-conjugate to modified biomolecule 13b as biomolecule. To a solution of trastuzumab(azide)$_2$ (13b) (15.5 mL, 255 mg, 16.47 mg/ml in PBS pH 7.4) was added DMA (1.45 mL) and compound 30 (255 µL, 40 mM solution DMA). The reaction was incubated overnight at rt followed by purification on a HiLoad 26/600 Superdex200 PG column (GE Healthcare) on an AKTA Purifier-10 (GE Healthcare). Mass spectral analysis of the reduced sample showed one major heavy chain product (observed mass 50938 Da, approximately 80% of total heavy chain fragment), corresponding to the conjugated heavy chain.

Example 2: Conjugation of 13b with 33 to Obtain Conjugate 95

The bioconjugate according to the invention was prepared by conjugation of compound 33 as linker-conjugate to modified biomolecule 13b as biomolecule. To a solution of trastuzumab(azide)$_2$ (13b) (607 µL, 10 mg, 16.47 mg/ml in PBS pH 7.4) was added MilliQ (50 µL) and compound 33

(10 µL, 40 mM solution in DMA). The reaction was incubated overnight at rt followed by purification on a Superdex200 10/300 GL (GE Healthcare) on an AKTA Purifier-10 (GE Healthcare). Mass spectral analysis of the reduced sample showed one major heavy chain product (observed mass 50982 Da, approximately 80% of total heavy chain fragment), corresponding to the conjugated heavy chain.

Example 3: Conjugation of 13c with 30 to Obtain Conjugate 98

The bioconjugate according to the invention was prepared by conjugation of compound 30 as linker-conjugate to modified biomolecule 13c as biomolecule. To a solution of trastuzumab(azide)₂ (13c) (14.25 mL, 250 mg, 17.55 mg/ml in PBS pH 7.4) was added DMA (1.4 mL) and compound 30 (250 µL, 40 mM solution DMA). The reaction was incubated overnight at rt followed by purification on a HiLoad 26/600 Superdex200 PG column (GE Healthcare) on an AKTA Purifier-10 (GE Healthcare). Mass spectral analysis of the reduced sample showed one major heavy chain product (observed mass 50969 Da, approximately 70% of total heavy chain fragment), corresponding to the conjugated heavy chain.

Example 4: Conjugation of 13c with 33 to Obtain Conjugate 97

The bioconjugate according to the invention was prepared by conjugation of compound 33 as linker-conjugate to modified biomolecule 13c as biomolecule. To a solution of trastuzumab(azide)₂ (13c) (14.25 mL, 250 mg, 17.55 mg/ml in PBS pH 7.4) was added compound 33 (188 µL, 40 mM solution DMA). The reaction was incubated overnight at rt followed by purification on a HiLoad 26/600 Superdex200 PG column (GE Healthcare) on an AKTA Purifier-10 (GE Healthcare). Mass spectral analysis of the reduced sample showed one major heavy chain product (observed mass 51020 Da, approximately 90% of total heavy chain fragment), corresponding to the conjugated heavy chain.

Examples 5-16: Preparation of Linker Conjugates 100, 108 and 111

The synthesis of linker-conjugates 100 and 108 according to the invention are described herein, as well as of control linker-conjugate 111. The synthetic schemes towards compounds 100, 108 and 111 are depicted here below.

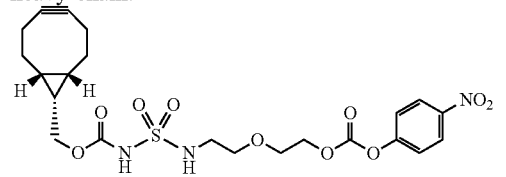
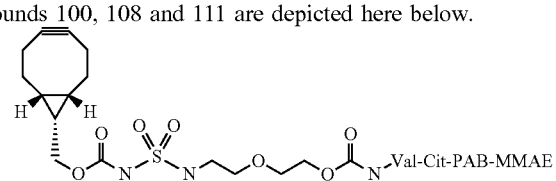
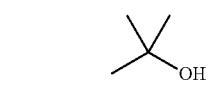
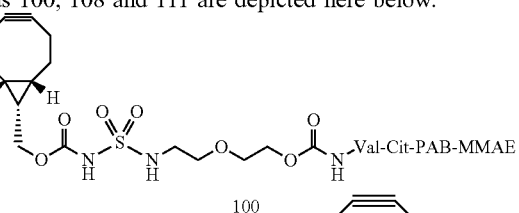
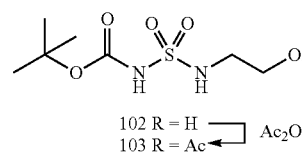
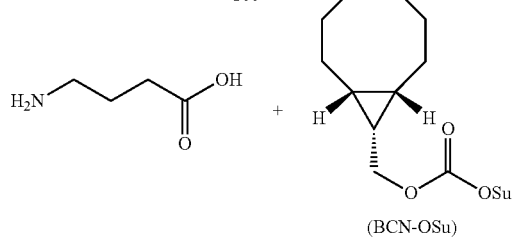
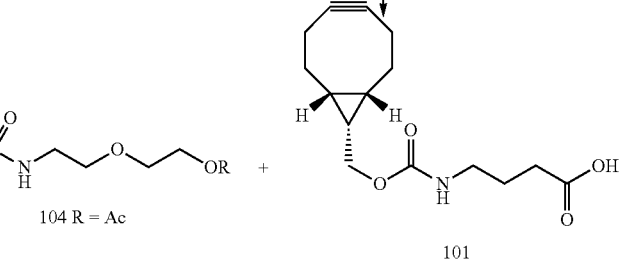
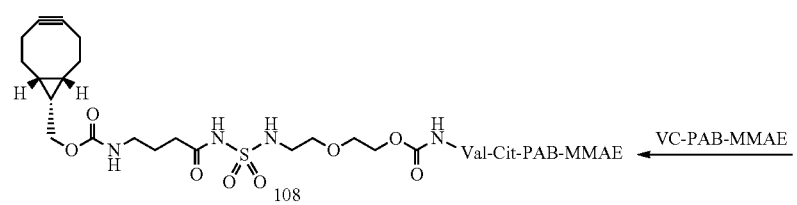
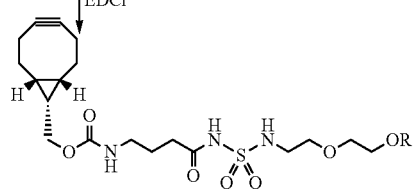

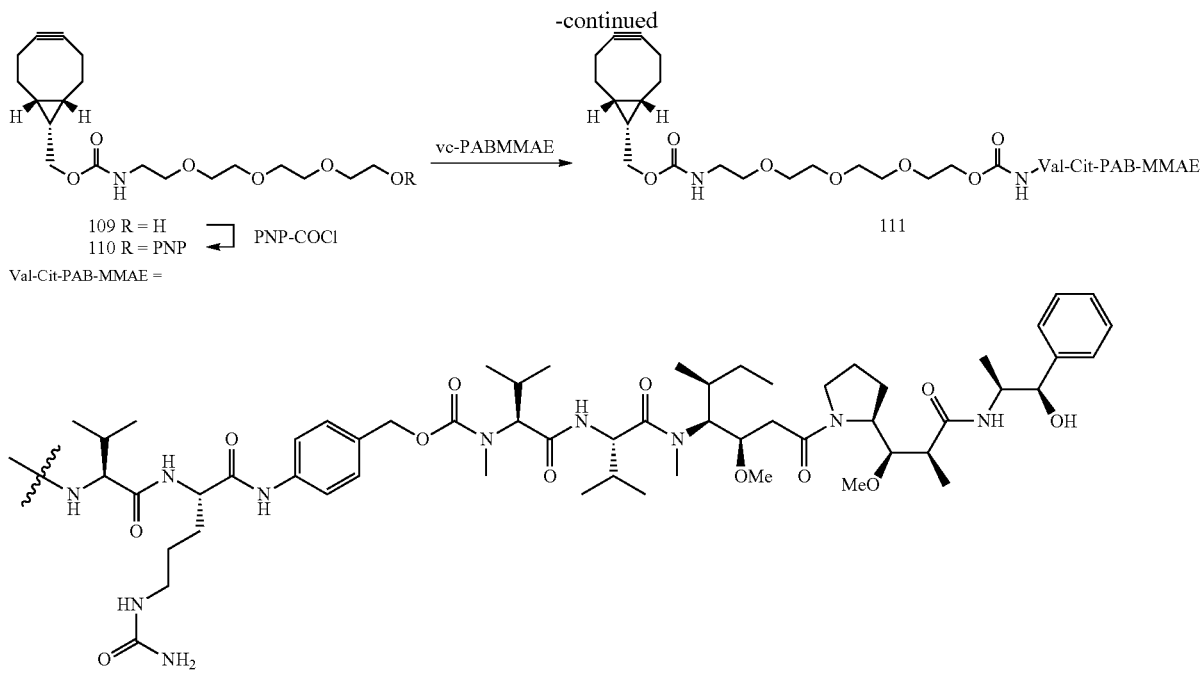

Example 5: Preparation of Compound 100

A solution of compound 99 (prepared via activation of compound 58 as disclosed in and prepared according to Example 50 of PCT/NL2015/050697 (WO 2016/053107); 4.7 mg, 9.0 μmol) in DMF (200 μL) was added to solid Val-Cit-PAB-MMAE (vc-PABMMAE, 10 mg, 8.1 μmol) followed by addition of Et$_3$N (3.7 μL, 2.7 mg, 27 μmol). After 23 h, 2'-(ethylenedioxy)bis(ethylamine) (1.3 μL, 1.3 mg, 8.9 μmol) in DMF was added (13 μL of 10% solution in DMF). The mixture was left for 4h and purified via reversed phase (C18) HPLC chromatography (30-90% MeCN (1% AcOH) in H$_2$O (1% AcOH). The product was obtained as a colourless film (10.7 mg, 7.1 μmol, 87%) LCMS (ESI$^+$) calculated for C$_{74}$H$_{117}$N$_{12}$O$_{19}$S$^+$ (M+H$^+$) 1509.83 found 1510.59

Example 6: Preparation of Compound 101

To a solution of BCN-OSu (1.00 g, 3.43 mmol) in a mixture of THF and water (80 mL/80 mL) were added γ-aminobutyric acid (0.60 g, 5.12 mmol) and Et$_3$N (1.43 mL, 1.04 g, 10.2 mmol). The mixture was stirred for 4 h followed by addition of DCM (200 mL) and a saturated aqueous solution of NH$_4$Cl (80 mL). After separation, the aqueous layer was extracted with DCM (2×200 mL). The combined organic layers were dried (Na$_2$SO$_4$) and concentrated. The residue was purified with column chromatography (MeOH in DCM 0-10%). The product was obtained as a colourless thick oil (730 mg, 2.61 mmol, 76%). $^1$H NMR (400 MHz, CDCl$_3$) δ (ppm) 4.81 (bs, 1H), 4.15 (d, J=8.4 Hz, 2H), 3.30-3.21 (m, 2H), 2.42 (t, J=7.2 Hz, 2H), 2.35-2.16 (m, 6H), 1.85 (quintet, J=6.9 Hz, 2H), 1.64-1.51 (m, 2H), 1.35 (quintet, J=8.4 Hz, 1H), 1.00-0.90 (m, 2H)

Example 7: Preparation of Compound 102

Chlorosulfonyl isocyanate (CSI; 0.91 mL, 1.48 g, 10 mmol) was added to a cooled (−78° C.) solution of tert-butanol (5.0 mL, 3.88 g, 52 mmol) in Et$_2$O (50 mL). The reaction mixture was allowed to warm to rt and was concentrated. The residue was suspended in DCM (200 mL) and subsequently Et$_3$N (4.2 mL, 3.0 g, 30 mmol) and 2-(2-aminoethoxy)ethanol (1.0 mL, 1.05 g; 10 mmol) were added. The resulting mixture was stirred for 10 min and concentrated. The residue was purified twice with column chromatography (MeOH in DCM 0→10%). The product was obtained as a colourless thick oil (2.9 g, 10 mmol, 100%)$^1$H NMR (400 MHz, CDCl$_3$) δ (ppm) 5.75 (bs, 1H), 3.79-3.74 (m, 2H), 3.67-3.62 (m, 2H), 3.61-3.57 (m, 2H), 3.35-3.28 (m, 2H), 1.50 (s, 9H).

Example 8: Preparation of Compound 103

To a solution of 102 (2.9 g, 10 mmol) in DCM (40 mL) were added Ac$_2$O (2.9 mL, 3.11 g, 30.5 mmol) and Et$_3$N (12.8 mL, 9.29 g, 91.8 mmol). The reaction mixture was stirred for 2 h, washed with a saturated aqueous solution of NaHCO$_3$ (50 mL) and dried (Na$_2$SO$_4$). The residue was purified twice with column chromatography (20%-100% EtOAc in heptane). The product was obtained as a colourless oil (2.5 g, 7.7 mmol, 77%)$^1$H NMR (400 MHz, CDCl$_3$) δ (ppm) 5.48 (bs, 1H), 4.25-4.20 (m, 2H), 3.70-3.60 (m, 4H), 3.33-3.23 (m, 2H), 2.10 (s, 3H), 1.50 (s, 9H)

Example 9: Preparation of Compound 104

To a solution of 103 (80 mg, 0.25 mmol) in DCM (8 mL) was added TFA (2 mL). After 40 min, the reaction mixture was concentrated. The residue was taken up in toluene (30 mL) and the mixture was concentrated. The product was obtained as colourless oil (54 mg, 0.24 mmol, 95%). $^1$H NMR (400 MHz, CDCl$_3$) δ (ppm) 5.15 (bs, 2H), 4.26-4.18 (m, 2H), 3.71-3.60 (m, 4H), 3.35-3.27 (m, 2H), 2.08 (s, 3H).

Example 10: Preparation of Compound 105

To a mixture of BCNGABA (101) (67 mg, 0.24 mmol) and 104 (54 mg, 0.24 mmol) in DCM (20 mL) were added N-(3-dimethylaminopropyl)-N$^1$-ethylcarbodiimide hydrochloride (EDCl.HCl; 55 mg, 0.29 mmol) and DMAP (2.8 mg, 23 µmol). The mixture was stirred for 16 and washed with a saturated aqueous solution of NH$_4$Cl (20 mL). After separation, the aqueous layer was extracted with DCM (20 mL). The combined organic layers were dried (Na$_2$SO$_4$) and concentrated. The residue was purified with column chromatography (MeOH in DCM 0-10%). The product was obtained as a colourless thick oil (50 mg, 0.10 mmol, 42%). $^1$H NMR (400 MHz, CDCl$_3$) δ (ppm) 5.83-5.72 (m, 1H), 5.14-5.04 (m, 1H), 4.23-4.19 (m, 2H), 4.15 (d, J=8.1 Hz, 2H), 3.67-3.57 (m, 4H), 3.29-3.18 (m, 4H), 2.41-2.32 (m, 2H), 2.31-2.15 (m, 6H), 2.10 (s, 3H), 1.85 (quintet, J=6.6 Hz, 2H), 1.65-1.49 (m, 2H), 1.38-1.28 (m, 1H), 1.00-0.89 (m, 2H)

Example 11: Preparation of Compound 106

To a solution of 105 (50 mg, 0.10 mmol) in MeOH (10 mL) was added K$_2$CO$_3$ (43 mg, 0.31 mmol). The mixture was stirred for 3h and diluted with a saturated aqueous solution of NH$_4$Cl (20 mL). The mixture was extracted with DCM (3×20 mL). The combined organic layers were dried (Na$_2$SO$_4$) and concentrated. The product was obtained as a colourless film (39 mg, 0.088 mmol, 88%). $^1$H NMR (400 MHz, CDCl$_3$) δ (ppm) 6.25 (bs, 1H), 5.26-5.18 (m, 1H), 4.15 (d, J=8.0 Hz, 2H), 3.77-3.71 (m, 2H), 3.63-3.53 (m, 4H), 3.33-3.27 (m, 2H), 3.27-3.17 (m, 2H), 2.45-2.34 (m, 2H), 2.34-2.14 (m, 6H), 1.85 (quintet, J=6.7 hz, 2H), 1.65-1.48 (m, 2H), 1.41-1.28 (m, 1H), 1.01-0.88 (m, 2H).

Example 12: Preparation of Compound 107

To a solution of 106 (152 mg, 0.34 mmol) in DCM (20 mL) were added p-nitrophenyl chloroformate (PNP—COCl; 69 mg, 0.34 mmol) and pyridine (28 µL, 27 mg, 0.34 mmol). The mixture was stirred for 1.5 h and concentrated. The residue was purified with column chromatography (50%→100% EtOAc in heptane). The product was obtained as a colourless thick oil (98 mg, 0.16 mmol, 47%). $^1$H NMR (400 MHz, CDCl$_3$) δ (ppm) 8.31-8.26 (m, 2H), 7.46-7.40 (m, 2H), 5.69-5.59 (m, 1H), 4.98-4.91 (m, 1H), 4.46-4.42 (m, 2H), 4.18 (d, J=8.1 Hz, 2H), 3.79-3.75 (m, 2H), 3.69-3.64 (m, 2H), 3.33-3.24 (m, 4H), 2.39-2.31 (m, 2H), 2.32-2.18 (m, 6H), 1.84 (quintet, J=6.3 Hz 2H), 1.65-1.50 (m, 2H), 1.35 (quintet, J=8.5 Hz, 1H), 1.01-0.91 (m, 2H).

Example 13: Preparation of Compound 108

To a solution of Val-Cit-PAB-MMAE (16.4 mg, 13.2 µmol) in DMF (400 µL) was added Et$_3$N (3.4 µL, 2.5 mg, 24 µmol). The resulting solution was added to a solution of 107 (6.7 mg, 11 µmol) in DMF (300 µL). DMF (50 µL) was added. After 21.5 h, 2'-(ethylenedioxy)bis(ethylamine) (1.2 µL, 1.2 mg, 8.2 µmol) in DMF was added (12 µL of 10% solution in DMF). The mixture was purified via reversed phase (C18) HPLC chromatography (30-90% MeCN (1% AcOH) in H$_2$O (1% AcOH). The product was obtained as a colourless film (4.3 mg, 2.7 µmol, 25%) LCMS (ESI$^+$) calculated for C$_{78}$H$_{124}$N$_{13}$O$_{20}$S$^+$ (M+H$^+$) 1594.88 found 1594.97

Example 14: Preparation of Compound 109

To a solution of 2-(2-(2-(2-aminoethoxy)ethoxy)ethoxy) ethanol (256 mg, 1.32 mmol) in DCM (30 mL) were added BCN-OSu (351 mg, 1.20 mmol) and Et$_3$N (502 µL, 364 mg, 3.60 mmol). The resulting solution was stirred for 30 min and washed with a saturated aqueous solution of NH$_4$Cl. After separation, the aqueous phase was extracted with DCM (30 mL). The combined organic phases were dried (Na$_2$SO$_4$) and concentrated. The residue was purified with column chromatography (MeOH in DCM 0-10%). The product was obtained as a colourless oil (397 mg, 1.07 mmol, 90%). $^1$H NMR (400 MHz, CDCl$_3$) δ (ppm) 5.93 (bs, 1H), 4.14 (d, J=8.1 Hz, 2H), 3.77-3.69 (m, 4H), 3.68-3.59 (m, 8H), 3.58-3.52 (m, 2H), 3.42-3.32 (m, 2H), 2.34-2.16 (m, 6H), 1.66-1.51 (m, 2H), 1.36 (quintet, J=8.7 Hz, 1H), 1.00-0.85 (m, 2H).

Example 15: Preparation of Compound 110

To a solution of 109 (0.40 g, 1.08 mmol) in DCM (50 mL) was added p-nitrophenyl chloroformate (PNP—COCl; 240 mg, 1.19 mmol) and Et$_3$N (452 µL, 328 mg, 3.24 mmol). The mixture was stirred for 20 h and concentrated. The residue was purified with column chromatography (20%-70% EtOAc in heptane). The product was obtained as a colourless oil (424 mg, 0.79 mmol, 73%). $^1$H NMR (400 MHz, CDCl$_3$) δ (ppm) 8.31-8.26 (m, 2H), 7.42-7.37 (m, 2H), 5.20 (bs, 1H), 4.47-4.43 (m, 2H), 4.15 (d, J=8.4 Hz, 2H), 3.84-3.80 (m, 2H), 3.75-3.60 (m, 8H), 3.59-3.54 (m, 2H), 3.42-3.32 (m, 2H), 2.35-2.16 (m, 6H), 1.66-1.50 (m, 2H), 1.40-1.30 (m, 1H), 1.00-0.85 (m, 2H).

Example 16: Preparation of Compound 111

To a solution of Val-Cit-PAB-MMAE (vc-PABMMAE; 13.9 mg; 0.011 mmol in DMF (400 µL) were added Et$_3$N (3.4 µL, 2.5 mg, 24.3 µmol) and a solution of 110 (3.0 mg, 5.6 µmol) in DMF (200 µL). After 25 min, Et$_3$N (1.1 µL, 0.80 mg, 7.9 µmol) and an additional solution of 110 (2.2 mg, 4.1 µmol) in DMF (33 µL). After 17.5 h, 2'-(ethylenedioxy)bis(ethylamine) (1.2 µL, 1.2 mg, 8.1 µmol) in DMF was added (12 µL of 10% solution in DMF). The mixture was left over night in the freezer and purified via reversed phase (C18) HPLC chromatography (30*90% MeCN (1% AcOH) in H$_2$O (1% AcOH). The product was obtained as a colorless film (10.9 mg, 7.2 µmol. 74%) LCMS (ESI$^+$) calculated for C$_{78}$H$_{124}$N$_{11}$O$_{19}$$^+$ (M+H$^+$) 1518.91 found 1519.09.

Examples 17-21: EndoSH

In one aspect, the invention concerns a fusion enzyme comprising two endoglycosidases. In a particular example the two endoglycosidases EndoS and EndoH are connected via a linker, preferably a -(Gly$_4$Ser)$_3$-(His)$_6$-(Gly$_4$Ser)$_3$- linker. The fusion enzyme according to the invention as also referred to as EndoSH. The enzyme according to the invention has at least 50% sequence identity with SEQ. ID NO: 1, preferably at least 70%, more preferably at least 80% sequence identity with SEQ. ID NO: 1, such as at least 81%, 82%, 83%, 84%, 85%, 86%, 87%, 88%, 89%, 90%, 91%, 92%, 93%, 94%, 95%, 96%, 97%, 98% or 99% sequence identity with SEQ. ID NO: 1. Identity can be readily calculated by known methods and/or computer program methods known in the art such as BLASTP publicly available from NCBI and other sources (BLAST Manual, Altschul, S., et al., NCBI NLM NIH Bethesda, MD 20894; Altschul, S., et al., J. Mol. Biol. 215:403-410 (1990). Preferably, the enzyme of the invention, having the above indicated sequence identity to SEQ. ID NO: 1, has EndoS and EndoH activity. Most preferably, the enzyme according to the invention has 100% sequence identity with SEQ. ID NO: 1.

Also encompassed are fusion enzymes of EndoS and EndoH, wherein the linker is replaced by another suitable linker known in the art, wherein said linker may be a rigid, or flexible. Preferably, said linker is a flexible linker allowing the adjacent protein domains to move relative freely to one another. Preferably, said flexible linker is composed of amino residues like glycine, serine, histidine and/or alanine and has a length of 3 to 59 amino acid residues, preferably 10 to 45 or 15 to 40 amino acid residues, such as 15, 16, 17, 18, 19, 20, 21, 22, 23, 24, 25, 26, 27, 28, 29, 30, 31, 32, 33, 34, 35, 36, 37, 38, 39 or 40 amino acid residues, or 20 to 38, 25 to 37 or 30 to 36 amino acid residues. Optionally, the fusion enzyme is covalently linked to, or comprises, a tag for ease of purification and or detection as known in the art, such as an Fc-tag, FLAG-tag, poly(His)-tag, HA-tag and Myc-tag.

Trimming of glycoproteins is known in the art, from e.g. WO 2007/133855 or WO 2014/065661. The enzyme according to the invention exhibits both EndoS and EndoH activity, and is capable of trimming glycans on glycoproteins (such as antibodies) at the core GlcNAc unit, leaving only the core GlcNAc residue on the glycoprotein (EndoS activity) as well as well as splitting off high-manose glycans (EndoH activity). Surprisingly, both activities of the fusion enzyme function smoothly at a pH around 7-8, while monomeric EndoH requires a pH of 6 to operate optimally.

The fusion enzyme according to the invention can be prepared by routine techniques in the art, such as introducing an expression vector (e.g. plasmid) comprising the enzyme coding sequence into a host cell (e.g. E. coli) for expression, from which the enzyme can be isolated. A possible approach for the preparation and purification of the fusion enzyme according to the invention is given in examples 17-19, and its functioning is demonstrated in examples 20 and 21, wherein trastuzumab and high-mannose trastuzumab are efficiently trimmed in a single step. Another example of the efficient trimming of glycans by the fusion protein EndoSH is provided in example 24.

Example 17: Cloning of Fusion Protein EndoSH into (pET22B) Expression Vector

A pET22B-vector containing an EndoS-$(G_4S)_3$-$(His)_6$-$(G_4S)_3$-EndoH (EndoSH) coding sequence (EndoSH being identified by SEQ. ID NO: 1) between EcoRI-HindIII sites was obtained from Genscript. The DNA sequence for the EndoSH fusion protein consists of the encoding residues 48-995 of EndoS fused via an N-terminal linked glycine-serine (GS) linker to EndoH. The glycine-serine (GS) linker comprises a -$(G_4S)_3$-$(His)_6$-$(G_4S)_3$— format, allowing spacing of the two enzymes and at the same time introducing a IMAC-purification tag.

Example 18: E. coli Expression of Fusion Protein EndoSH

Expression of the EndoSH fusion protein (identified by SEQ. ID NO: 1) starts with the transformation of the plasmid (pET22b-EndoSH) into BL21 cells. Next step is the inoculation of 500 mL culture (LB medium+Ampilicin) with BL21 cells. When the OD600 reached 0.7 the cultures were induced with 1 mM IPTG (500 µL of 1M stock solution).

Example 19: Purification of Fusion Protein EndoSH from E. coli

After overnight induction at 37° C. the cultures were pelleted by centrifugation. The pellets were resuspended in 40 mL PBS and incubated on ice with 5 ml lysozyme (10 mg/mL) for 30 minutes. After half an hour 5 ml 10% Triton-X-100 was added and sonicated (10 minutes) on ice. After the sonification the cell debris was removed by centrifugation (10 minutes 8000×g) followed by filtration through a 0.22 µM-pore diameter filter. The soluble extract was loaded onto a HisTrap HP 5 mL column (GE Healthcare). The column was first washed with buffer A (20 mM Tris buffer, 20 mM imidazole, 500 mM NaCl, pH 7.5). Retained protein was eluted with buffer B (20 mM Tris, 500 mM NaCl, 250 mM imidazole, pH 7.5, 10 mL). Fractions were analyzed by SDS-PAGE on polyacrylamide gels (12%). The fractions that contained purified target protein were combined and the buffer was exchanged against 20 mM Tris pH 7.5 and 150 mM NaCl by dialysis performed overnight at 4° C. The purified protein was concentrated to at least 2 mg/mL using an Amicon Ultra-0.5, Ultracel-10 Membrane (Millipore). The product is stored at −80° C. prior to further use.

Example 20: Trimming of Trastuzumab by EndoSH

Trastuzumab (obtained from Epirus biopharma (Utrecht, The Netherlands); 14 mg/mL) in 25 mM Tris buffer pH 8, was trimmed using a concentration of either 0.1 or 1 w/w % EndoSH. The reactions, 350 µg trastuzumab (25 µL) and the appropriate amount of EndoSH, were stirred at 37° C. and analyzed by MS analysis over time, 1 to 3 hours. Samples were subjected to Fabricator treatment prior to analysis. Full conversions to the trimmed product, which is trimmed to the core GlcNAc sugar residue, was observed after 1 hour at 37° C. with 0.1 w/w % EndoSH.

Example 21: Trimming of High-Mannose Trastuzumab by Fusion Protein EndoSH

Trastuzumab having high-mannose glycans (obtained via transient expression in CHO K1 cells in the presence of kifunensine performed by Evitria (Zurich, Switzerland)) (14 mg/mL) in 25 mM Tris buffer pH 8, was trimmed using a concentration of either 0.1 or 1 w/w % EndoSH. The reactions, 350 µg high-mannose trastuzumab (25 µL) and the appropriate amount of EndoSH, were stirred at 37° C. and analyzed by MS analysis over time, 1-3 hours. Samples were subjected to Fabricator treatment prior to analysis. Full conversions to the trimmed product, which is trimmed to the core GlcNAc sugar residue, was observed after 3 hours at 37° C. with 1 w/w % EndoSH.

Examples 22-28: Preparation of cAC10 Bioconjucates

The preparation of modified biomolecule 13d, is performed according to the procedure as is described below utilizing an endoglycosidase fusion protein EndoS-linker-EndoH (also referred to as EndoSH, identified by SEQ. ID NO: 1) for trimming of the glycans of cAC10. In the second step the trimmed cAC10 was converted to the azido-modified mAb 13d through the action of His-TnGalNAcT in the presence of 6-$N_3$-GalNAc-UDP (commercially available from GlycoHub) as a substrate. The preparation of the cAC10 bioconjugates is schematically depicted in FIG. 13.

Modified biomolecule 13e, based on the antibody mAb-3 but otherwise identical to 13d, was prepared in the same manner, as described further below.

Example 22: Transient Expression and Purification of cAC10 cAC10 was transiently expressed in CHO K1 cells by Evitria (Zurich, Switzerland) at 5 L scale. The supernatant was purified using a XK 26/20 column packed with 50 mL protein A sepharose. In a single run 5 L supernatant was loaded onto the column followed by washing with at least 10 column volumes of 25 mM Tris pH 7.5, 150 mM NaCl. Retained protein was eluted with 0.1 M Glycine pH 2.7. The eluted cAC10 was immediately neutralized with 1.5 M Tris-HCl pH 8.8 and dialyzed against 25 mM Tris pH 8.0. Next the IgG was concentrated to approximately 20 mg/mL using a Vivaspin Turbo 15 ultrafiltration unit (Sartorius) and stored at −80° C. prior to further use.

Example 23: Transient Expression and Purification of his-TnGalNAcT(33-421)

His-TnGalNAcT(33-421) (identified by SEQ. ID NO: 2) was transiently expressed in CHO K1 cells by Evitria (Zurich, Switzerland) at 5 L scale. The supernatant was purified using a XK 16/20 column packed with 25 mL Ni sepharose excel (GE Healthcare). Each run approximately 1.5 L supernatant was loaded onto the column followed by washing with at least 10 column volumes of buffer A (20 mM Tris buffer, 5 mM imidazole, 500 mM NaCl, pH 7.5). Retained protein was eluted with buffer B (20 mM Tris, 500 mM NaCl, 500 mM imidazole, pH 7.5). The buffer of the eluted fractions was exchanged to 25 mM Tris pH 8.0 using a HiPrep H26/10 desalting column (GE Healthcare). The purified protein was concentrated to at least 3 mg/mL using a Vivaspin Turbo 4 ultrafiltration unit (Sartorius) and stored at −80° C. prior to further use.

Example 24: Preparation of Trimmed cAC10 by Means of Fusion Protein EndoSH

Glycan trimming of cAC10 (obtained via transient expression in CHO K1 cells performed by Evitria (Zurich, Switzerland) was performed with fusion protein EndoSH. Thus, cAC10 (14.5 mg/mL) was incubated with EndoSH (1 w/w %) in 25 mM Tris pH 7.5 with 150 mM NaCl for approximately 16 hours at 37° C. The trimmed IgG was dialyzed against 3×1 L of 25 mM Tris-HCl pH 8.0. Mass spectral analysis of a fabricator-digested sample showed three peaks of the Fc/2-fragment belonging to one major product (observed mass 24105 Da, approximately 80% of total Fc/2 fragment), corresponding to core GlcNAc(Fuc)-substituted cAC10, and two minor products (observed masses of 23959 and 24233 Da, approximately 5 and 15% of total Fc/2 fragment), corresponding to core GlcNAc-substituted cAC10 and core GlcNAc(Fuc)-substituted cAC10 with C-terminal lysine.

Example 25: Glycosyltransfer of the 6-$N_3$-GalNAc-UDP to Trimmed cAC10 Under the Action of TnGalNAcT Substrate 6-$N_3$-GalNAc-UDP (11d) is used for the preparation of the modified biomolecule cAC10-(6-$N_3$-GalNAc)$_2$ 13d, suitable as biomolecule in the context of the invention. Trimmed cAC10 (10 mg/mL), obtained by EndoSH treatment of cAC10 as described above in example 24, was incubated with the substrate 6-$N_3$-GalNAc-UDP (2.5 mM, commercially available from GlycoHub) and 0.5 mg/mL His-TnGalNAcT(33-421) (5 w/w %) in 10 mM $MnCl_2$ and 25 mM Tris-HCl pH 8.0 at 30° C. After 3 hours the amount of His-TnGalNAcT(33-421) was increased to a final concentration of 1 mg/mL (10 w/w %) and the reaction was incubated overnight at 30° C. Biomolecule 13d was purified from the reaction mixture on a HiTrap MabSelect SuRe 5 ml column (GE Healthcare) using an AKTA purifier-10 (GE Healthcare). The eluted IgG was immediately neutralized with 1.5 M Tris-HCl pH 8.8 and dialyzed against PBS pH 7.4. Next the IgG was concentrated using an Amicon Ultra-0.5, Ultracel-10 Membrane (Millipore) to a concentration of 23.38 mg/mL. Mass spectral analysis of a fabricator-digested sample showed three peaks of the Fc/2-fragment belonging to one major product (observed mass 24333 Da, approximately 80% of total Fc/2 fragment), corresponding to core 6-$N_3$-GalNAc-GlcNAc(Fuc)-substituted cAC10, and two minor products (observed masses of 24187 and 24461 Da, approximately 5 and 15% of total Fc/2 fragment), corresponding to core 6-$N_3$-GalNAc-GlcNAc-substituted cAC10 and core 6-$N_3$-GalNAc-GlcNAc(Fuc)-substituted cAC10 with C-terminal lysine.

Example 26: Conjugation of 13d with 100 to Obtain Conjugate 113

A bioconjugate according to the invention was prepared by conjugation of compound 100 as linker-conjugate to modified biomolecule 13d as biomolecule. To a solution of cAC10 (azide)$_2$ (13d) (287 μL, 6.7 mg, 23.38 mg/ml in PBS pH 7.4) was added PBS pH 7.4 (133 μL) and compound 100 (27 μL, 10 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 25844 Da, approximately 80% of total Fc/2 fragment), corresponding to the conjugated Fc/2 fragment. RP-HPLC analysis of the reduced sample indicated an average DAR of 1.88.

Example 27: Conjugation of 13d with 108 to Obtain Conjugate 114

A bioconjugate according to the invention was prepared by conjugation of compound 108 as linker-conjugate to modified biomolecule 13d as biomolecule. To a solution of cAC10 (azide)$_2$ (13d) (287 μL, 6.7 mg, 23.38 mg/ml in PBS pH 7.4) was added PBS pH 7.4 (133 μL) and compound 108 (27 μL, 10 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 25928 Da, approximately 70% of total Fc/2 fragment), corresponding to the conjugated Fc/2 fragment. RP-HPLC analysis of the reduced sample indicated an average DAR of 1.85.

Example 28: Conjugation of 13d with 111 to Obtain Conjugate 112

A control bioconjugate was prepared by conjugation of compound 111 as linker-conjugate to modified biomolecule 13d as biomolecule. To a solution of cAC10 (azide)$_2$ (13d)

(287 μL, 6.7 mg, 23.38 mg/ml in PBS pH 7.4) was added PBS pH 7.4 (48.2 μL) compound 111 (111.8 μL, 4 mM solution in DMF). The reaction was incubated at rt overnight followed by purification on a Superdex200 10/300 GL (GE Healthcare) on an AKTA Purifier-10 (GE Healthcare). Mass spectral analysis of the fabricator-digested sample showed one major product (observed mass 25853 Da, approximately 80% of total Fc/2 fragment), corresponding to the conjugated Fc/2 fragment. RP-HPLC analysis of the reduced sample indicated an average DAR of 1.88.

Examples 29-32: In Vivo Efficacy and Toxicity Studies with Trastuzumab and cAC10 ADCs Example 29

In vivo efficacy studies performed with trastuzumab ADCs 95-98 Female SHO mice (Crl:SHO-Prkdcscid Hrhr, 6- to 9-week-old at the beginning of the experimental phase, obtained from Charles River Laboratories, L'Arbresles, France) were anaesthetized with ketamine/xylazine, the skin was aseptized with a chlorhexidine solution, incised at the level of the interscapular region, a 20 mm³ tumour fragment 20 (HBCx-13B breast cancer patient-derived xenograft model) was placed in the subcutaneous tissue and the skin was closed with clips. When the tumour volume was in the range of 60 to 200 mm³, groups of four mice were injected i.v. with either vehicle, 95 (at 3 mg/kg and 9 mg/kg), 96 (at 3 mg/kg and 9 mg/kg), 97 (at 3 mg/kg and 9 mg/kg), 98 (at 3 mg/kg and 9 mg/kg). Tumours were measured twice weekly.

Figure 14:
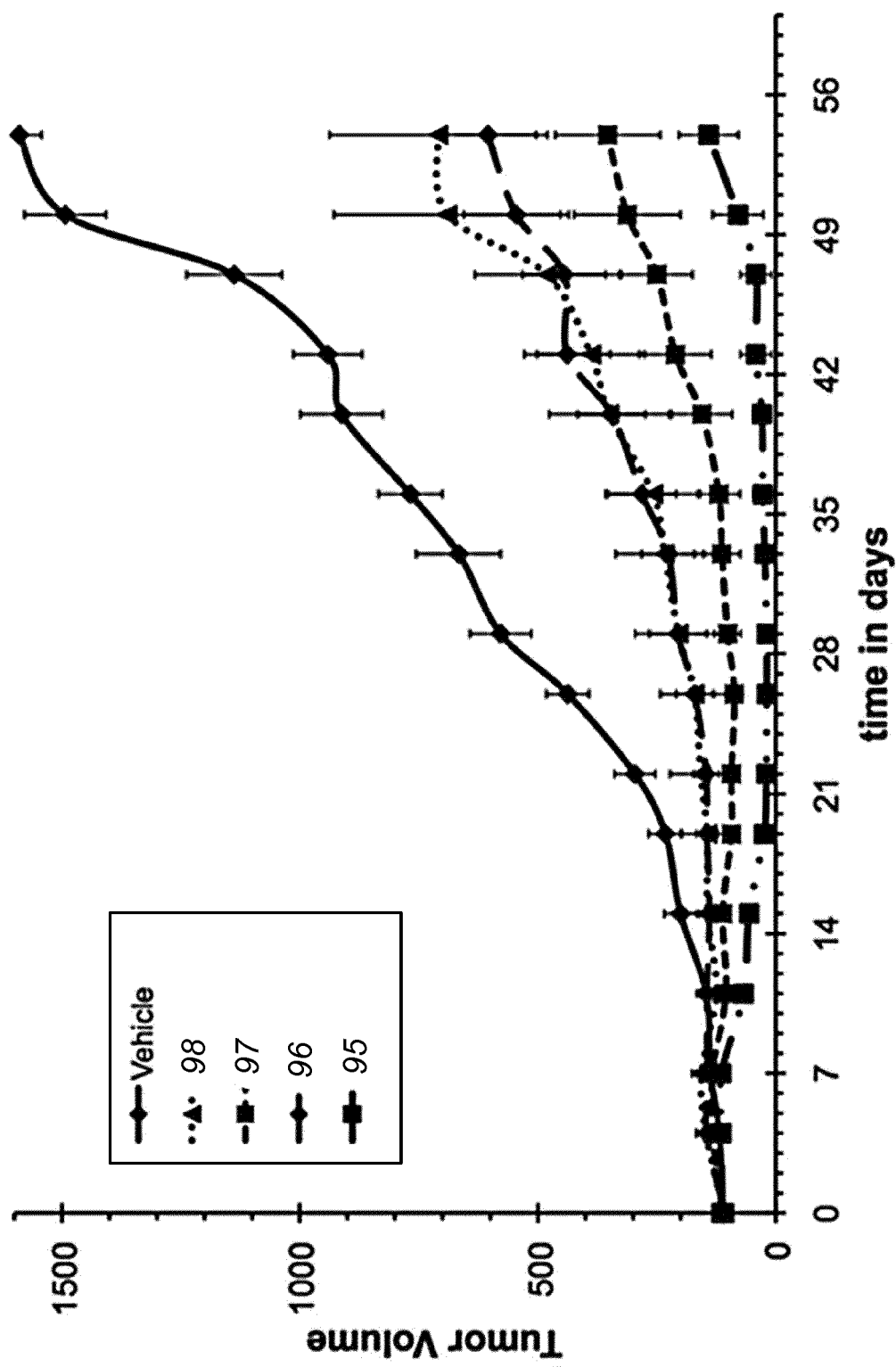
FIG. 14 is a graph of the results of Example 29, wherein the tumour volume (in mm$^3$) is depicted over time using two bioconjugates according to the invention (95 and 97) and two the same bioconjugates only having a linker outside the present invention (96 and 98).

The results on tumour volume are depicted in FIG. 14. The type of linker was found to have a significant effect on tumour volume. The ADCs containing the linkers according to the invention (95 and 97) significantly outperform the ADC with the PEG-linker (96 and 98).

Example 30: In Vivo Efficacy Studies Performed with cAC10 ADCs 112-114

CR female CB.17 SCID mice, 8- to 12-week-old at the beginning of the experimental phase, obtained from Charles River Laboratories, USA) were injected with 1×10⁷ KARPAS-299 tumour cells in a 50% Matrigel subcutaneous in the flank (Karpas-299 cell xenograft model). When the tumour volume was in the range of 100-150 mm³, groups of eight mice were injected i.v. with either vehicle, 112 (at 1 mg/kg), 113 (at 1 mg/kg), and 114 (1 mg/kg). Tumors were measured twice weekly.

Figure 15:
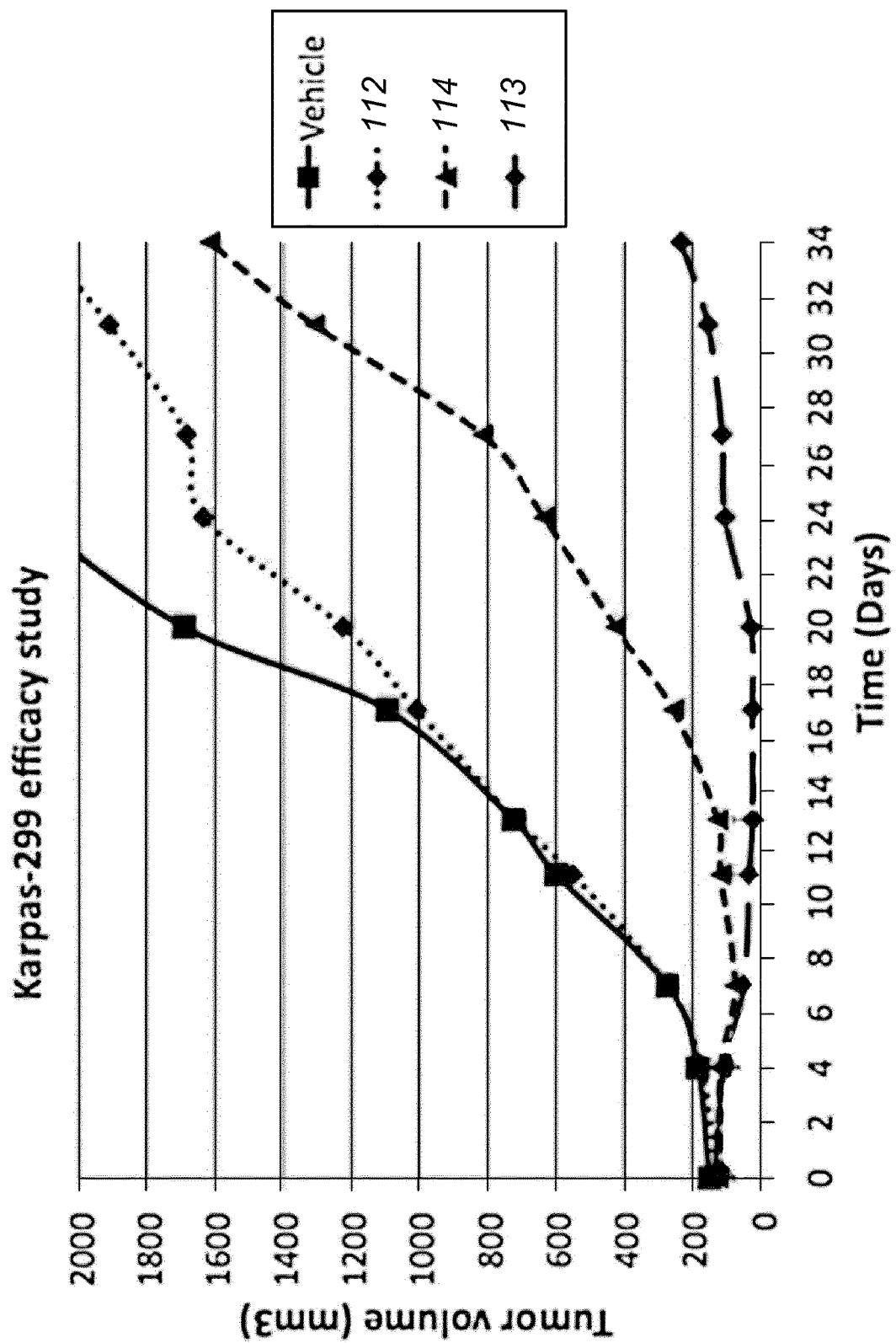
FIG. 15 is a graph of the results of Example 30, wherein the median tumour volume (in mm$^3$) is depicted over time using two bioconjugates according to the invention (113 and 114) and the same bioconjugate only having a linker outside the present invention (112).

The results on tumour volume are depicted in FIG. 15. The type of linker was found to have a significant effect on tumour volume. The ADCs containing the linkers according to the invention (113 and 114) significantly outperform the ADC with the PEG-linker (112).

Example 31: Rat Safety Studies Performed with Trastuzumab ADCs 97 and 98

Sprague Dawley rats (3 males and 3 females per group): OFA:SD, 6-week-old at the beginning of the experimental phase, obtained from Charles River Laboratories, Saint-Germain-Nuelles, France, were treated with 97 ((1) at 20 mg/kg and (2) 40 mg/kg), or 98 ((1) at 20 mg/kg and (2) 40 mg/kg) intravenous (bolus) injection using a microflex infusion set introduced into a tail vein (2 mL/kg at 1 mL/min). One group of animals (control) was treated with vehicle. After dosing, all animals were maintained for a 5-day observation period. Surviving animals were killed on day 5. Each animal were weighed at the time of randomization/selection, prior to dosing (day 0) and on days 2 and 4. All animals (including any found dead or killed moribund) were submitted to full necropsy procedures. Histopathological examinations of the liver, spleen and sciatic nerve was performed for all animals. Blood samples (including for animals killed moribund) were collected and subjected to determination of both haematological as well as serum clinical chemistry parameters.

Figure 16A:
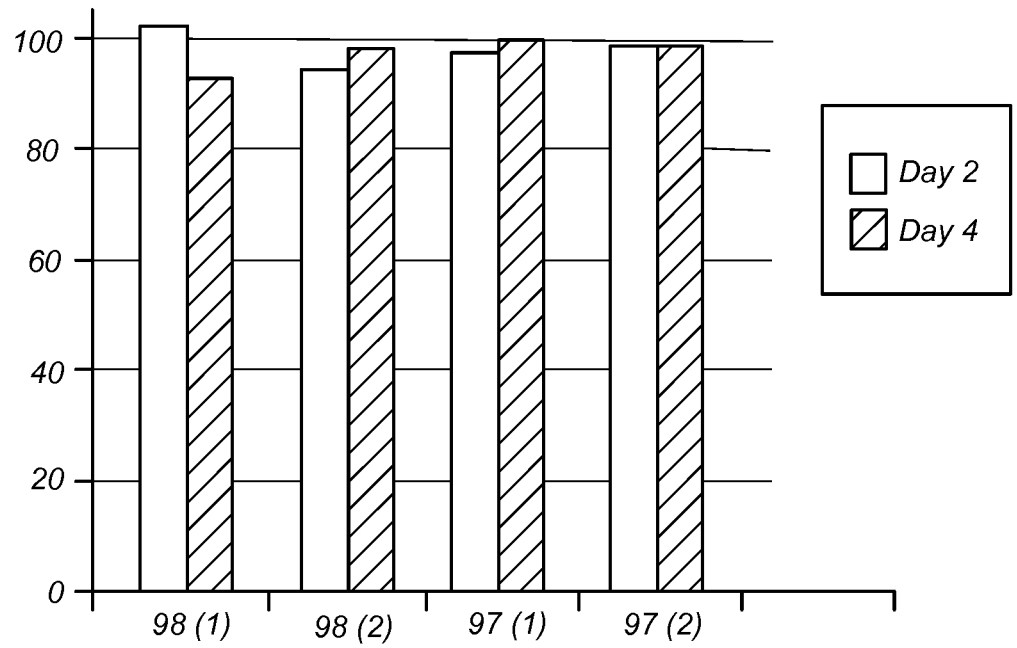
FIG. 16A and FIG. 16B show respectively the platelet count and body weight (both in % of control) on day 2 and 4.
Figure 16B:
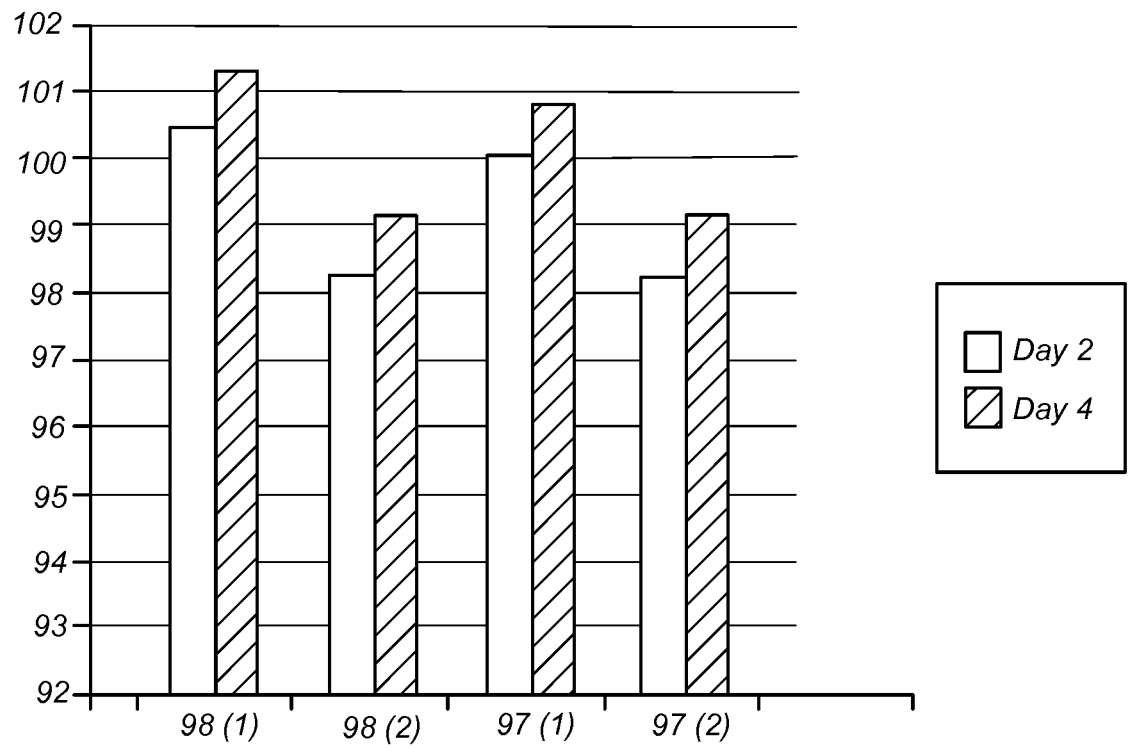

The results on platelet count and body weight are depicted in FIG. 16, and demonstrate that the animals were able to tolerate the conjugate according to the invention (97) and the conjugate with a prior art linker (98) equally well. No significant differences in platelet count and body weight were observed, while both parameters decreased rapidly for the vehicle-treated rats.

Examples 32-42: Preparation of Linker-Conjugates 121, 124, 129 and 130

The synthesis of linker-conjugates 124, 126 and 130 according to the invention are described herein, as well as of control linker-conjugate 121, 125 and 129.

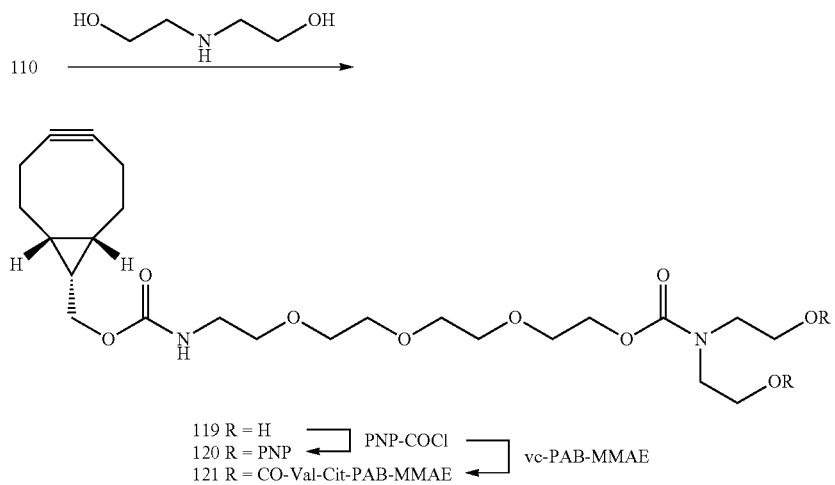

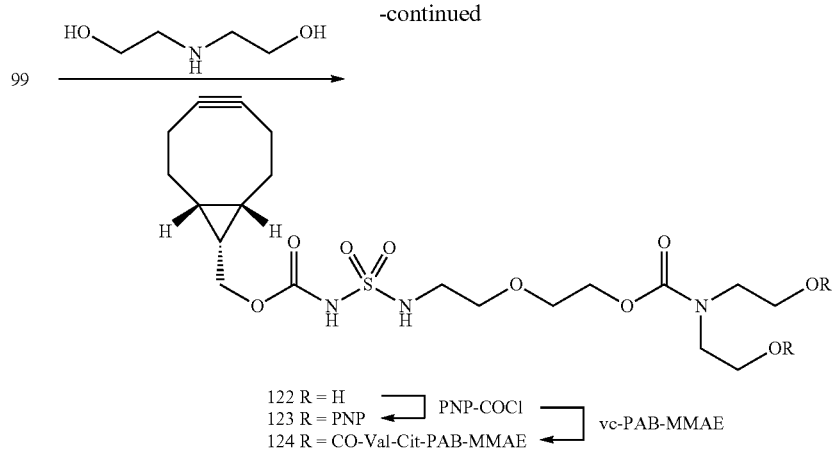

122 R = H
123 R = PNP  ← PNP-COCl
124 R = CO-Val-Cit-PAB-MMAE  ← vc-PAB-MMAE

Example 32: Preparation of Compound 119

To solution 110 (0.90 g; 1.69 mmol) in DCM (50 mL) were added a solution of diethanolamine (DEA, 231 mg; 2.20 mmol) in DMF (7 mL) and Et$_3$N (707 µL; 513 mg; 5.07 mmol). The resulting mixture was stirred at rt for 43 h and washed with a saturated aqueous solution of NH$_4$Cl (50 mL). The aqueous phase was extracted with DCM (50 mL) and the combined organic layers were dried (Na$_2$SO$_4$) and concentrated. The residue was purified by flash column chromatography (DCM→MeOH/DCM 1/9). The product was obtained as a colourless film (784 mg; 1.57 mmol; 93%). $^1$H NMR (400 MHz, CDCl$_3$) δ (ppm) 5.67-5.60 (m, 1H), 4.32-4.27 (m, 2H), 4.14 (d, J=8.4 Hz, 2H), 3.89-3.79 (m, 4H), 3.75-3.60 (m, 10H), 3.58-3.53 (m, 2H), 3.53-3.44 (m, 4H), 3.40-3.33 (m, 2H), 2.35-2.18 (m, 6H), 1.62-1.56 (m, 2H), 1.42-1.30 (m, 1H), 1.00-0.88 (m, 2H).

Example 33: Preparation of Compound 120

To solution of 119 (0.78 g; 1.55 mmol) in DCM (20 mL) were added 4-nitrophenyl chloroformate (938 mg; 4.65 mmol) and Et$_3$N (1.08 mL; 784 mg; 7.75 mmol). The resulting mixture was stirred at rt for 17 h and concentrated. The residue was purified twice by flash column chromatography (DCM→MeOH/DCM 1/9 (column 1), 50% EtOAc in heptane→EtOAc (column 2)). The product was obtained as a slightly yellow oil (423 mg; 0.51 mmol; 33%). $^1$H NMR (400 MHz, CDCl$_3$) δ (ppm) 8.31-8.25 (m, 4H), 7.42-7.35 (m, 4H), 5.22-5.14 (m, 1H), 4.48-4.43 (m, 4H), 4.33-4.28 (m, 2H), 4.14 (d, J=8.4 Hz, 2H), 3.78-3.68 (m, 6H), 3.67-3.59 (m, 8H), 3.57-3.51 (m, 2H), 3.39-3.32 (m, 2H), 2.34-2.16 (m, 6H), 1.60-1.55 (m, 2H), 1.40-1.30 (m, 1H), 0.99-0.88 (m, 2H).

Example 34: Preparation of Linker-Conjugate 121

To a solution of 120 (34 mg, 41 µmol) in DMF (400 µL) were added triethylamine (28 µl; 20 mg; 201 µmol) and a solution of vc-PABC-MMAE.TFA (83 mg; 67 µmol) in DMF (1.0 mL). The mixture was diluted with DMF (1200 µL) and left standing for 41 h and 2,2'-(ethylenedioxy)bis(ethylamine) (47 µL, 48 mg, 322 µmol) was added. After 80 min, the reaction mixture was purified by RP HPLC (C18, 30%→90% MeCN (1% AcOH) in water (1% AcOH). The desired product was obtained as a colourless oil (66 mg, 24 µmol, 58% (based on 120). LCMS (ESI$^+$) calculated for C$_{142}$H$_{226}$N$_{22}$O$_{35}$$^{2+}$ (M+2H$^+$) 1400.33 found 1401.08.

Example 35: Preparation of Compound 122

To solution of compound 99 (0.39 g; 0.734 mmol) in DCM (30 mL) were added a solution of diethanolamine (DEA, 107 mg; 1.02 mmol) in DMF (2 mL) and Et$_3$N (305 µL; 221 mg; 2.19 mmol). The resulting mixture was stirred at rt for 17 h and washed with a saturated aqueous solution of NH$_4$Cl (30 mL). The aqueous phase was extracted with DCM (30 mL) and the combined organic layers were dried (Na$_2$SO$_4$) and concentrated. The residue was purified by flash column chromatography (DCM→MeOH/DCM 1/9). The product was obtained as a colourless film (163 mg; 0.33 mmol; 45%). $^1$H NMR (400 MHz, CDCl$_3$) δ (ppm) 6.29 (bs, 1H), 4.33-4.29 (m, 2H), 4.28 (d, J=8.2 Hz, 2H), 3.90-3.80 (m, 4H), 3.69-3.64 (m, 2H), 3.61 (t, J=4.8 Hz, 2H), 3.52 (t, J=5.0 Hz, 4H), 3.32 (t, J=5.1 Hz, 2H), 2.37-2.18 (m, 6H), 1.60-1.55 (m, 2H), 1.39 (quintet, J=8.7 Hz, 1H), 1.05-0.94 (m, 2H).

Example 36: Preparation of Compound 123

To a solution of 122 (163 mg, 0.33 mmol) and 4-nitrophenyl chloroformate (134 mg, 0.66 mmol) in DCM (10 mL) was added Et$_3$N (230 µL; 167 mg; 1.65 mmol). The reaction mixture was stirred for 17 h and concentrated. The residue was purified by flash column chromatography (50% EtOAc in heptane→100% EtOAc). The product was obtained as a colourless oil (69 mg; 0.084 mmol; 25%). $^1$H NMR (400 MHz, CDCl$_3$) δ (ppm) 8.29-8.23 (m, 4H), 7.42-7.35 (m, 4H), 5.81-5.71 (m, 1H), 4.53-4.43 (m, 4H), 4.36-4.30 (m, 2H), 4.25 (d, J=8.2 Hz, 2H), 3.81-3.70 (m, 4H), 3.70-3.65 (m, 2H), 3.62-3.56 (m, 2H), 3.32-3.24 (m, 2H), 2.34-2.14 (m, 6H), 1.60-1.45 (m, 2H), 1.35 (quintet, J=8.7 Hz, 1H), 1.02-0.91 (m, 2H).

Example 37: Preparation of Linker-Conjugate 124

To a solution of 123 (27 mg, 33 µmol) in DMF (400 µL) were added triethylamine (22 µl; 16 mg; 158 µmol) and a solution of vc-PABC-MMAE.TFA (96 mg; 78 µmol) in DMF (1.0 mL). The mixture was left standing for 19 h and 2,2'-(ethylenedioxy)bis(ethylamine) (37 µL, 38 mg, 253 µmol) was added. After 2 h, the reaction mixture was diluted with DMF (100 µL) and purified by RP HPLC (C18, 30%→90% MeCN (1% AcOH) in water (1% AcOH). The desired product was obtained as a colourless film (41 mg, 14.7 µmol, 45%). LCMS (ESI$^+$) calculated for C$_{138}$H$_{219}$N$_{23}$O$_{35}$S$^{2+}$ (M+2H$^+$) 1395.79 found 1396.31.

Example 38: Preparation of Compound 125

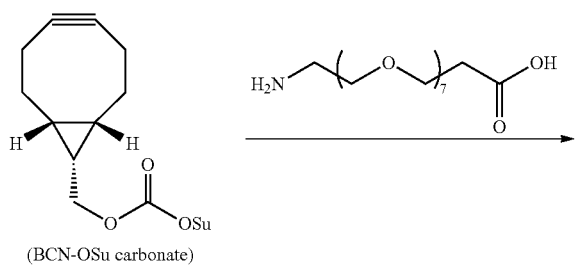
(BCN-OSu carbonate)

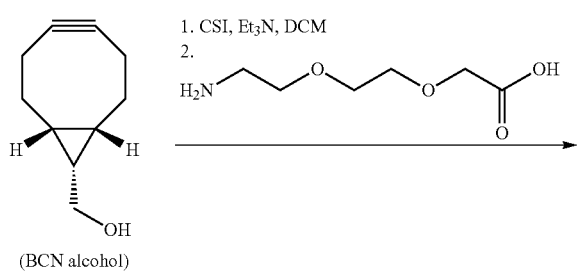
125

A mixture of BCN-OSu carbonate (66 mg, 0.23 mmol), amino-dPEGs-acid (100 mg, 0.23 mmol) and Et$_3$N (69 mg, 94 μL, 0.678 mmol) in THF/water (10 mL/10 mL) was stirred overnight. Potassium phosphate buffer (0.5 M, pH 3.0) was added and the pH was brought to 3.0 through addition of 1N aqueous HCl. The aqueous solution was extracted with EtOAc (20 mL). The organic phase was dried (Na$_2$SO$_4$) and concentrated. The product was obtained as a colourless oil (138 mg, 0.22 mmol; 97%). $^1$H NMR (400 MHz, CDCl$_3$) δ ppm 5.43-5.35 (m, 1H), 4.14 (d, 2H, J=8.0 Hz), 3.77 (t, 2H, J=6.0 Hz), 3.68-3.60 (m, 28H), 3.58-3.53 (m, 2H), 3.40-3.33 (m, 2H), 2.60 (t, 2H, J=6.0 Hz), 2.35-2.16 (m, 6H), 1.65-1.50 (m, 2H), 1.40-1.30 (m, 1H), 1.00-0.85 (m, 2H).

Example 39: Preparation of Compound 126

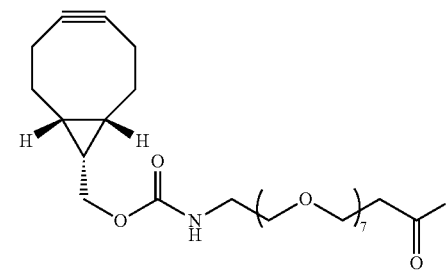
(BCN alcohol)

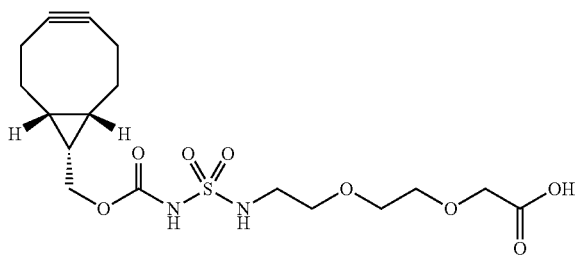
126

A solution of BCN alcohol (0.384 g, 2.55 mmole) in MeCN (25 mL) under a N$_2$ atmosphere was cooled to 0° C., and chlorosulfonyl isocyanate was added (CSI) was added dropwise (0.255 mL, 415 mg, 2.93 mmole, 1.15 equiv.). After stirring for 15 minutes, Et$_3$N was added dropwise (1.42 mL, 1.03 g, 10.2 mmole, 4 equiv.) and stirring was continued for another 10 minutes. Next, a solution of 2-(2-(2-aminoethoxy)ethoxy)acetic acid (1.0 g, 6.1 mmole, 2.4 equiv.) in H$_2$O (5 mL) was added and the reaction mixture was stirred to room temperature for 2 h. After this time, CHCl$_3$ (50 mL) and H$_2$O (100 mL) were added, and the layers were separated. To the aqueous layer in a separatory funnel was added CH$_2$Cl$_2$ (100 mL) and the pH was adjusted to 4 with 1 N HCl, before separation of layers. The water layer was extracted twice with CH$_2$Cl$_2$ (2×100 mL), the organic layers were combined and dried (Na$_2$SO$_4$), filtered and concentrated. The residue was purified by flask column chromatography on silica, elution with CH$_2$Cl$_2$ to 20% MeOH in CH$_2$Cl$_2$. Yield 0.42 g (1.0 mmole, 39%) of 126 as a colourless sticky wax.

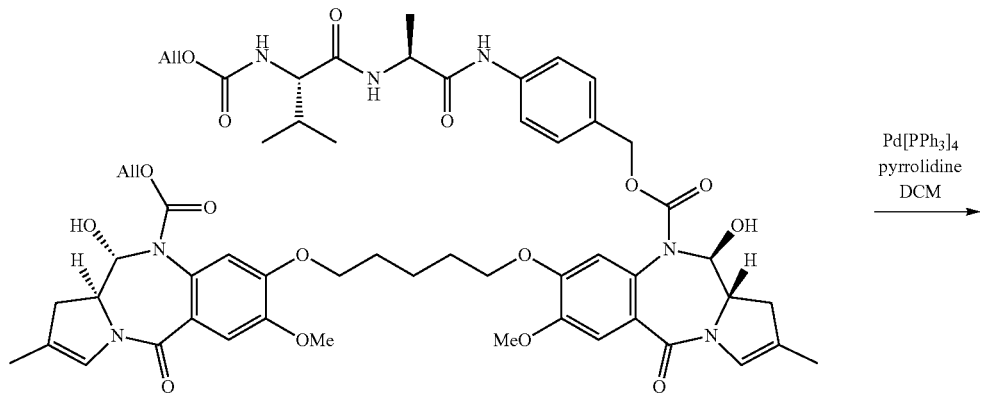
127

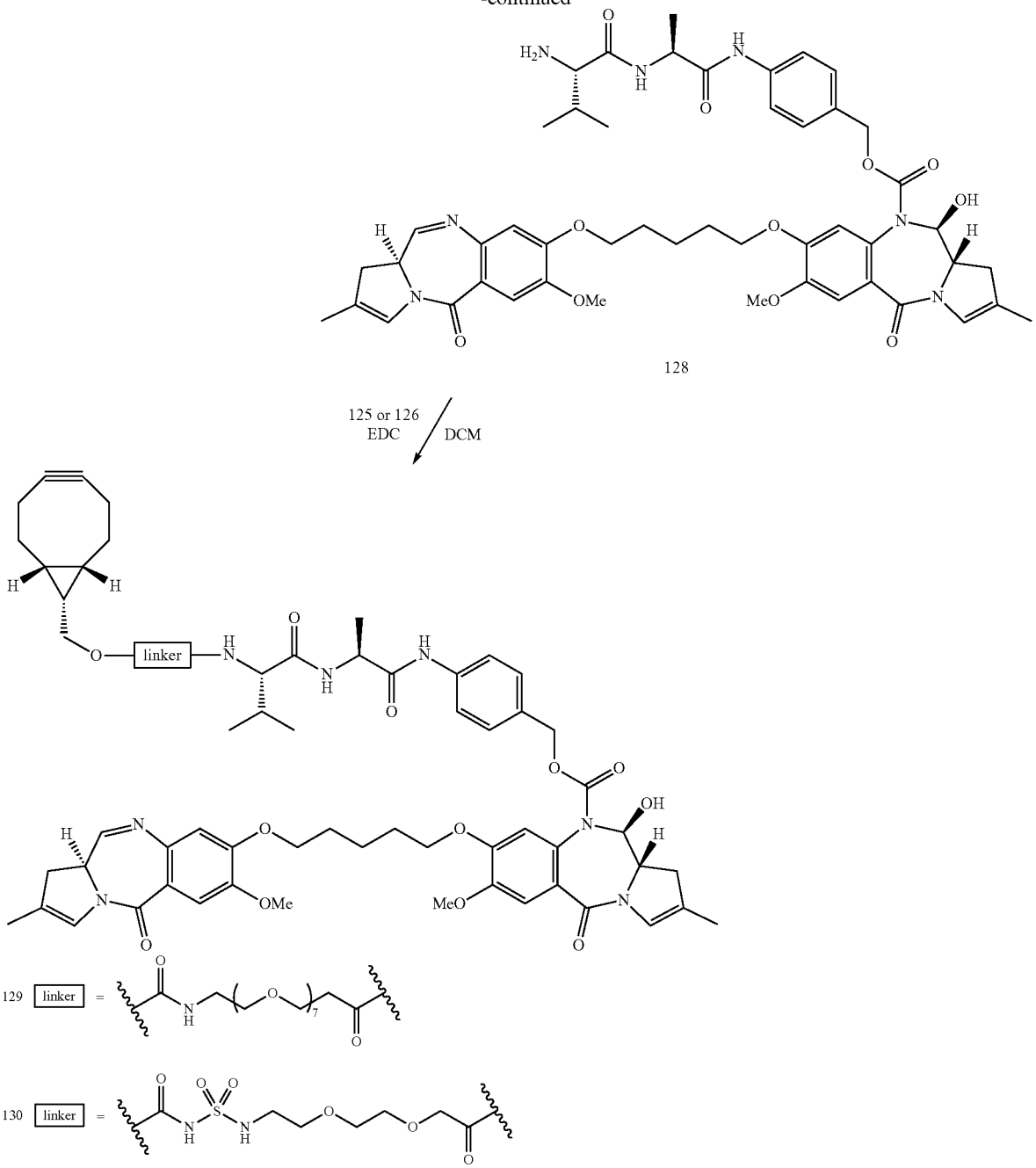

Example 40: Preparation of Compound 128

Palladium tetrakistriphenylphosphine Pd(PPh$_3$)$_4$ (4.8 mg, 4.15 µmol) is weighed and put under an atmosphere of N$_2$. A solution of pyrrolidine (5.0 µL, 4.3 mg, 60 µmol) in DCM (1 mL) is degassed by bubbling N$_2$ through the solution. A solution of 127 (27 mg, 24 µmol) in DCM (6 mL) is degassed by bubbling N$_2$ through the solution. While N$_2$ is still bubbled through the solution, the degassed solution of pyrrolidine is added. The weighed Pd(PPh$_3$)$_4$ is dissolved in CH$_2$Cl$_2$ (1 mL) and 0.9 mL of this solution is added. After 50 min of bubbling of N$_2$, CH$_2$Cl$_2$ (25 mL) is added and the mixture is washed with aqueous saturated NH$_4$Cl (25 mL). After separation, the aqueous layer is extracted with CH$_2$Cl$_2$ (2×25 mL). The combined organic layers are dried (Na$_2$SO$_4$) and concentrated. The residue is purified by RP-HPLC (30-90% MeCN (0.1% formic acid) in H$_2$O (0.1% formic acid). The combined fractions are passed through SPE (HCO$_3$) columns and concentrated. After addition of MeCN (50 mL) the mixture is again concentrated. The resulting residue is used in the next step.

Example 41: Preparation of Compound 129

A mixture of 128 (6.8 mg, 7.4 µmol) and 125 (5.6 mg, 9.0 µmol) in CHCl$_3$ (400 µL) was added to EDC·HCl (2.6 mg, 13.5 µmol). The mixture was left standing for 1.5 h and EDC·HCl (2.6 mg, 13.6 µmol) and 2,2'-(ethylenedioxy)bis (ethylamine) (1.3 μL, 1.3 mg, 8.8 μmol) were added. The mixture was left standing overnight and diluted with DCM (10 mL). The organic solution was washed with aqueous saturated NH$_4$Cl, dried (Na$_2$SO$_4$) and concentrated. The residue was purified via reversed phase (C18) HPLC chromatography (30-90% MeCN (no acid) in H$_2$O (0.01% formic acid). The HPLC collection tubes are filled with 5% aqueous (NH$_4$)HCO$_3$ before collection. The fractions, containing the desired product were pooled and extracted with dichloromethane (10 mL). The organic phase was dried (Na$_2$SO$_4$) and concentrated, which afforded the desired product (4.6 mg, 3.0 μmol, 41%). LCMS (ESI$^+$) calculated for $C_{79}H_{109}N_{80}O_{22}^+$ (M+H$^+$) 1521.77 found 1521.99.

Example 42: Preparation of Compound 130

To a solution of 128 in CHCl$_3$ (5 mL) is added a solution of 126 (15 mg, 36 μmol) in CHCl$_3$ (0.8 mL). The resulting mixture is added to solid EDC·HCl (4.7 mg, 25 μmol), CHCl$_3$ (5 mL) was added and the mixture was left standing for 16 h. DCM (30 mL) is added and the resulting mixture is washed with water (30 mL). After separation, the aqueous phase is extracted with DCM (30 mL). The combined organic layers are dried (Na$_2$SO$_4$) and concentrated. The residue is purified by RP-HPLC (30-90% MeCN (no acid) in H$_2$O (0.01% formic acid). The HPLC collection tubes are filled with 5% aqueous (NH$_4$)HCO$_3$ before collection. The combined HPLC fractions are extracted with DCM (3×20 mL). The combined organic layers are dried (Na$_2$SO$_4$) and concentrated. The product 130 is obtained as slightly yellow oil (21 mg, 16 μmol, mw 1323 g/mole, 67% over two steps from 127).

Examples 43-44: Preparation of cAC10 Bioconjucates

Example 43: Conjugation of 13d with 121 to Obtain Conjugate 115

A bioconjugate according to the invention was prepared by conjugation of compound 121 as linker-conjugate to azide-modified cAC10 as biomolecule 13d. To a solution of cAC10-(6-N$_3$-GalNAc)$_2$ (13d) (8.408 mL, 246.0 mg, 29.3 mg/ml in PBS pH 7.4) was added propylene glycol (11.909 mL) and compound 121 (410.6 μL, 40 mM solution in DMF). The reaction was incubated at rt for approximately 40 hrs. The reaction mixture was dialyzed to PBS pH 7.4 and purified on a HiLoad 26/600 Superdex200 PG (GE Healthcare) on an AKTA Purifier-10 (GE Healthcare). Mass spectral analysis of the fabricator-digested sample showed one major product (observed mass 27132 Da, approximately 80% of total Fc/2 fragment), corresponding to the conjugated Fc/2 fragment. RP-HPLC analysis of the reduced sample indicated an average DAR of 3.81.

Example 44: Conjugation of 13d with 124 to Obtain Conjugate 116

A bioconjugate according to the invention was prepared by conjugation of compound 124 as linker-conjugate to azide-modified cAC10 as biomolecule 13d. Thus, to a solution of cAC10-(6-N$_3$-GalNAc)$_2$ (13d) (9.95 mL, 205 mg, 20.7 mg/ml in PBS pH 7.4) was added PBS pH 7.4 (1.0 mL), DMF (2.568 mL) and compound 124 (171.7 μL, 40 mM solution in DMF). The reaction was incubated at rt overnight followed by dialysis and purification on a HiLoad 26/600 Superdex200 PG (GE Healthcare) on an AKTA Purifier-10 (GE Healthcare). Mass spectral analysis of the fabricator-digested sample showed one major product (observed mass 27124 Da, approximately 80% of total Fc/2 fragment), corresponding to the conjugated Fc/2 fragment. RP-HPLC analysis of the reduced sample indicated an average DAR of 3.79.

Examples 45-48: Preparation of mAb-3 Bioconjucates

The preparation of modified biomolecule 13e is performed according to the a similar procedure as is described above for cAC10 utilizing an endoglycosidase fusion protein EndoSH for trimming of the glycans of mAb-3. In the second step the trimmed mAb-3 was converted to the azido-modified antibody 13e through the action of His-TnGalNAcT in the presence of 6-N$_3$-GalNAc-UDP (commercially available from GlycoHub) as a substrate.

Example 45: Preparation of Trimmed mAb-3 by Means of Fusion Protein EndoSH

Glycan trimming of mAb-3 was performed with fusion protein EndoSH. To a solution of mAb-3 (23.21 mL, 200 mg, 8.6 mg/ml in PBS pH 7.4) was added EndoSH (526 μL, 2.0 mg, 3.8 mg/ml in 25 mM Tris-HCl pH 7.5). The reaction was incubated for approximately 16 hours at 37° C. Mass spectral analysis of a fabricator-digested sample showed one main peak of the Fc/2-fragment belonging to one major product (observed mass 24139 Da, approximately 90% of total Fc/2 fragment), corresponding to core GlcNAc(Fuc)-substituted mAb-3. The trimmed IgG was dialyzed against 2×1 L of 25 mM Tris-HCl pH 8.0 with 150 mM NaCl followed by concentration to 21.5 mg/mL by spinfiltration (Amicon Ultra-4, Ultracel-10 Membrane, Millipore)

Example 46: Glycosyltransfer of the 6-N$_3$-GalNAc-UDP to Trimmed mAb-3 Under the Action of TnGalNAcT Substrate 6-N$_3$-GalNAc-UDP (11d) is used for the preparation of the modified biomolecule mAb-3-(6-N$_3$-GalNAc)$_2$ 13e, suitable as biomolecule in the context of the invention. To a solution of trimmed mAb-3 (9.297 mL, 200 mg, 21.5 mg/ml in 25 mM Tris-HCl pH 8.0 with 150 mM NaCl), as obtained in example 48, was added MnCl$_2$ (133 μL, 0.1 M in MQ), His-TnGalNAcT(33-421) (3.112 mL, 15 mg, 4.82 mg/ml in 25 mM Tris-HCl pH 8.0) and 6-N$_3$-GalNAc-UDP (1.0 mL, 63 mg, 0.1 M in MQ). The reaction was incubated for approximately 16 hours at 30° C. Biomolecule 13e was purified from the reaction mixture on a HiTrap MabSelect SuRe 5 ml column (3 columns connected in series, GE Healthcare) using an AKTA purifier-10 (GE Healthcare). The eluted IgG was immediately neutralized with 1.5 M Tris-HCl pH 8.8 and dialyzed against PBS pH 7.4. Next the IgG was concentrated using an Amicon Ultra-4, Ultracel-10 Membrane (Millipore) to a concentration of 20.17 mg/mL. Mass spectral analysis of a fabricator-digested sample showed one main peak of the Fc/2-fragment belonging to one major product (observed mass 24365 Da, approximately 90% of total Fc/2 fragment), corresponding to core 6-N$_3$-GalNAc-GlcNAc(Fuc)-substituted mAb-3.

Example 47: Conjugation of 13e with 129 to Obtain Conjugate 117

A bioconjugate according to the invention was prepared by conjugation of compound 129 as linker-conjugate to azide-modified mAb-3 as biomolecule. Thus, to a solution of mAb-3-(6-N$_3$-GalNAc)$_2$ (13e) (1.667 mL, 40.6 mg, 24.6 mg/ml in PBS pH 7.4) was added PBS pH 7.4 (636 µL), DMF (163 µL) and compound 129 (244 µL, 10 mM solution in DMF). The reaction was incubated at rt overnight followed by dialysis and purification on a Superdex200 10/300 GL (GE Healthcare) on an AKTA Purifier-10 (GE Healthcare). Mass spectral analysis of the fabricator-digested sample showed one major product (observed mass 25890 Da, approximately 90% of total Fc/2 fragment), corresponding to the conjugated Fc/2 fragment. RP-HPLC analysis of the reduced sample indicated an average DAR of 1.96.

Example 48: Conjugation of 13e with 130 to Obtain Conjugate 118

A bioconjugate according to the invention was prepared by conjugation of compound 130 as linker-conjugate to azide-modified mAb-3 as biomolecule. Thus, to a solution of mAb-3-(6-N$_3$-GalNAc)$_2$ (13e) (1.667 mL, 40.6 mg, 24.6 mg/ml in PBS pH 7.4) was added PBS pH 7.4 (636 µL), DMF (190 µL) and compound 130 (217 µL, 10 mM solution in DMF). The reaction was incubated at rt overnight followed by dialysis and purification on a Superdex200 10/300 GL (GE Healthcare) on an AKTA Purifier-10 (GE Healthcare). Mass spectral analysis of the fabricator-digested sample showed one major product (observed mass 25691 Da, approximately 90% of total Fc/2 fragment), corresponding to the conjugated Fc/2 fragment. RP-HPLC analysis of the reduced sample indicated an average DAR of 1.98.

Examples 49-51: In Vivo Efficacy and Toxicity Studies with mAb-3 ADCs

Example 49: In Vivo Efficacy Studies Performed with cAC10 ADCs 115 and 116

Figure 17A:
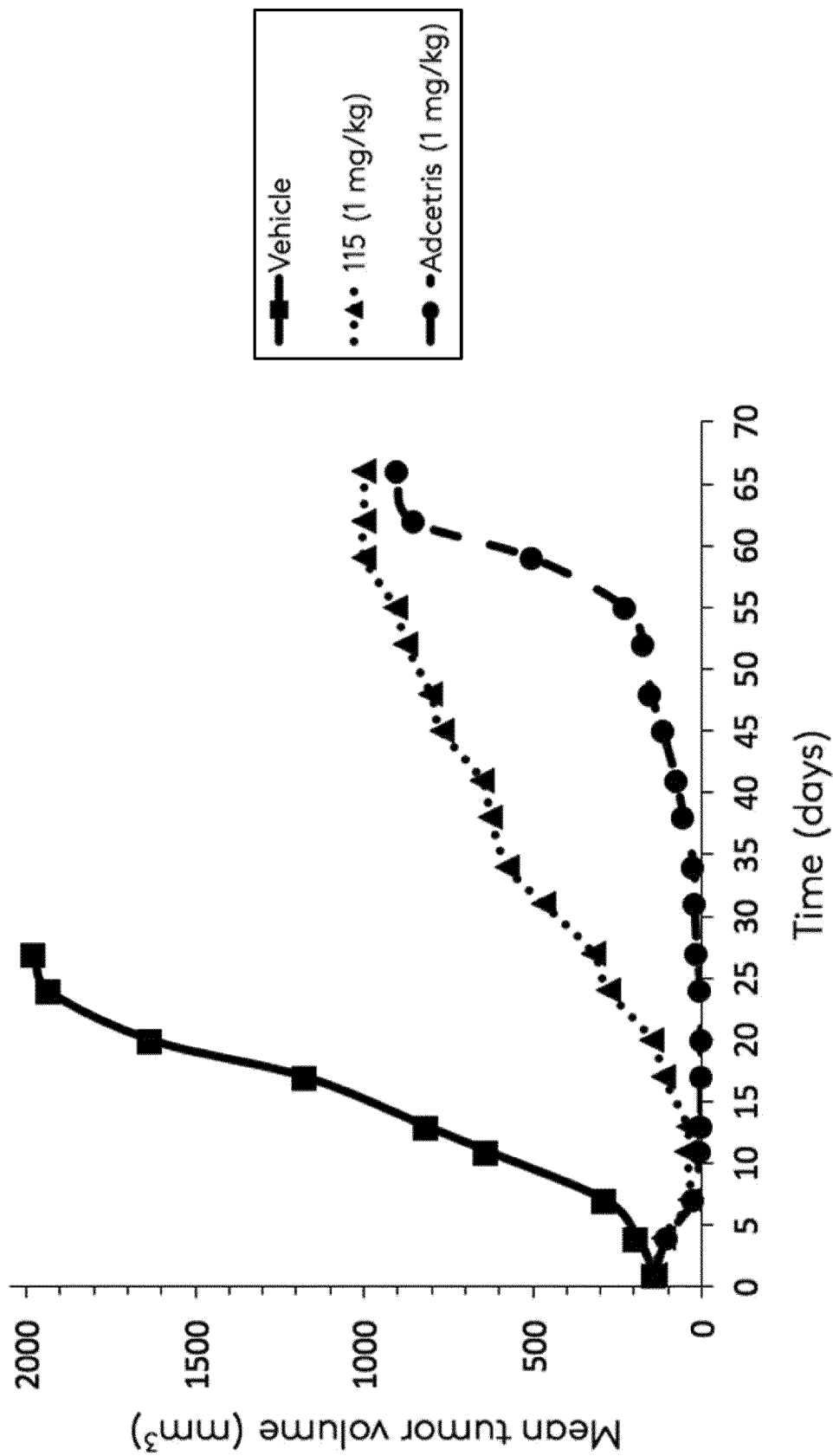

CR female CB.17 SCID mice, 8- to 12-week-old at the beginning of the experimental phase, obtained from Charles River Laboratories, USA) were injected with 1×107 KARPAS-299 tumour cells in a 50% Matrigel subcutaneous in the flank (Karpas-299 cell xenograft model). When the tumour volume was in the range of 100-150 mm$^3$, groups of eight mice were injected i.v. with either vehicle, 115 (at 1 and 2 mg/kg) and Adcetris® (at 1 and 2 mg/kg). Tumours were measured twice weekly. The results on tumour volume are depicted in FIG. 17a.

In a separate but identical study, groups of eight mice were injected with either vehicle, 116 (at 1 mg/kg) and Adcetris® (1 mg/kg). Tumours were measured twice weekly. The results on tumour volume are depicted in FIG. 17b.

The type of linker was found to have a significant effect on tumour volume. The ADC containing the linkers according to the invention (116) significantly outperformed Adcetris® at the same dose, while in another study ADC with the prior art PEG-linker (115) efficacy is smaller than that of Adcetris® at the same dose.

Example 50: Rat Safety Studies Performed with cAC10 ADCs 112-114

Female Wistar rats (2 females per group), 5-6-week-old at the beginning of the experimental phase, obtained from Charles River Laboratories, USA, were treated with 112 (40, 60, 70 or 80 mg/kg), 113 (40, 60, 70 or 80 mg/kg) or 114 (40, 60, 70 or 80 mg/kg). The test items were administered via intravenous (bolus) injection using a microflex infusion set introduced into a tail vein (2 mL/kg at 1 mL/min). One group of animals was treated with vehicle (control). After dosing, all animals were maintained for a 12-day observation period. Surviving animals were euthanized on day 12. Each animal was weighed at the time of randomization/selection, prior to dosing (day 0) and on all subsequent days up to day 12. Any individual animal with a single observation of >30% body weight loss or three consecutive measurements of >25% body weight loss was euthanized. All animals (including any found dead or killed moribund) were submitted to full necropsy procedures. Histopathological examinations of the liver, spleen and sciatic nerve was performed for all animals. Blood samples (including for animals killed moribund) were collected and subjected to determination of both haematological as well as serum clinical chemistry parameters.

Figure 18A:
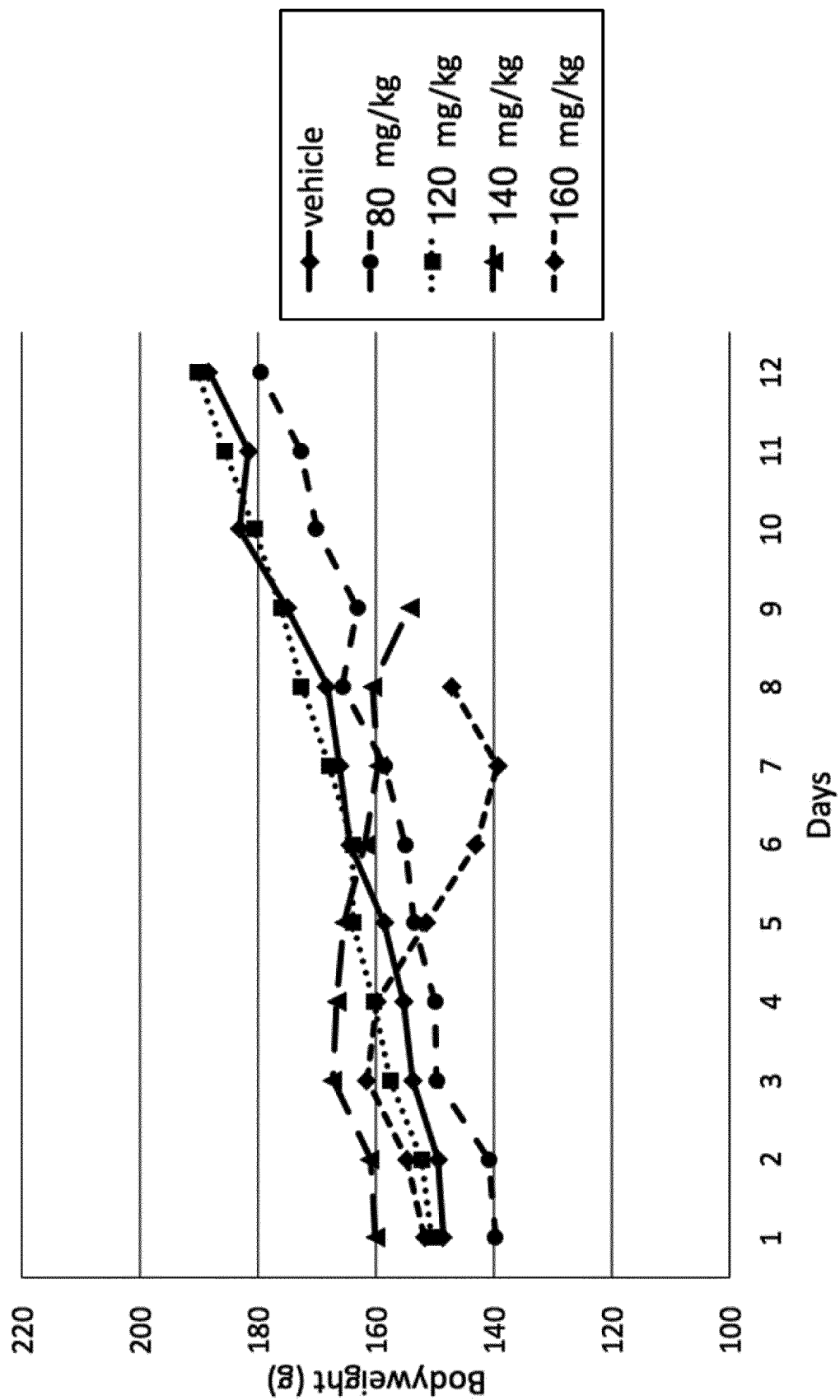
FIGS. 18a-c show the safety results of Example 50, wherein rats were treated with 112, 113 or 114 (all DAR2 ADCs with same antibody brentuximab and the same payload MMAE).
Figure 18B:
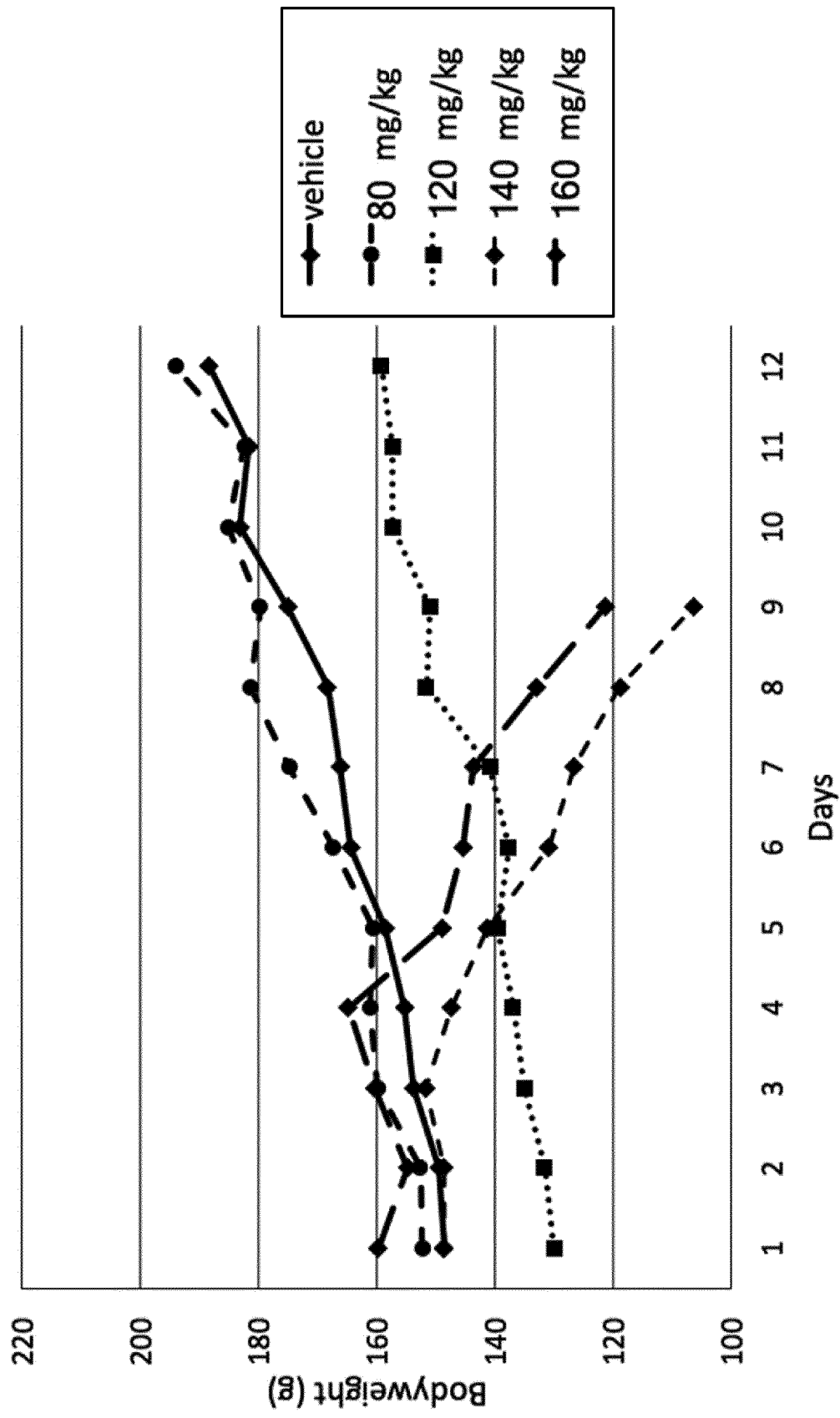
Figure 18C:
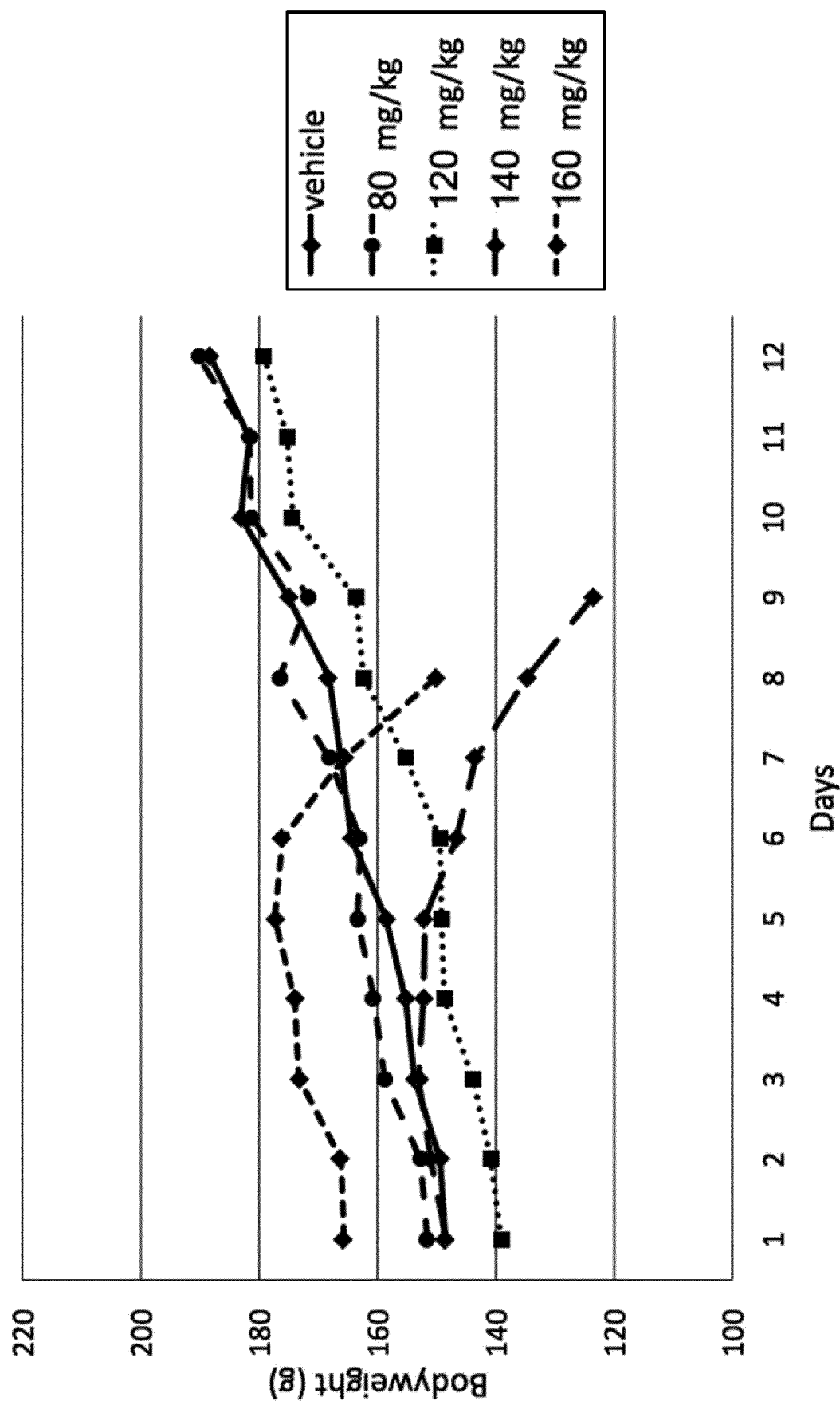

The results for the percentage bodyweight loss of the rats for the different dose regimes per ADC are depicted in FIG. 18a-c. It is clear form these results that the maximum tolerated dose (MTD) for all 112-114 is found to be 60 mg/kg.

Example 51: Rat Safety Studies Performed with cAC10 ADCs 115, 116 and Adcetris®

Female Wistar rats (2 females per group), 5-6-week-old at the beginning of the experimental phase, obtained from Charles River Laboratories, USA, were treated with 115 (80, 120, 140 or 160 mg/kg), 116 (80, 120, 40 or 160 mg/kg) or Adcetris® (15, 20 or 40 mg/kg). The test items were administered via intravenous (bolus) injection using a microflex infusion set introduced into a tail vein (2 mL/kg at 1 mL/min). One group of animals was treated with vehicle (control). After dosing, all animals were maintained for a 12-day observation period. Surviving animals were euthanized on day 12. Each animal was weighed at the time of randomization/selection, prior to dosing (day 0) and on all subsequent days up to day 12. Any individual animal with a single observation of >30% body weight loss or three consecutive measurements of >25% body weight loss was euthanized. All animals (including any found dead or killed moribund) were submitted to full necropsy procedures. Histopathological examinations of the liver, spleen and sciatic nerve was performed for all animals. Blood samples (including for animals killed moribund) were collected and subjected to determination of both haematological as well as serum clinical chemistry parameters.

Figure 19A:
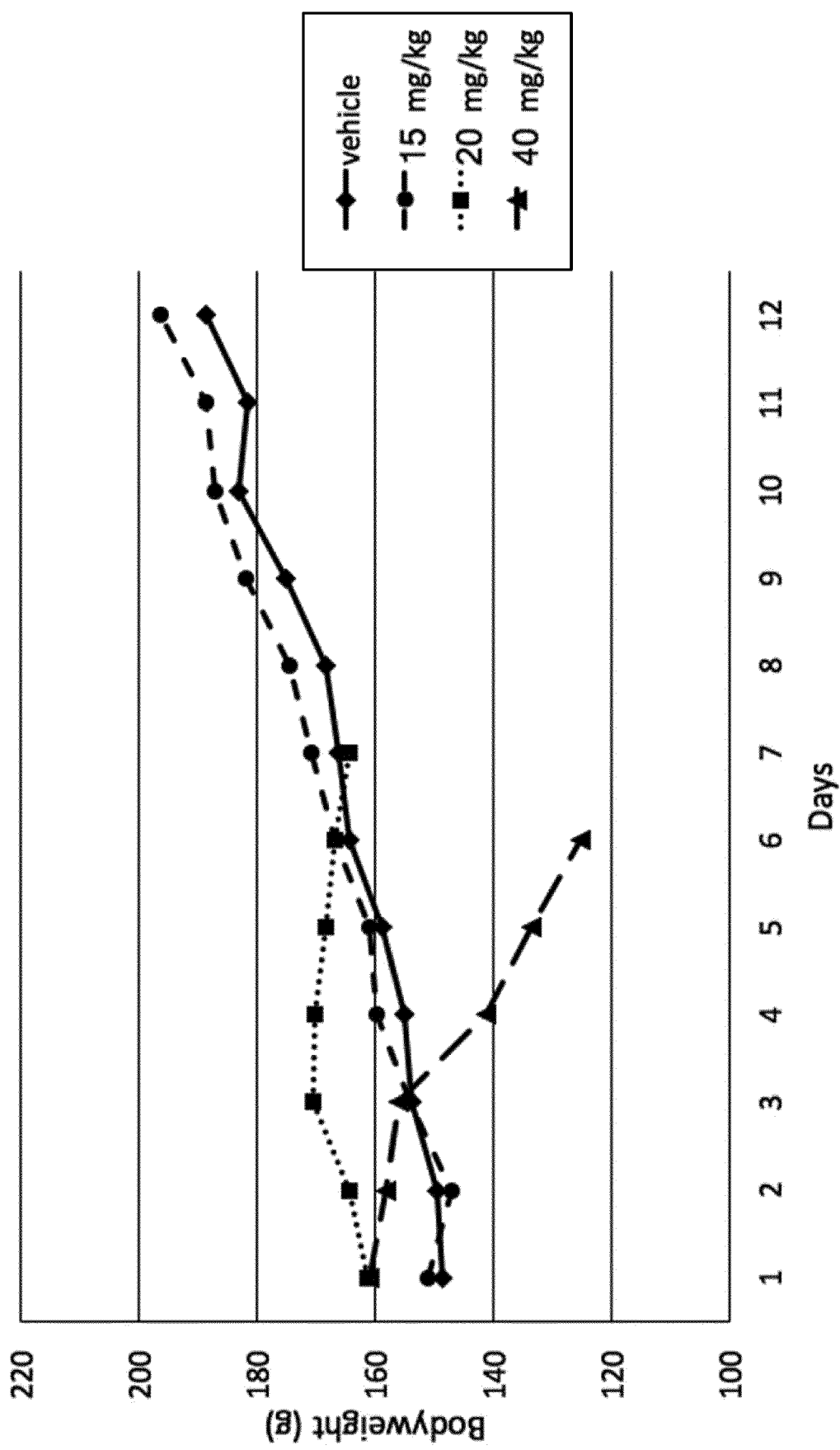
Figure 19B:
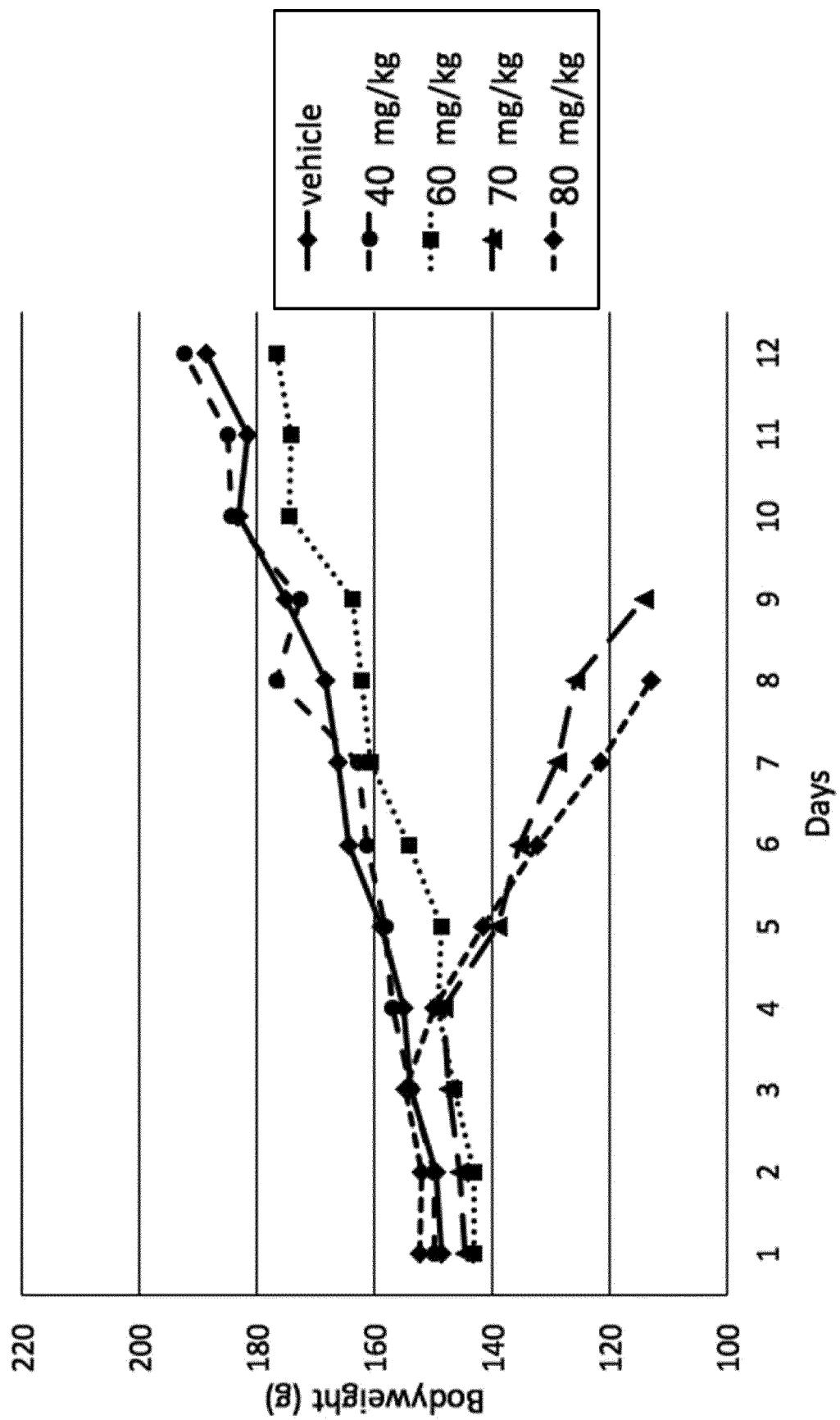

The results for the percentage bodyweight loss of the rats for the different dose regimes per ADC are depicted in FIG. 19a-c. It is clear form these results that the maximum tolerated dose (MTD) for Adcetris is between 15 mg/kg and 20 mg/kg, whereas the MTDs for ADCs 115 and 116 were found to be 120 mg/kg.

Examples 52-53: In Vivo Efficacy and Toxicity Studies with mAb-3 ADCs

Example 52: In Vivo Efficacy Studies Performed with mAb-3 ADCs 117 and 118

Figure 20:
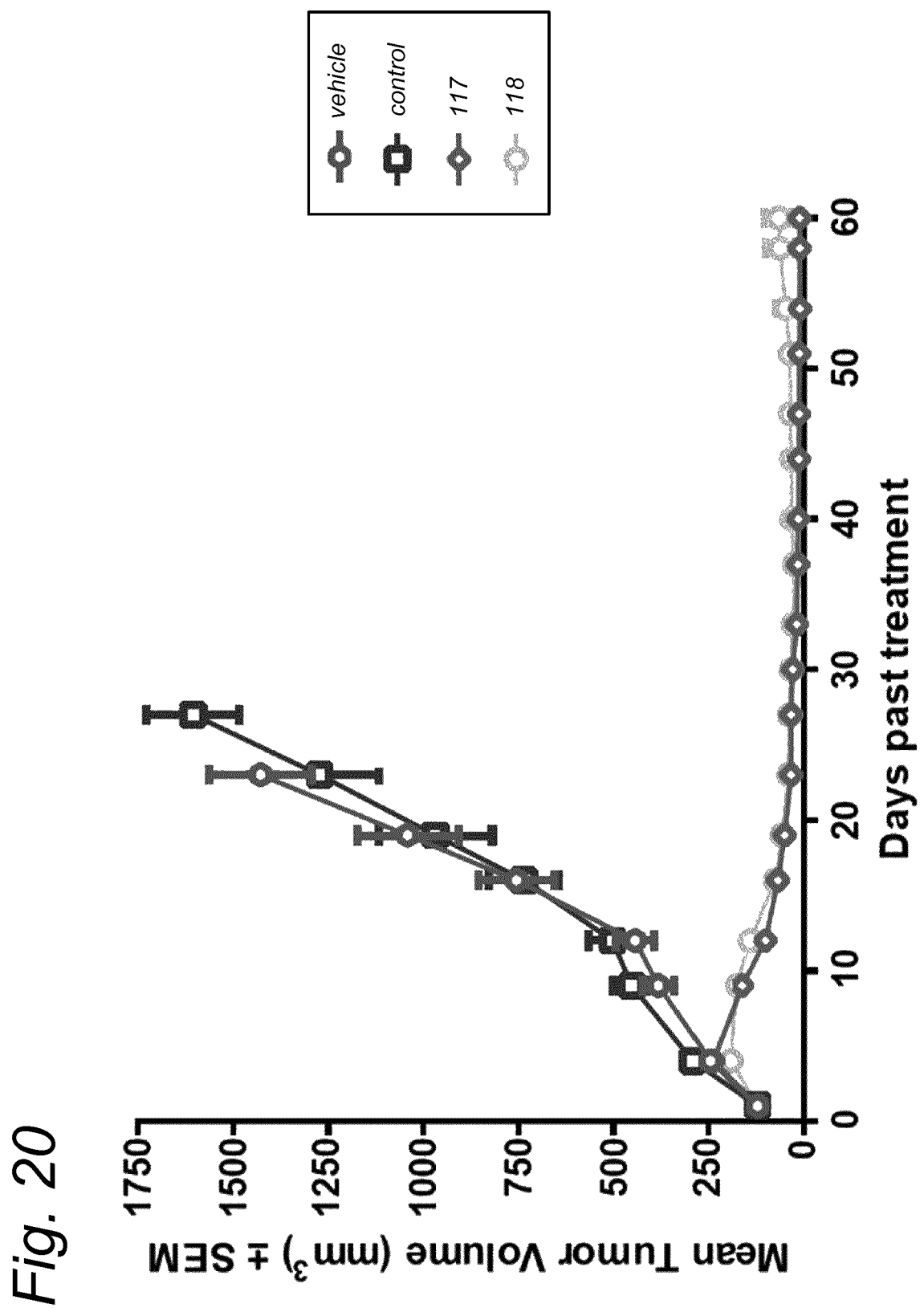
FIG. 20 depicts the results of Example 52 (an efficacy study in MD-MBA-231), wherein the tumour volume (in mm$^3$) is depicted over time using a bioconjugate according to the invention (118) and the same bioconjugate only having a linker outside the present invention (117).

5×10$^6$ MDA-MB-231 tumour cells were subcutaneously implanted to female athymic nude mice. Dosing with vehicle, 117, 118 or (target-negative) control ADC was initiated in groups of 10 mice when tumour volumes reached 88-172 mm$^3$. All treatments were administered intravenously (i.v.) via tail vein injection once. The dosing volume was 10 mL/kg of body weight and was escalated to the body weight of each individual animal. Animals were euthanized if their tumour volume reached the endpoint volume of 1500 mm³ or at the end of the study, whichever came first. For the calculation of mean tumour volume of the group, the following rule was applied: when an animal exited the study due to tumour size, the final tumour volume recorded for the animal was included with the data used to calculate the mean volume at subsequent time points. Tumour volume and body weight values were not used to calculate a group mean tumour volumes/body weight when fewer than 50% of the animals in a group remained in the study. Prism (GraphPad, San Diego, CA) was used for graphical presentations and statistical analyses. Error bars indicate SEM. The average tumour volume for all four groups is graphically depicted in FIG. 20.

Example 53: Rat Safety Studies Performed with mAb-3 ADCs 117 and 118

Rat tolerability studies were conducted at Covance Laboratories in compliance with the U.S. Department of Agriculture's (USDA) Animal Welfare Act, the Guide for the Care and Use of Laboratory Animals from the Institute for Laboratory Animal Research, and the National Institutes of Health (NIH) guidelines. 24 Crl:CD(SD) male rats weighting 250 grams approximately were randomised into groups of 3 animals each. Rats were given a single i.v. dose (2, 3 or 6 mg/kg) of 117, 118 or vehicle via tail vein injection. The dosing volume was 5 mL/kg of body weight and was escalated to the body weight of each individual animal. Animals were euthanized if they showed poor clinical condition or at the end of the study, whichever came first. Animal clinical observations were conducted regularly during the study period. Blood samples (between 100 μL and 1.8 mL) were collected at 1, 3 and 6 hours on day 1; and at day 2, 3, 7, 8, 14 and 21 (end of the study day).

Results: 117 was well tolerated at 3 mg/kg, but poorly tolerated at 6 mg/kg, resulting in early sacrifices on day 10 due to poor clinical conditions. 118 was well tolerated at 3 mg/kg and 6 mg/kg. Body weight gain in all these groups was significantly lower than observed in the vehicle-treated group over the duration of the study, which was associated with reduced food consumption. A dose-dependent reduction in reticulocytes, red cell mass, platelets, neutrophils, monocytes, leukocytes and lymphocytes was observed in animals treated with 117 and 118 at both tested doses (3 and 6 mg/kg). Animals treated with 3 mg/kg of 118 showed evidence of reversibility of these parameters by day 21. MTDs for 117 and 118 were established as 3 and 6 mg/kg, respectively.

```
Sequence identification of fusion protein EndoSH
(SEQ. ID NO: 1):
   1 MPSIDSLHYL SENSKKEFKE ELSKAGQESQ KVKEILAKAQ

QADKQAQELA

51 KMKIPEKIPM KPLHGPLYGG YFRTWHDKTS DPTEKDKVNS

MGELPKEVDL

101 AFIFHDWTKD YSLFWKELAT KHVPKLNKQG TRVIRTIPWR

FLAGGDNSGI

151 AEDTSKYPNT PEGNKALAKA IVDEYVYKYN LDGLDVDVEH

DSIPKVDKKE

201 DTAGVERSIQ VFEEIGKLIG PKGVDKSRLF IMDSTYMADK

NPLIERGAPY

251 INLLLVQVYG SQGEKGGWEP VSNRPEKTME ERWQGYSKYI

RPEQYMIGFS

301 FYEENAQEGN LWYDINSRKD EDKANGINTD ITGTRAERYA

RWQPKTGGVK

351 GGIFSYAIDR DGVAHQPKKY AKQKEFKDAT DNIFHSDYSV

SKALKTVMLK

401 DKSYDLIDEK DFPDKALREA VMAQVGTRKG DLERFNGTLR

LDNPAIQSLE

451 GLNKFKKLAQ LDLIGLSRIT KLDRSVLPAN MKPGKDTLET

VLETYKKDNK

501 EEPATIPPVS LKVSGLTGLK ELDLSGFDRE TLAGLDAATL

TSLEKVDISG

551 NKLDLAPGTE NRQIFDTMLS TISNHVGSNE QTVKFDKQKP

TGHYPDTYGK

601 TSLRLPVANE KVDLQSQLLF GTVTNQGTLI NSEADYKAYQ

NHKIAGRSFV

651 DSNYHYNNFK VSYENYTVKV TDSTLGTTTD KTLATDKEET

YKVDFFSPAD

701 KTKAVHTAKV IVGDEKTMMV NLAEGATVIG GSADPVNARK

VFDGQLGSET

751 DNISLGWDSK QSIIFKLKED GLIKHWRFFN DSARNPETTN

KPIQEASLQI

801 FNIKDYNLDN LLENPNKFDD EKYWITVDTY SAQGERATAF

SNTLNNITSK

851 YWRVVFDTKG DRYSSPVVPE LQILGYPLPN ADTIMKTVTT

AKELSQQKDK

901 FSQKMLDELK IKEMALETSL NSKIFDVTAI NANAGVLKDC

IEKRQLLKKG

951 GGGSGGGGSG GGGSHHHHHH EFGGGGSGGG GSGGGGSAPA

PVKQGPTSVA

1001 YVEVNNNSML NVGKYTLADG GGNAFDVAVI FAANINYDTG

TKTAYLHFNE

1051 NVQRVLDNAV TQIRPLQQQG IKVLLSVLGN HQGAGFANFP

SQQAASAFAK

1101 QLSDAVAKYG LDGVDFDDEY AEYGNNGTAQ PNDSSFVHLV

TALRANMPDK

1151 IISLYNIGPA ASRLSYGGVD VSDKFDYAWN PYYGTWQVPG

IALPKAQLSP
```

```
1201 AAVEIGRTSR STVADLARRT VDEGYGVYLT YNLDGGDRTA

DVSAFTRELY

1251 GSEAVRTP
```

(linker is underlined, EndoH sequence is denoted in italics)

Sequence of His-TnGalNAcT(33-421)(SEQ. ID NO: 2):
```
  1 MGSSHHHHHH SSGLVPRGSH MSPLRTYLYT PLYNATQPTL

RNVERLAANW PKKIPSNYIE

61 DSEEYSIKNI SLSNHTTRAS VVHPPSSITE TASKLDKNMT

IQDGAFAMIS PTPLLITKLM

121 DSIKSYVTTE DGVKKAEAVV TLPLCDSMPP DLGPITLNKT

ELELEWVEKK FPEVEWGGRY

181 SPPNCTARHR VAIIVPYRDR QQHLAIFLNH MHPFLMKQQI

EYGIFIVEQE GNKDFNRAKL

241 MNVGFVESQK LVAEGWQCFV FHDIDLLPLD TRNLYSCPRQ

PRHMSASIDK LHFKLPYEDI

301 FGGVSAMTLE QFTRVNGFSN KYWGWGGEDD DMSYRLKKIN

YHIARYKMSI ARYAMLDHKK

361 STPNPKRYQL LSQTSKTFQK DGLSTLEYEL VQVVQYHLYT

HILVNIDERS
```

---

The invention claimed is:

1. A method for increasing the therapeutic index of a bioconjugate, comprising preparing the bioconjugate of formula (A):

B-Z³-L-(D)_z    (A), wherein:
B is an antibody;
L is a linker linking Z³ and D,
Z³ is a connecting group obtained by reacting a reactive group Q' on a linker-conjugate having a formula Q¹-L-D with a functional group F¹ on the antibody (B), wherein Z³ is connected to B through a glycan on the antibody;
z is 1, 2, 3 or 4;
D is a target molecule; and
each occurrence of "—" is independently a bond or a spacer moiety, by reacting the reactive group Q¹ on the target molecule (D) with the functional group F¹ on the antibody (B), such that L is formula (8a) or (8b) or a salt thereof:

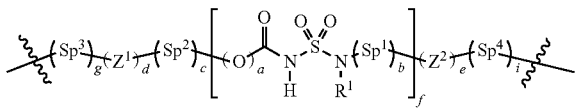

8a

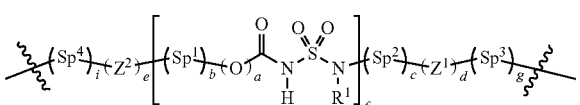

8b wherein:
a is 0 or 1; and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is an additional target molecule D, wherein the target molecule is optionally connected to N via a spacer moiety;

b is 0 or 1;
c is 0 or 1;
d is 0 or 1;
e is 0 or 1;
f is an integer in the range of 1 to 10;
g is 0 or 1;
i is 0 or 1;
wherein at least one of b, e and i is not 0 and at least one of g, d and c is not 0;
D is a target molecule;
$Q^1$ is a reactive group capable of reacting with a functional group $F^1$ present on the antibody;
$Sp^1$ is a spacer moiety;
$Sp^2$ is a spacer moiety;
$Sp^3$ is a spacer moiety;
$Sp^4$ is a spacer moiety;
$Z^1$ is a connecting group that connects $Q^1$ or $Sp^3$ to $Sp^2$, O or C(O) or $N(R^1)$;
$Z^2$ is a connecting group that connects D or $Sp^4$ to $Sp^1$, $N(R^1)$, O or C(O);
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups; or $R^1$ is D, -[$(Sp^1)_b(Z^2)_e(Sp^4)_iD$] or -[$(Sp^2)_c(Z^1)_d(Sp^3)_g Q^1$], wherein D, $Sp^1$, $Sp^2$, $Sp^3$, $Sp^4$, $Z^1$, $Z^2$, D, $Q^1$, b, c, d, e, g and i are as defined above; and the linker is connected to target molecule D via $(Sp^4)_i$.

2. The method according to claim 1, wherein the bioconjugate is suitable for administering to a subject in need thereof.

3. The method according to claim 2, wherein the subject is a cancer patient.

4. The method according to claim 1, wherein the bioconjugate is an antibody-drug-conjugate.

5. The method according to claim 1, wherein target molecule D is an active substance.

6. The method according to claim 1, wherein $Sp^1$, $Sp^2$, $Sp^3$ and $Sp^4$ are independently selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups and $C_9$-$C_{200}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

7. The method according to claim 1, wherein $Z^1$ and $Z^2$ are independently selected from the group consisting —O—, —S—, —N=N—, C(O)—, —C(O)$NR^2$—, —OC(O)—, —OC(O)O—, —OC(O)$NR^2$, —$NR^2$C(O)—, —$NR^2$C(O)O—, —$NR^2$C(O)$NR^2$—, —SC(O)—, —SC(O)O—, —SC(O)$NR^2$—, —S(O)—, S(O)$_2$, —OS(O)$_2$—, —OS(O)$_2$O—, —OS(O)$_2NR^2$—, —OS(O)—, —OS(O)O—, OS(O)$NR^2$—, —$ONR^2$C(O)—, —$ONR^2$C(O)O—, —$ONR^2$C(O)$NR^2$—, —$NR^2$OC(O)—, —$NR^2$OC(O)O—, —$NR^2$OC(O)$NR^2$—, —$ONR^2$C(S)—, —$NRO^2$C(S)O—, —$NRO^2$C(S)$NR^2$—, —$NR^2$OC(S)—, —$NR^2$OC(S)O—, —$NR^2$OC(S)$NR^2$—, —OC(S)—, —OC(S)O—, —OC(S)$NR^2$—, —$NR^2$C(S)—, —$NR^2$C(S)O—, $NR^2$C(S)$NR^2$—, —SS(O)$_2$—, —SS(O)$_2$O—, —SS(O)$_2NR^2$—, $NR^2$OS(O)—, —$NR^2$OS(O)O—, $NR^2$OS(O)$NR^2$—, —$NR^2$OS(O)$_2$—, $NR^2$OS(O)$_2$O—, —$NR^2$OS(O)$_2NR^2$—, —$ONR^2$S(O)—, —$ONR^2$S(O)O—, —$ONR^2$S(O)$NR^2$—, —$ONR^2$S(O)$_2$O—, —$ONR^2$S(O)$_2$ $NR^2$—, —$ONR^2$S(O)$_2$—, OP(O)$(R^2)_2$—, —SP(O)$(R^2)_2$—, —$NR^2$P(O)$(R^2)_2$— and combinations of two or more thereof, wherein $R^2$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

8. The method according to claim 1, wherein $Sp^1$, $Sp^2$, $Sp^3$ and $Sp^4$, if present, are independently selected from the group consisting of linear or branched $C_1$-$C_{20}$ alkylene groups, the alkylene groups being optionally substituted and optionally interrupted by one or more heteroatoms selected from the group consisting of O, S or $NR^3$, wherein $R^3$ is independently selected from the group consisting of hydrogen and $C_1$-$C_4$ alkyl groups, and wherein $Q^1$ is according to formula (9a), (9q), (9n), (9o) or (9p), (9t) or (9zh):

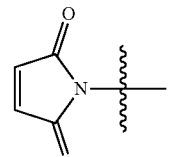

9a

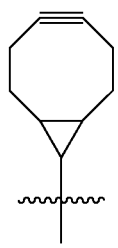

9q

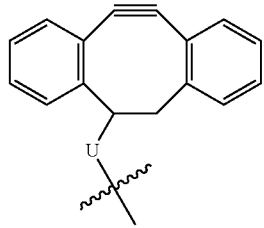

9n

-continued

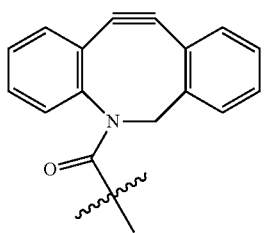
9o

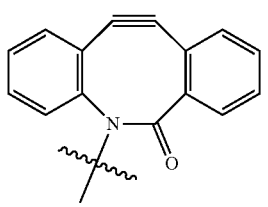
9p

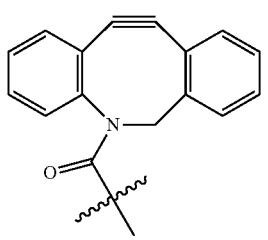
9o

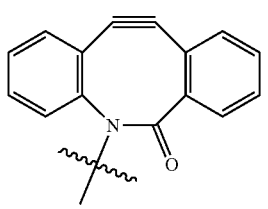
9p wherein:
U is O or NR$^9$, and R$^9$ is hydrogen, a linear or branched C$_1$-C$_{12}$ alkyl group or a C$_4$-C$_{12}$ (hetero)aryl group;

R$^{10}$ is a (thio)ester group; and

R$^{18}$ is selected from the group consisting of, optionally substituted, C$_1$-C$_{12}$ alkyl groups and C$_4$-C$_{12}$ (hetero) aryl groups.

9. The method according to claim 1, wherein the reaction between reactive group Q$^1$ and functional group F$^1$ is a conjugation reaction selected from thiol-alkene conjugation to form a connecting moiety Z$^3$ that may be represented as (10a) or (10b), amino-(activated) carboxylic acid conjugation to form a connecting moiety Z$^3$ that may be represented as (10c), ketone-hydrazino conjugation to form a connecting moiety Z$^3$ that may be represented as (10d) wherein Y=NH, ketone-oxyamino conjugation to form a connecting moiety Z$^3$ that may be represented as (10d) wherein Y=O, alkyne-azide conjugation to form a connecting moiety Z$^3$ that may be represented as (10e) or (10g) and alkene-1,2,4,5-tetrazine conjugation or alkyne-1,2,4,5-tetrazine conjugation to form a connecting moiety Z$^3$ that may be represented as (10h) from which N$_2$ eliminates, wherein moieties (10a), (10b), (10c), (10d), (10e), (10g) and (10h) are represented by:

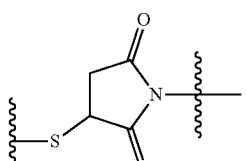
10a

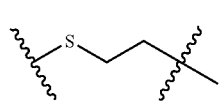
10b

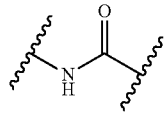
10c

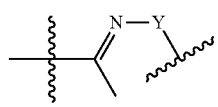
10d

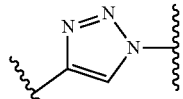
10e

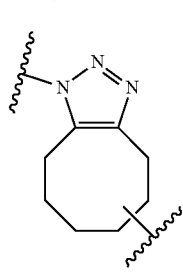
10g

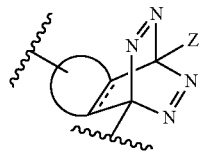
10h wherein Z is selected from hydrogen, methyl and pyridyl.

10. The method according to claim 1, wherein a=0.

11. A method of treatment, comprising administering to a subject a bioconjugate represented by formula (A):

$$B\text{-}Z^3\text{-}L\text{-}(D)_z \qquad (A),$$

wherein:
B is an antibody;
L is a linker linking Z$^3$ and D,
Z$^3$ is a connecting group obtained by reacting a reactive group Q$^1$ on a linker-conjugate having a formula Q$^1$-L-D with a functional group F$^1$ on the antibody (B), wherein Z$^3$ is connected to B through a glycan on the antibody;
z is 1, 2, 3 or 4;
D is a target molecule; and
each occurrence of "—" is independently a bond or a spacer moiety, by reacting the reactive group Q$^1$ on the target molecule (D) with the functional group F$^1$ on a the antibody (B), such that L is represented by formula (8a) or (8b) or a salt thereof:

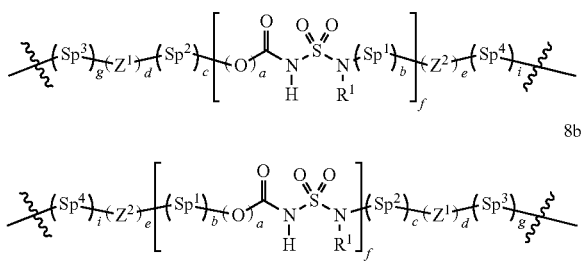

wherein:
a is 0 or 1; and
R$^1$ is selected from the group consisting of hydrogen, C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups, the C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups optionally substituted and optionally interrupted by one or more heteroatoms selected from O, S or NR$^3$ wherein R$^3$ is independently selected from the group consisting of hydrogen and C$_1$-C$_4$ alkyl groups, or R$^1$ is an additional target molecule D, wherein the target molecule is optionally connected to N via a spacer moiety;
b is 0 or 1;
c is 0 or 1;
d is 0 or 1;
e is 0 or 1;
f is an integer in the range of 1 to 10;
g is 0 or 1;
i is 0 or 1;
wherein at least one of b, e and i is not 0 and at least one of g, d and c is not 0;
D is a target molecule;
Q$^1$ is a reactive group capable of reacting with a functional group F$^1$ present on the antibody;
Sp$^1$ is a spacer moiety;
Sp$^2$ is a spacer moiety;
Sp$^3$ is a spacer moiety;
Sp$^4$ is a spacer moiety;
Z$^1$ is a connecting group that connects Q$^1$ or Sp$^3$ to Sp$^2$, O or C(O) or N(R$^1$);
Z$^2$ is a connecting group that connects D or Sp$^4$ to Sp$^1$, N(R$^1$), O or C(O);
R$^1$ is selected from the group consisting of hydrogen, C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups, the C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups optionally substituted and optionally interrupted by one or more heteroatoms selected from O, S and NR$^3$ wherein R$^3$ is independently selected from the group consisting of hydrogen and C$_1$-C$_4$ alkyl groups; or R$^1$ is D, -[(Sp$^1$)$_b$(Z$^2$)$_e$(Sp$^4$)$_i$ D] or -[(Sp$^2$)$_c$(Z$^1$)$_d$(Sp$_3$)$_g$ Q$^1$], wherein D, Sp$^1$, Sp$^2$, Sp$^3$, Sp$^4$, Z$^1$, Z$^2$, D, Q$^1$, b, c, d, e, g and i are as defined above; and
the linker is connected to target molecule D via (Sp$^4$)$_i$.

12. The method according to claim 11, for the treatment of cancer.

13. The method according to claim 5, wherein the active substance is a cytotoxin.

14. The method according to claim 1, wherein the reaction between reactive group Q$^1$ and functional group F$^1$ is a cycloaddition reaction.

15. The method according to claim 1, wherein the glycan is trimmed.

16. The method according to claim 1, wherein the target molecule D has a water solubility of no more than 0.1 wt % in water (20° C. and 100 kPa).

17. The method according to claim 1, wherein a=1.

18. The method according to claim 1, wherein z=2; and/or wherein R$^1$ is an additional target molecule D, wherein the target molecule is connected to N via a spacer moiety.

19. The method according to claim 1, wherein L is represented by formula (8a), b=e=1 and:
Sp$^1$ is selected from the group consisting of linear or branched C$_1$-C$_{20}$ alkylene groups, the alkylene groups being optionally substituted and optionally interrupted by one or more heteroatoms selected from the group consisting of O, S or NR$^3$, wherein R$^3$ is independently selected from the group consisting of hydrogen and C$_1$-C$_4$ alkyl groups;
Z$^2$ is selected from the group consisting —O—, —S—, —NR$^2$—, —N=N—, C(O)—, —C(O)NR$^2$—, —OC(O)—, —OC(O)O—, —OC(O)NR$^2$, —NR$^2$C(O)—, NR$^2$C(O)O—, —NR$^2$C(O)NR$^2$—, —SC(O)—, —SC(O)O—, —SC(O)NR$^2$—, —S(O)—, S(O)$_2$, —OS(O)$_2$—, —OS(O)$_2$O—, —OS(O)$_2$NR$^2$—, —OS(O)—, —OS(O)O—, OS(O)NR$^2$—, —ONR$^2$C(O)—, —ONR$^2$C(O)O—, —ONR$^2$C(O)NR$^2$—, NR$^2$OC(O)—, —NR$^2$OC(O)O—, —NR$^2$OC(O)NR$^2$—, —ONR$^2$C(S)—, ONR$^2$C(S)O—, —ONR$^2$C(S)NR$^2$—, —NR$^2$OC(S), —NR$^2$OC(S)O—, NR$^2$OC(S)NR$^2$—, —OC(S)—, —OC(S)O—, —OC(S)NR$^2$—, —NR$^2$C(S)—, NR$^2$C(S)O—, —NR$^2$C(S)NR$^2$—, —SS(O)$_2$—, —SS(O)$_2$O—, —SS(O)$_2$NR$^2$—, NR$^2$OS(O)—, —NR$^2$OS(O)O—, —NR$^2$OS(O)NR$^2$—, —NR$^2$OS(O)$_2$, NR$^2$OS(O)$_2$O—, —NR$^2$OS(O)$_2$NR$^2$—, —ONR$^2$S(O)—, —NRO$^2$S(O)O, ONR$^2$S(O)NR$^2$—, —ONR$^2$S(O)$^2$O—, —ONR$^2$S(O)$_2$NR$^2$—, —NRO$^2$S(O)$_2$—, OP(O)(R$^2$)$_2$—, —SP(O)(R$^2$)$_2$—, —NR$^2$P(O)(R$^2$)$_2$— and combinations of two or more thereof, wherein R$^2$ is independently selected from the group consisting of hydrogen, C$_1$-C$_{24}$ alkyl groups, C$_2$-C$_{24}$ alkenyl groups, C$_2$-C$_{24}$ alkynyl groups and C$_3$-C$_{24}$ cycloalkyl groups, the alkyl groups, alkenyl groups, alkynyl groups and cycloalkyl groups being optionally substituted.

20. The method according to claim 1, the linker comprises one or more self-immolative moieties that are released upon a biological trigger.

21. The method according to claim 20, wherein the self-immolative moieties includes a peptide spacer comprised in Sp$^1$ and/or Sp$^4$.

* * * * *